(12) United States Patent
Pless

(10) Patent No.: US 7,801,618 B2
(45) Date of Patent: Sep. 21, 2010

(54) AUTO ADJUSTING SYSTEM FOR BRAIN TISSUE STIMULATOR

(75) Inventor: Benjamin D Pless, Atherton, CA (US)

(73) Assignee: NeuroPace, Inc., Mountain View, CA (US)

( * ) Notice: Subject to any disclaimer, the term of this patent is extended or adjusted under 35 U.S.C. 154(b) by 448 days.

(21) Appl. No.: 11/767,432

(22) Filed: Jun. 22, 2007

(65) Prior Publication Data

US 2008/0319511 A1    Dec. 25, 2008

(51) Int. Cl.
    *A61N 1/36* (2006.01)
(52) U.S. Cl. ............... 607/59; 607/45; 607/63
(58) Field of Classification Search ........... 607/59, 607/60, 62, 63
    See application file for complete search history.

(56) References Cited

U.S. PATENT DOCUMENTS

| | | | |
|---|---|---|---|
| 5,370,672 A | 12/1994 | Fowler et al. |
| 5,938,689 A | 8/1999 | Fischell et al. |
| 6,006,124 A | 12/1999 | Fischell et al. |
| 6,016,449 A | 1/2000 | Fischell et al. |
| 6,061,593 A | 5/2000 | Fischell et al. |
| 6,128,538 A | 10/2000 | Fischell et al. |
| 6,134,474 A | 10/2000 | Fischell et al. |
| 6,161,045 A | 12/2000 | Fischell et al. |
| 6,230,049 B1 | 5/2001 | Fischell et al. |
| 6,308,102 B1 | 10/2001 | Sieracki et al. |
| 6,353,754 B1 | 3/2002 | Fischell et al. |
| 6,354,299 B1 | 3/2002 | Fischell et al. |
| 6,360,122 B1 | 3/2002 | Fischell et al. |
| 6,402,678 B1 | 6/2002 | Fischell et al. |
| 6,427,086 B1 | 7/2002 | Fischell et al. |
| 6,459,936 B2 | 10/2002 | Fischell et al. |
| 6,466,822 B1 | 10/2002 | Pless |
| 6,473,639 B1 | 10/2002 | Fischell et al. |
| 6,480,743 B1 | 11/2002 | Kirkpatrick et al. |

(Continued)

OTHER PUBLICATIONS

Gotman, J., "Automatic Seizure Detection: Improvements and Evaluation," Electroencephalogr. Clin. Neurophysiol. (1990); 76(4): 317-24.

*Primary Examiner*—Carl H Layno
*Assistant Examiner*—Brian T Gedeon

(57) ABSTRACT

An implantable neurostimulator for treating disorders such as epilepsy, pain, movement disorders and depression includes a detection subsystem capable of detecting a physiological condition and a therapy subsystem capable of providing a course of therapy in response to the condition. The therapy subsystem includes an auto-adjust module for automatically adjusting one or more parameters of the therapy so that the therapy subsystem can provide an adjusted parameter to the patient and solicit the patient's feedback concerning the adjustment without requiring the presence of, or immediate involvement with, a clinician or physician. The patient feedback can be analyzed by computer, clinician or a combination of both to determine an optimal range of parameters for subsequent courses of therapy. In this manner, information useful in tuning the neurostimulator therapy parameters to optimize them for individual patient can be acquired automatically outside of the traditional clinical setting, saving time and minimizing patient fatigue that otherwise would be experience in marathon, in-clinic tuning sessions. The auto-adjust module also can be configured to prompt the patient to provide feedback even when parameters are not being adjusted, so as to acquire information for a baseline or about any placebo effect when the patient is otherwise expecting changes to the therapy to be made.

30 Claims, 32 Drawing Sheets

U.S. PATENT DOCUMENTS

| | | | |
|---|---|---|---|
| 6,529,774 B1 | 3/2003 | Greene | |
| 6,591,137 B1 | 7/2003 | Fischell et al. | |
| 6,591,138 B1 | 7/2003 | Fischell et al. | |
| 6,597,954 B1 | 7/2003 | Pless et al. | |
| 6,618,623 B1 | 9/2003 | Pless et al. | |
| 6,647,296 B2 | 11/2003 | Fischell et al. | |
| 6,690,974 B2 | 2/2004 | Archer et al. | |
| 6,738,671 B2 | 5/2004 | Christophersom et al. | |
| 6,799,149 B2 | 9/2004 | Hartlaub | |
| 6,810,285 B2 | 10/2004 | Pless et al. | |
| 6,944,501 B1 | 9/2005 | Pless | |
| 7,082,333 B1 | 7/2006 | Bauhahn et al. | |
| 7,089,059 B1 | 8/2006 | Pless | |
| 7,110,820 B2 | 9/2006 | Tcheng | |
| 7,136,695 B2 | 11/2006 | Pless et al. | |
| 7,146,222 B2 | 12/2006 | Boling | |
| 7,174,213 B2 | 2/2007 | Pless | |
| 7,206,632 B2 | 4/2007 | King | |
| 7,277,748 B2 | 10/2007 | Wingeier et al. | |
| 7,283,856 B2 | 10/2007 | Boling | |
| 7,294,101 B2 | 11/2007 | Fischell et al. | |
| 7,341,562 B2 | 3/2008 | Pless et al. | |
| 7,353,065 B2 | 4/2008 | Morrell | |
| 7,494,458 B2 | 2/2009 | Fischell et al. | |
| 7,601,116 B2 | 10/2009 | Fischell et al. | |
| 7,672,736 B2 | 3/2010 | Boling | |
| 7,747,318 B2 | 6/2010 | John et al. | |
| 2004/0138516 A1 | 7/2004 | Osorio et al. | |
| 2004/0138711 A1 | 7/2004 | Osorio et al. | |
| 2004/0158119 A1 | 8/2004 | Osorio et al. | |
| 2004/0181262 A1 | 9/2004 | Bauhahn | |
| 2004/0199216 A1 | 10/2004 | Lee et al. | |
| 2005/0216064 A1 | 9/2005 | Heruth et al. | |
| 2006/0212092 A1 | 9/2006 | Fischell et al. | |
| 2006/0265022 A1 | 11/2006 | John et al. | |
| 2007/0032834 A1 | 2/2007 | Gliner et al. | |
| 2007/0123758 A1* | 5/2007 | Miesel et al. | 600/301 |
| 2007/0213629 A1 | 9/2007 | Greene | |
| 2007/0213783 A1 | 9/2007 | Pless et al. | |
| 2008/0021514 A1 | 1/2008 | Pless | |
| 2008/0058664 A1 | 3/2008 | Mirro | |
| 2008/0077191 A1 | 3/2008 | Morrell | |
| 2008/0195160 A1 | 8/2008 | Wingeier et al. | |
| 2008/0195166 A1 | 8/2008 | Sun et al. | |
| 2008/0195227 A1 | 8/2008 | Boling et al. | |
| 2008/0319335 A1 | 12/2008 | Greene | |
| 2009/0326610 A1 | 12/2009 | Pless et al. | |

* cited by examiner

Patient: John Doe
Date of Report: xx-xx-xxxx
Event Log
A = Discontinue Carbamazepine
B = Begin Zonisamide 200 mg BID Physician: Jane Smith, MD
Date Range: x-x-xxxx to xx-xx-xxxx

AUTO ADJUSTING SYSTEM FOR BRAIN TISSUE STIMULATOR

BACKGROUND OF THE INVENTIONS

1. Field of the Inventions

The inventions disclosed herein are directed to systems, devices and methods for tuning the values of the parameters used in delivering neurostimulation therapy to a patient to provide optimal results from the therapy.

2. Description of the Related Art

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence can be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities in which they can participate. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and/or surgery. The first approach is usually drug therapy. Surgery may include removing portions of the brain or implanting or partially implanting a device that is capable of providing electrical stimulation and/or another type of therapy (e.g., drug therapy).

Electrical stimulation is an emerging therapy for treating epilepsy. However, currently available electrical stimulation devices apply continuous or periodic electrical stimulation to neural tissue surrounding or near implanted electrodes, without regard to or in response to a particular condition or state that is detected for the patient.

Recent research and clinical studies are directed toward applying electrical stimulation or some other therapy in response or reaction to a detected patient condition, for example, the neurological condition of a patient at the onset of epileptiform activity or just prior to the onset of epileptiform activity indicative of a seizure.

The episodic attacks experienced by a typical epilepsy patient are generally electrographically defined as periods of abnormal neurological activity, sometimes referred to as epileptiform activity. The term "ictal" relates to the physiological condition of a seizure.

Most prior work on the detection and responsive treatment of seizures via electrical stimulation has focused on analysis of electroencephalogram (EEG) and electrocorticogram (ECoG) waveforms. In general, EEG signals represent aggregate neuronal activity potentials detectable via electrodes applied to a patient's scalp. ECoG signals, deep-brain counterparts to EEG signals, are detectable via electrodes implanted on or under the dura mater, and usually within the patient's brain. Unless the context clearly and expressly indicates otherwise, the term "EEG" shall be used generically herein to refer to both EEG and ECoG signals.

Much of the work on detection has focused on the use of time-domain analysis of EEG signals. See, e.g., J. Gotman, Automatic seizure detection: improvements and evaluation, Electroencephalogr. Clin. Neurophysiol. 1990; 76(4): 317-24. In a typical time-domain detection system, EEG signals are received by one or more implanted electrodes and then processed by a control module, which then is capable of performing an action (intervention, warning, recording, etc.) when an abnormal event is detected.

It is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified and used to facilitate intervention before electrographic or clinical onsets occur. This capability would be considered seizure prediction, in contrast to the detection of a seizure or its onset.

U.S. Pat. No. 6,016,449 to Fischell, et al. (which is hereby incorporated by reference as though set forth in full herein), describes an implantable seizure detection and treatment system. In the Fischell system, various detection methods are possible, all of which essentially rely upon the analysis (either in the time domain or the frequency domain) of processed EEG signals. Fischell's controller is preferably implanted intracranially, but other approaches are also possible, including the use of an external controller. When a seizure is detected, the Fischell system applies electrical stimulation, hence Fischell discloses a responsive neurostimulator. The responsive capability is discussed in further detail below.

Currently, however, the process of identifying the optimal stimulation therapy to deliver to a particular patient in response to a neurological event is largely one of trial and error. The clinician or physician typically has a set of different parameters that can be modified and then tested with the patient to see what effect the modifications have on the quality of the treatment. For example, the set of parameters available for the clinician to modify in this device or system "tuning" process may include the amplitude of the stimulation pulse, the pulse width, interval between pulses, the total time over which a given "dose" of stimulation therapy is delivered, which of several electrode combinations are used (e.g., two electrodes, or one electrode referenced to the device case, etc.), and the polarities used, etc. Since these different parameters pose the possibility of many different combinations, when this tuning process is undertaken, it is time consuming and fatiguing, especially for the patient, who is asked to provide feedback with respect to each tested parameter condition. Patient fatigue can result in the patient giving inconsistent feedback (e.g., indicating a positive difference on one occasion when the amplitude is increased, and then indicating no change or a negative effect when the amplitude is increased by the same amount later on.) Moreover, a patient's experience with his or her disease can be different depending on the time of day or other factors, such as hormonal activity. Thus, it can be challenging to reliably tune the stimulation parameters so that they are optimal for a particular patient when the only input to the tuning process is obtained during the patient's sessions with the clinician.

SUMMARY OF THE INVENTIONS

Described herein are systems, including devices and methods, for enhancing the tuning process associated with a program of neurostimulation therapy deliverable by a responsive neurostimulator, wherein input from the patient with respect to predetermined changes to various stimulation parameters can be obtained in places and times not limited to the clinician's office while the patient is present. For example, a device can be configured to automatically change a parameter of the therapy delivered by the device and then ask the patient to record, either in a written log or as an electronic input to the device, his or her subjective feedback about the change. Such a device can help caregivers fine tune the therapy outside the confines of office visits with the patient, by automatically varying the values of the available parameters that can be adjusted and automatically asking the patient to input feedback, a testing process that otherwise would require the clinician to manually adjust the parameters and to solicit the patient's response while the clinician and the patient are both engaged in the tuning process. Additionally, the ability to automatically prompt the patient to provide feedback can lead to acquisition of additional data that the clinician can use to assess whether a particular change in a particular parameter is likely to have a desired effect if incorporated into the patient's therapy. For example, if a patient is asked to provide feedback both when a particular adjustment has been made and when it is "undone," these data may reveal that, even though the patient reports a difference in how he or she feels, the patient's perception does not actually correlate to the change in the parameter. In other words, the device can be used to acquire control and/or placebo data.

Thus, in accordance with an embodiment, a device for delivering and monitoring therapy provided to a patient can comprise a therapy device configured to provide a therapy to the patient. A controller can be configured to automatically change at least one parameter of the therapy. Additionally, the device can include a prompting module configured to prompt the patient to express the patient's opinion about the changed therapy.

In accordance with another embodiment, a method of delivering and monitoring electrical stimulation therapy provided to a patient with an implantable neurostimulator can comprise delivering a first course of electrical stimulation therapy with the implantable neurostimulator with a first value of at least one parameter of the electrical stimulation. The method can also include automatically changing the first value to a second value of the least one parameter, delivering a second course of electrical stimulation therapy to the patient with the second value, and prompting the patient to provide input reflecting the patient's opinion about the therapy.

In accordance with yet another embodiment, a device for delivering therapy to a patient can comprise an implantable stimulation means for providing a first treatment to the patient. The device can also include a variation means for automatically varying at least one parameter of the therapy, and a prompting means for prompting the patient to provide input about the therapy.

DETAILED DESCRIPTION OF THE PREFERRED EMBODIMENTS

The inventions are described below with reference to detailed illustrative embodiments. It is apparent that systems according to the inventions can be embodied in a wide variety of forms. Consequently, the specific structural and functional details disclosed herein are representative and do not limit the scope of the inventions. Further, the embodiments disclosed herein are described in the context of an implantable device having a small, self-contained, responsive neurostimulator for providing a course of therapy to a patient because the embodiments disclosed herein have particular utility in this context. However, the embodiments herein can also be applied to other implantable medical devices such as a drug delivery device, an insulin pump or any other implantable medical device capable of providing therapy to a patient, as well as other medical devices.

Figure 1:
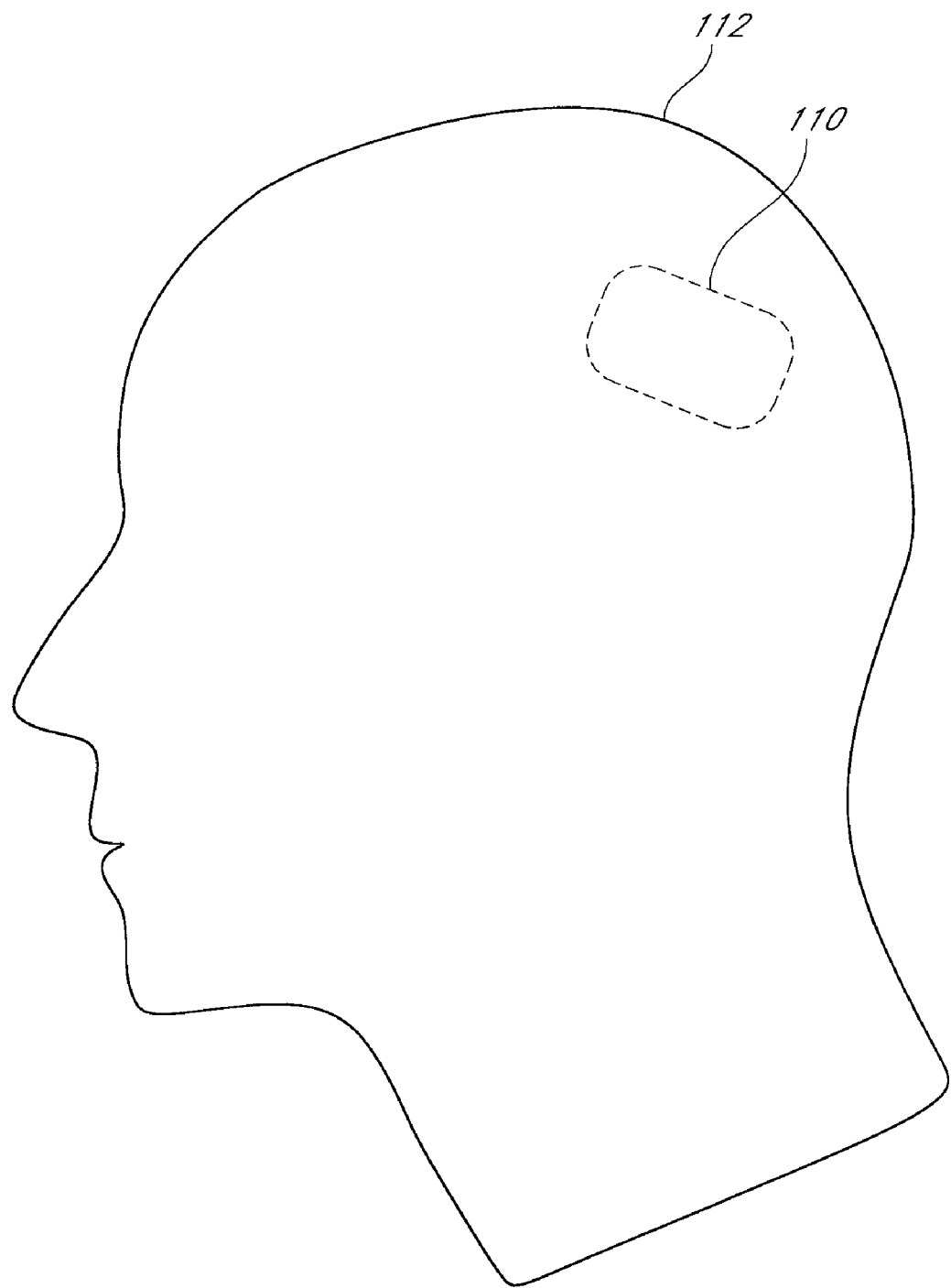
FIG. 1 is a schematic illustration of a patient's head showing the placement of an implantable neurostimulator.

FIG. 1 depicts an embodiment of an intracranially implanted device 110 comprising a small, self-contained, responsive neurostimulator. As the term is used herein, a responsive neurostimulator is a device capable of detecting or predicting ictal activity (or other neurological events) and providing electrical stimulation to neural tissue in response to detection, where the electrical stimulation is specifically intended to terminate or otherwise alter the ictal activity, treat a neurological event, prevent an unwanted neurological event from occurring, or lessen the severity or frequency of certain symptoms of a neurological disorder. The implanted device 110 is advantageously enabled to provide only responsive treatment by providing the device 110 with detection capabilities and stimulation capabilities.

Preferably, the implantable device is capable of detecting or predicting any kind of neurological event that has a representative electrographic signature. While the disclosed embodiment is described primarily as responsive to epileptic seizures, it is also possible to configure the device to respond to other types of neurological disorders, such as movement disorders (e.g. the tremors characterizing Parkinson's disease), migraine headaches, chronic pain, and neuropsychiatric disorders such as depression. Preferably, neurological events representing any or all of these afflictions can be detected when they are actually occurring, in an onset stage, or as a predictive precursor before clinical symptoms or electrographic indicators of the events begin.

As discussed in more detail below, the implantable device 110 can include an internal controller having an auto-adjust module for changing one or more parameters of the neurostimulation therapy to automatically provide a second, different course of therapy to the patient. In addition, the implantable device 110 can be configured to prompt the patient to provide an input reflecting his or her opinions or qualitative assessment of the therapy and the state of his or her conditions when the parameters of the therapy are changed. In some embodiments, the patient input can be recorded and stored in a memory module within the implantable device 110. Additionally or alternatively, a system incorporating a device such as the implantable device 110 can include an external patient-reporting device that is in communication with the implantable device 110 for receiving and recording patient input about the therapy and the state of his or her condition when the therapy is changed.

The combination of an auto-adjust module with a prompt for patient input allows a process for searching for the optimal therapy parameters, which incorporates the device 110 or the system noted above, to be more automated than the process is when the clinician is adjusting the parameters and obtaining and reacting to feedback from the patient as to the perceived effects of the adjustments. This is further advantageous because, since the process is more automated, the variation of the parameters does not have to be attempted only in often lengthy sessions with the clinicians, but can be undertaken more often but over shorter periods of time so that the time-per-tuning session, in which the patient is called upon to provide feedback, is less and the patient will be less fatigued by the adjustment process.

Additionally, embodiments of the device 110, system, and/or process can help to identify and ignore spurious responses from a patient. For example, the device 110 can be configured to prompt a patient for feedback at different times of the day, whether or not the therapy delivered by the device 110 has been changed. As such, a clinician reviewing the patient feedback can separate out changes in response due to time of day and/or other tangential reasons. As such, for example, the patient's subjective reaction to the same, recently changed therapy, can be tested at multiple times (i.e., not constrained by the boundaries of the duration of a visit to the clinician) and thus may result in more consistent feedback for the same changes in parameters.

Further, a clinician may determine, based on a patient's subjective feedback over the course of a period of time when the therapy has not been changed, such as a single day, that the patient exhibits physiological or psychological cycling, for example, caused by cyclic hormonal activity or disorders such as bi-polar disorder. As such, the clinician may ultimately determine that the same parameter should be adjusted to different values at different portions of a day, week, month, year, etc. Such an adjustment scheme may help compensate for the physiological and/or psychological cycling noted above.

Figure 2:
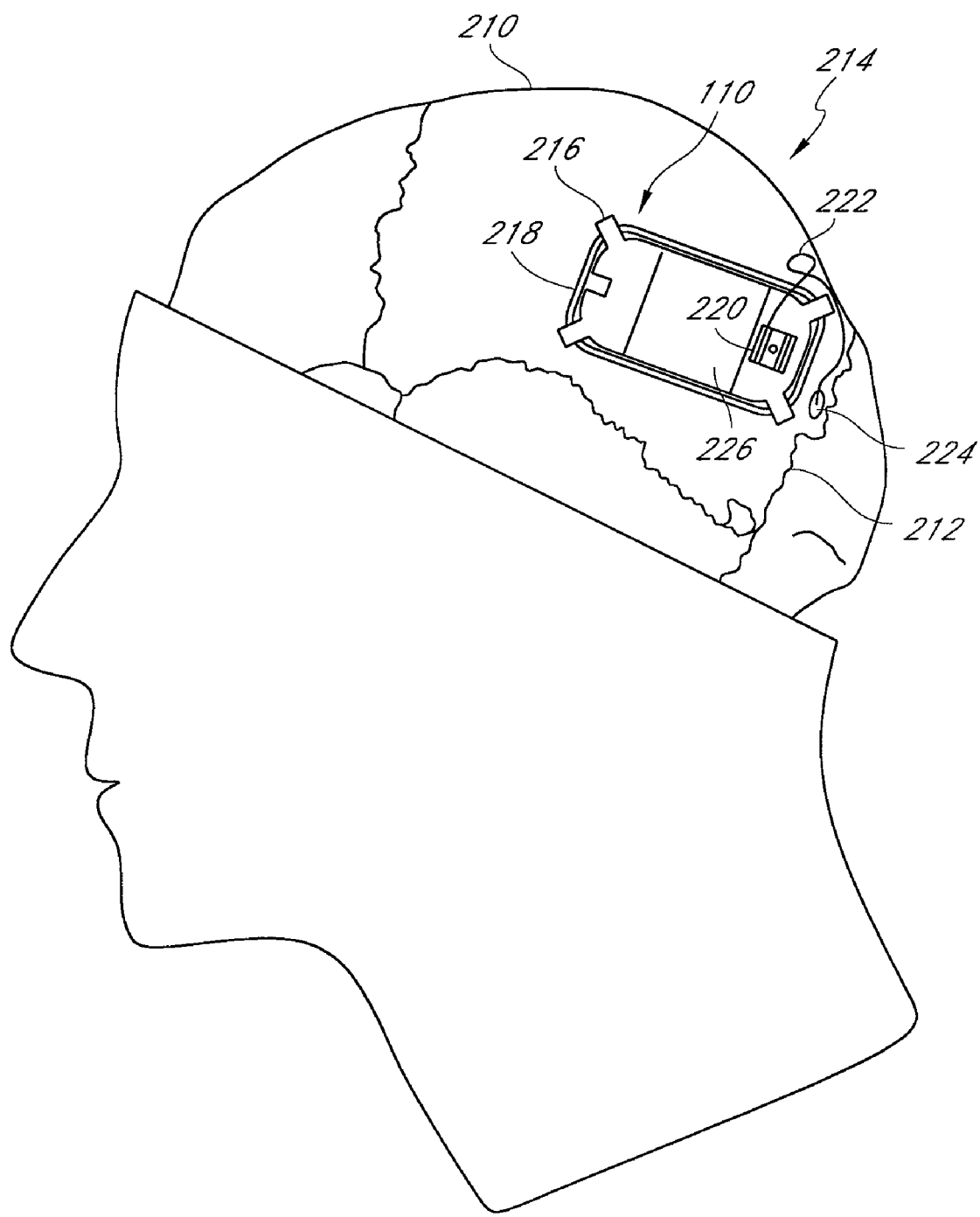
FIG. 2 is a schematic illustration of a patient's cranium showing the implantable neurostimulator of FIG. 1 as implanted, including leads extending to the patient's brain.

In some of the disclosed embodiments, the device 110 is implanted intracranially in a patient's parietal bone 210, in a location anterior to the lambdoidal suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 can be configured to fit the contours of the patient's cranium 214. In some embodiments, the device 110 can be implanted under the patient's scalp 112 but external to the cranium. In yet other alternative embodiments, when it is not possible to implant the device intracranially, it can be implanted pectorally (not shown), with leads extending through the patient's neck and between the patient's cranium and scalp, as necessary.

Some of the embodiments of the device 110 described and illustrated herein are responsive neurostimulators for detecting and treating epilepsy by detecting seizures or their onsets or precursors, and preventing terminating and/or attenuating such epileptic seizures. However, as discussed above, it is envisioned that the device 110 can comprise a responsive neurostimulator capable of detecting and providing a therapeutic response to other types of neurologic disorders such as chronic pain, movement disorders, and psychiatric disorders such as depression. In some embodiments, the device 110 is not a responsive neurostimulator, but is an apparatus capable of detecting neurological conditions and events and providing alternative types of therapy, such as a drug delivery, sound stimulation, etc, in response thereto.

The device 110, as implanted intracranially, is illustrated in greater detail in FIG. 2. The device 110 can be affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in other embodiments of the devices, systems, or methods described herein, is a flexible elongated member having one or more conductors. As shown, the lead 222 can be coupled to the device 110 via the lead connector 220, and can be generally situated on the outer surface of the cranium 214 (and under the patient's scalp 112), extending between the device 110 and a burr hole 224 or other cranial opening, where the lead 222 enters the cranium 214 and is coupled to a depth electrode (see FIG. 4) implanted in a desired location in the patient's brain. As described in U.S. Pat. No. 6,006,124 to Fischell, et al., which is hereby incorporated by reference as though set forth in full herein, the burr hole 224 is sealed after implantation to prevent further movement of the lead 222. In some embodiment, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in other implanted devices, such as cardiac pacemakers, and would serve advantageously in this context. As the device 110 is self-contained, the housing 226 encloses a battery and any electronic circuitry necessary or desirable to provide the functionality described herein, as well as any other features. As described in further detail below, in some embodiments, a telemetry coil can be provided outside of the housing 226 (and potentially integrated with the lead connector 220) to facilitate communication between the device 110 and external devices. Additionally, in some embodiments, a bone conduction microphone, or other device capable of providing an acoustic signal audible to the patient can be located within or outside the housing.

Some embodiments of the neurostimulator configuration described herein and illustrated in FIG. 2 can provide several advantages over alternative designs. For example, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

Figure 3:
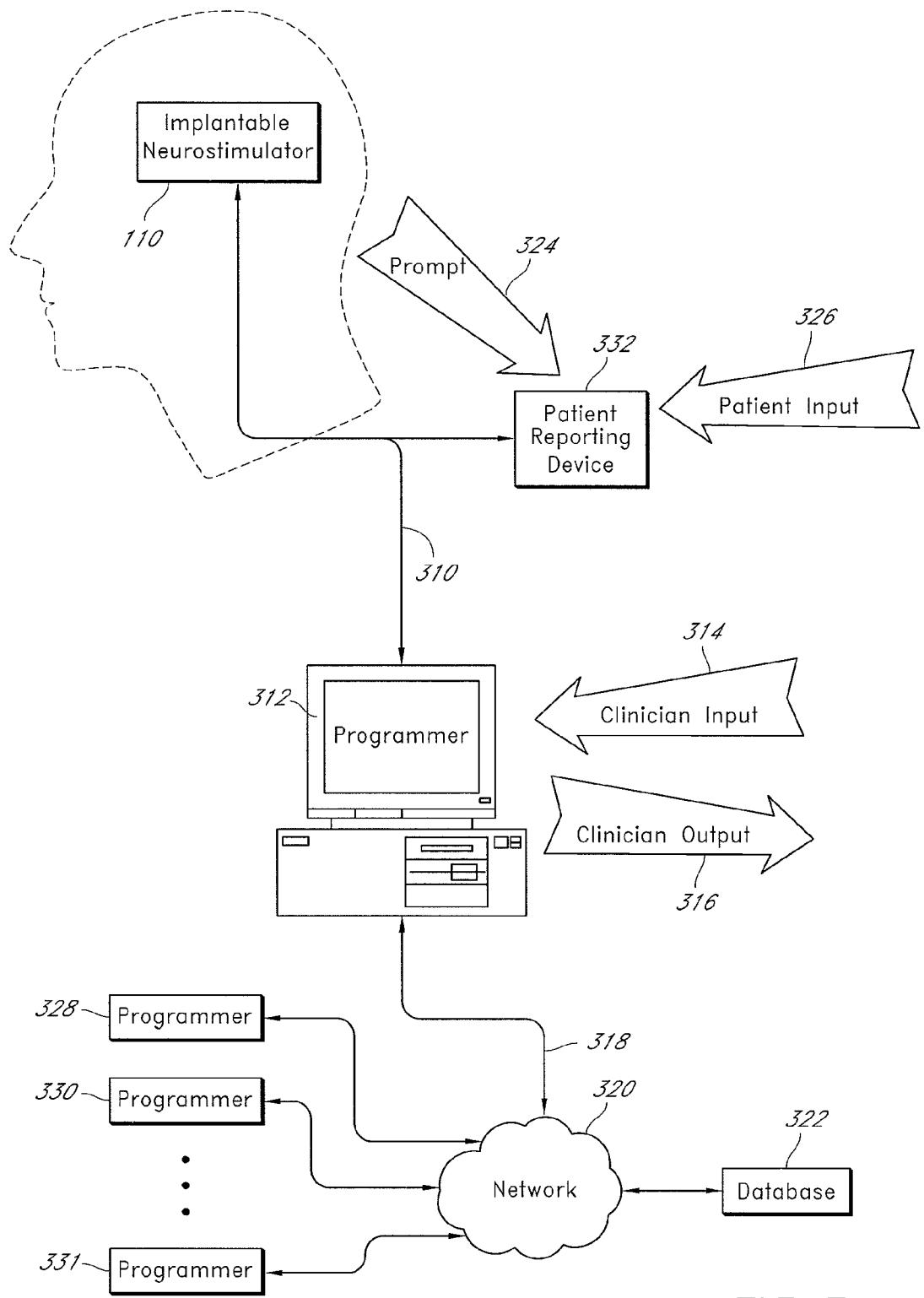
FIG. 3 is a block diagram of an implantable neurostimulator system according to an embodiment used in conjunction with external equipment.

As stated above, and as illustrated in FIG. 3, in some embodiments, the device 110 can operate in conjunction with external equipment. The device 110 is mostly autonomous (particularly when performing its usual sensing, detection, and stimulation capabilities), but can include a selectable part-time wireless link 310 to external equipment such as a patient-reporting device 332 or a programmer 312. In some embodiments, the wireless link 310 can be established by moving the external device into communication range with the implantable device 110. Alternatively, a wand (or other apparatus) having communication capabilities and coupled to the external device can be placed into communication range with the device 110.

In some embodiments, the wireless link 310 can be used to send a prompt to the patient-reporting device 332 that will ask the patient to provide input 326 to the patient-reporting device 332. For example, when the therapy applied by the device 110 is changed, the implantable device 110 can send a message to the patient-reporting device 332 over the wireless link 310 to prompt the patient to report on the status of his or her condition, for example pain, movement or mood, as the therapy being applied is changed. In some embodiments, the implantable device 110 can also be configured to send a prompt over the wireless link 310 when no changes have been made to the therapy. In some embodiments, the patient is not informed when the therapy settings are being adjusted, thus, it can be advantageous that the patient-reporting device 332 prompts the patient for input 326 both when changes have been made and when no changes have been made.

In some embodiments, the patient-reporting device 332 can be a dedicated recording and storage device having a communications capability for receiving and transmitting signals, so that the patient-reporting device 332 will prompt the patient to provide input to it whenever the patient-reporting device receives a signal over the wireless link 310 indicating that a parameter that defines the therapy delivered by the device 110 (e.g., pulse amplitude) has been changed. The patient-reporting device 332 can have an input module for receiving the patient input and a memory subsystem for recording and storing the patient input in the patient-reporting device 332. The patient-reporting device 332 can then be taken to a clinician where the clinician can access and analyze the stored information and use the patient's reaction to different adjustments in different parameters as one piece of information in determining how to program the device 110 for that particular patient. In alternative embodiments, the patient-reporting device 332 can further have a communications capability so that the patient can transmit the information in the device 332 concerning changes in the parameter settings an the patient feedback associated therewith to either the device 110 itself, for example, to a memory module in the device 110 from which the feedback information can be later uploaded to another system and accessed by a clinician), or to a remote database (e.g., over an Internet connection), so that the recorded information can be accessed and analyzed by the clinician at times other than when the clinician is on-site with the patient or when the clinician and patient are otherwise both engaged in the tuning procedure.

In some embodiments, the patient-reporting device 332 can comprise a website or software program accessed by a PDA, such as a BLACKBERRY PDA, a "smart" cell phone, Internet-enabled PC or other communications device. For example, the implanted device 110 can be configured to send a signal over the wireless link 310 to a PDA which then alerts the patient via an audible signal such as a beep or a ring tone, a visual signal, a tactile signal, or any other signal, to provide an input. In addition, the PDA can open a new email and prepopulate all or some of address, subject and body fields, leaving the patient to fill in the email with his or her feedback about the parameter adjustment. For example, the PDA can be configured to automatically address the email to a physician or database, input the patient name or other identifying data in the subject line and/or provide additional patient information, and identifying data about the therapy, such as time and date information and therapy parameters, in the body of the email. Once the patient receives the prepopulated email, the patient simply records his opinions about the therapy provided and the state of his conditions at that time and sends the email. In some embodiments, patient can provide a free-form commentary expressing his thoughts and opinions regarding the therapy and his condition. Alternatively, the patient-reporting device can use standardized questions with graded responses (for example from one to five) to elicit specific information regarding the adjusted therapy.

In some embodiments, the patient-reporting device 332 can also include an analysis module for analyzing the patient input and determining a new value or range of values for parameters to be explored or avoided without requiring involvement of the clinician or other physician. The patient-reporting device 332 can be configured to upload the new value or range of values to be explored to the implantable device 110 via the wireless communication link 310. The patient-reporting device 332 can also be configured to upload the patient input and new values or ranges of values to a database to allow a physician to monitor any trends in the patient's condition that correlate to, or that appear to correlate to, the different parameter adjustments.

In some embodiments, an external programmer 312 can be periodically placed in communication with the implantable device 110. The programmer 312 can then be used to manually control the operation of the device, as well as to transmit information to or receive information from the implantable device 110. Several specific capabilities and operations performed by the programmer 312 in conjunction with the device will be described in further detail below.

The programmer 312 can be configured to perform a number of advantageous operations in connection with some embodiments. For example, the programmer 312 can be configured to specify and set variable parameters in the implantable device 110 to adapt the function of the device 110 to meet the patient's needs. The programmer 312 can also be configured to upload or receive data (including but not limited to stored EEG waveforms, parameters, or logs of actions taken) from the implantable device 110 to the programmer 312 and download or transmit program code and other information from the programmer 312 to the implantable device 110. In some embodiments, the programmer can be further configured to command the implantable device 110 to perform specific actions or change modes as desired by a clinician operating the programmer 312. To facilitate these functions, the programmer 312 can be adapted to receive clinician input 314 and provide clinician output 316; data can be transmitted between the programmer 312 and the implantable device 110 over the wireless link 310. For example, in some embodiments, the clinician can analyze the data from the patient-reporting device 332 and determine a new range of values for therapy parameters to explore or to avoid. The clinician can then use the programmer 312 to upload the new values for the therapy parameters to the implantable device 110.

The programmer 312 can be used at a location remote from the implantable device 110 if the wireless link 310 is enabled to transmit data over long distances. For example, the wireless link 310 can be established by a short-distance first link between the implantable device 110 and a transceiver, with the transceiver enabled to relay communications over long distances to a remote programmer 312, either wirelessly (for example, over a wireless computer network) or via a wired communications link (such as a telephonic circuit or a computer network).

One or more programmers, such as the programmer 312, can also be coupled via a communication link 318 to a network 320 such as the Internet. These types of programmers are identified in FIG. 3 by the reference numerals 328, 330, 331. This type of arrangement allows any information uploaded from the implantable device 110, as well as any program code or other information to be downloaded to the implantable device 110, to be stored in a database 322 at one or more data repository locations (which can include various servers and network-connected programmers like the programmers 328, 330, 331). This would allow a patient (and the patient's clinician) to have access to important data, including past treatment information and software updates, essentially anywhere in the world that there is a programmer (like the programmers 328, 330, 331) and a network connection. Alternatively, the programmers 328, 330, 331 can be connected to the database 322 over a trans-telephonic link.

In yet other alternative embodiments (not illustrated in FIG. 3), the wireless link 310 from the implantable device 110 can enable a transfer of data from the device 110 to the database 322 without any involvement by the programmer 312. In this embodiment, as with others, the wireless link 310 can be established by a short-distance first link between the implantable device 110 and a transceiver, with the transceiver enabled to relay communications over long distances to the database 322, either wirelessly (for example, over a wireless computer network) or via a wired communications link (such as trans-telephonically over a telephonic circuit, or over a computer network). For example, in some embodiments wherein the patient input is recorded directly into the memory subsystem of the implantable device 110, the input can then be transferred to a remote database 322 over the wireless link 310. Thus, the input can be accessed by the clinician to review and analyze reports of any trends in the patient's condition and the parameter settings of the device 110.

The implantable device 110 (FIG. 1) can interact with the programmer 312 (FIG. 3) as described below with reference to FIG. 4. Data stored in the memory subsystem 431 can be retrieved by the patient's clinician through the wireless communication link 310, which operates through the communication subsystem 434 of the implantable device 110. In some embodiments, the data stored in the memory subsystem 431 include the patients input on the therapy, for example when patient input is recorded directly into the implantable device, or when the patient input has been automatically uploaded to the memory subsystem 431 by an external patient-reporting device 332. Alternatively, the patient can bring the external patient-reporting device 332 to the clinician where the stored patient input can be manually uploaded to the programmer 312.

Once the data has been retrieved, a software operating program run by the programmer 312 can allow the clinician to read out a history of events detected, including EEG information before, during, and after each event, or other specific information relating to the detection of each event, the therapy applied, adjustments made to the therapy and patient input on the therapy parameter values that are tested with the patient. The software operating program can be configured to analyze the data and to assist the clinician in determining recommended program settings for the therapy parameters which can then be programmed into the implanted device 110 via any of the programmers 312, 328, 330, 331. The programmers 312, 328, 330, 331 also allow the clinician to specify or alter any programmable parameters of the implantable device 110.

In some embodiments, the programmer 312, 328, 330, 331 can be a commercially available PC, laptop computer, or workstation having a CPU, keyboard, mouse and display, and running a standard operating system such as Microsoft Windows®, Linux®, Unix®, or Apple Mac OS®. It is also envisioned that a dedicated programmer apparatus with a custom software package (which cannot use a standard operating system) can be used.

Figure 4:
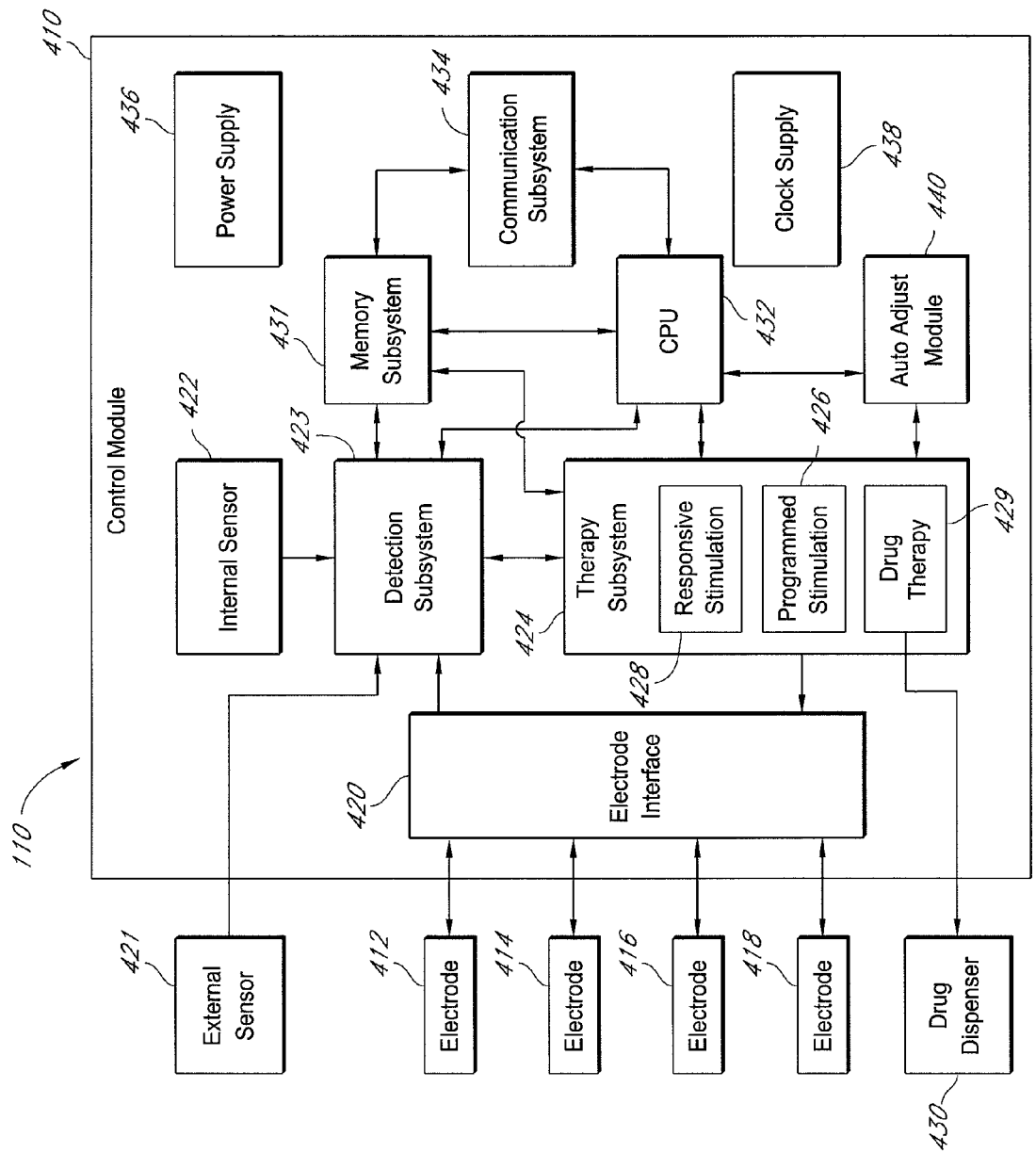
FIG. 4 is a block diagram of an embodiment of the implantable neurostimulator of FIG. 2 for responsive treatment of neurologic disorders.

An overall block diagram of an embodiment of a device 110 used for measurement, detection, treatment is illustrated in FIG. 4. Inside the housing 226 (FIG. 2) of the device 110 are several subsystems making up a control module 410. The control module 410 is capable of being coupled to a plurality of electrodes 412, 414, 416, and 418 (each of which can be connected to the control module 410 via a lead for sensing, stimulation, or both. In the illustrated embodiment, the coupling is accomplished through the lead connector 220 (FIG. 2). Although four electrodes are shown in FIG. 4, it should be recognized that any number is possible, and in the embodiment described in detail below, eight electrodes are used. In fact, it is possible to employ an embodiment that uses a single lead with at least two electrodes, or two leads each with a single electrode (or with a second electrode provided by a conductive exterior portion of the housing 226 in one embodiment), although bipolar sensing between two closely spaced electrodes on a lead is preferred to minimize common mode signals including noise.

The electrodes 412-418 are connected to an electrode interface 420. Preferably, the electrode interface is capable of selecting each electrode as required for sensing and stimulation. The electrode interface 420 also can provide any other features, capabilities, or aspects, including but not limited to amplification, isolation, and charge-balancing functions, that are required for a proper interface with neurological tissue and not provided by any other subsystem of the device 110. The electrode interface 420, an external sensor 421, and an internal sensor 422 are all coupled to a detection subsystem 423 and the electrode interface 420 is also connected to a therapy subsystem 424.

The detection subsystem 423 can include an EEG analyzer function. The EEG analyzer function is adapted to receive EEG signals from the electrodes 412-418, through the electrode interface 420, and to process those EEG signals to identify neurological activity indicative of neurological disorders such as epilepsy, movement disorders and psychiatric disorders. Various inventive methods for performing such detection are described in detail below.

The detection subsystem can optionally also contain further sensing and detection capabilities, including but not limited to parameters derived from other physiological conditions (such as electrophysiological parameters, temperature, blood pressure, etc.), which can be sensed by the external sensor 421 or the internal sensor 422. For example, it can be advantageous to provide an accelerometer or an EMG sensing electrode as the external sensor at a location remote from the implantable device 110 (e.g., in one of the patient's limbs that is subject to tremor). The external sensor 421 can be connected to the device 110 (and the detection subsystem 423) by a lead or by wireless communication, such as a wireless intrabody signaling technique. To detect head tremor or orientation (e.g., for sleep detection), an accelerometer might be used as the internal sensor 422. Other sensors, such as for temperature, blood pressure, or drug concentration might be implemented as part of the external sensor 421 or the internal sensor 422. Other sensor configurations are of course possible and are deemed within the scope the inventions disclosed herein.

The therapy subsystem 424 can be configured to apply electrical stimulation to neurological tissue through the electrodes 412-418. This can be accomplished in any of a number of different manners. For example, it can be advantageous in some circumstances to provide stimulation in the form of a substantially continuous stream of pulses, or on a scheduled basis. This form of stimulation, referred to herein as "programmed" or "predetermined" stimulation, is provided by a programmed stimulation function 426 of the therapy subsystem 424. In alternative embodiments, the therapeutic stimulation can be provided in response to abnormal events detected by the data analysis functions of the detection subsystem 423. This form of stimulation, namely responsive stimulation, is provided by a responsive stimulation function 428 of the therapy subsystem 424. In alternative embodiments, the therapy can include a combination of programmed stimulation and responsive stimulation.

As illustrated in FIG. 4, the therapy subsystem 424 and the data analysis functions of the detection subsystem 423 are in communication. This can facilitate the ability of therapy subsystem 424 to provide responsive stimulation as well as an ability of the detection subsystem 423 to blank the amplifiers while stimulation is being performed to minimize stimulation artifacts. It is contemplated that the parameters of the stimulation signal (e.g., frequency, duration, waveform) provided by the therapy subsystem 424 would be specified by other subsystems, such as the auto-adjust module 440 located in the control module 410, as will be described in further detail below.

In some embodiments, the therapy subsystem 424 is also capable of a drug therapy function 429, in which a drug is dispensed from a drug dispenser 430. As with electrical stimulation, this capability can be provided either on a programmed basis (or continuously) or responsively, after an event of some kind is detected by the detection subsystem 423.

Also in the control module 410 is a memory subsystem 431 and a central processing unit (CPU) 432, which can take the form of a microcontroller. The memory subsystem is coupled to the detection subsystem 423 (e.g., for receiving and storing data representative of sensed EEG signals and other sensor data), the therapy subsystem 424 (e.g., for providing stimulation waveform parameters to the therapy subsystem), and the CPU 432, which can control the operation of the memory subsystem 431. In addition to the memory subsystem 431, the CPU 432 is also connected to the detection subsystem 423 and the therapy subsystem 424 for direct control of those subsystems.

The CPU 432 includes an auto-adjust module 440 for automatically varying one or more parameters of the therapy being applied to the patient. The auto-adjust module 440 can instruct the CPU 432 to alter one or more parameters of the therapy signal being applied in order to provide a second different course of therapy to the patient. For example, the auto-adjust module 440 can instruct the CPU 432 to change any of pulse amplitude, pulse width, pulse-to-pulse interval, electrodes used or amount of time the simulation signal is delivered. For example, but without limitation, the auto-adjust module 440 can be configured to increase or decrease the amplitude of the stimulation signal by a percentage (e.g., 1, 2, 3, 5, 7, etc., or any multiple thereof).

Additionally, the auto-adjust module 440 can be configured to change the parameters of the therapy according to a predetermined schedule input, for example, by the external programmer, in a pseudorandom manner, in a completely random manner, or according to the detection signal received by the detection subsystem 423. In some embodiments, the auto-adjust module 440 can be configured to cycle through a predetermined range of parameters at fixed times of the day for a short period of time in order to explore optimal parameters for the therapy.

Also provided in the control module 410, and coupled to the memory subsystem 431 and the CPU 432, is a communication subsystem 434. The communication subsystem 434 enables communication between the implantable neurostimulator device 110 (FIG. 1) and the outside world, such as an external patient-reporting device 332 or an external programmer 312 (FIG. 3). As set forth above, in some embodiments, the communication subsystem 434 can include a telemetry coil (which can be situated outside of the housing 226) enabling transmission and reception of signals, to or from an external apparatus, via inductive coupling. Alternative embodiments of the communication subsystem 434 could use an antenna for an RF link or an audio transducer for an audio link.

In some embodiments, the communication subsystem 434 can be configured to provide a signal to the patient when the parameters of the therapy are adjusted. For example, in some embodiments, the communications subsystem 434 can include a bone conduction microphone (not shown) positioned outside the implant housing for providing an audible signal to the patient when the therapy is adjusted. The communication subsystem 434 can provide a tonal signal to the bone conduction microphone, or alternatively, the communication subsystem 434 can include prerecorded instructions prompting the patient to record input on the therapy being provided and the state of his condition. In an alternative embodiment, the communication subsystem 434 can trigger the electrodes to provide a stimulation signal to the patient's brain that is distinct from the therapy signal. The different stimulation signal can then act as a prompt to the patient to record his input regarding the therapy. In such embodiments wherein the patient prompt to provide input on the therapy is integrated into the implantable device 110, the control module 410 can further include a recording device (not shown) for receiving and recording input from the patient. The memory subsystem 431 can then be configured to record and store the patient input received from the recording device which can later be downloaded to a remote database, or a programmer for analysis. Alternatively, the patient can simply be instructed to manually record his opinions regarding the therapy and the state of his condition in a handwritten log which can be given to the clinician for analysis.

In an alternative embodiment, when the parameters of the therapy are adjusted, the communication subsystem 434 can send a signal via a wireless link to an external patient-reporting device 332 (FIG. 3) which will prompt the patient to provide input on the therapy and the state of his condition to the external patient-reporting device 332. For example, in some embodiments, the communication subsystem 434 can send a signal to a patient-reporting device 332 located in a PDA, such as a BLACKBERRY PDA, "smart" cell phone, Internet-enabled PC or other standard communications device which prompts the patient via an audible signal such as a beep or a ring tone.

As discussed above, the communication subsystem 434 can also provide a signal prompting the patient to provide input when no changes to the therapy have been made to ensure that the patient is not basing his or her input on expectations of a change in the therapy. For example, the communications subsystem 434 can be programmed to provide random or pseudorandom prompts to the patient throughout the day so that the patient does not know whether she is providing input in response to an actual change in a parameter value.

Rounding out the subsystems in the control module 410 are a power supply 436 and a clock supply 438. The power supply 436 supplies the voltages and currents necessary for each of the other subsystems. The clock supply 438 supplies substantially all of the other subsystems with any clock and timing signals necessary for their operation.

Although the memory subsystem 431 is illustrated in FIG. 4 as a separate functional subsystem, the other subsystems can also require various amounts of memory to perform the functions described above and others. Furthermore, while the control module 410 is preferably a single physical unit contained within a single physical enclosure, namely the housing 226 (FIG. 2), it can comprise a plurality of spatially separate units each performing a subset of the capabilities described above. Also, it should be noted that the various functions and capabilities of the subsystems described above can be performed by electronic hardware, computer software (or firmware), or a combination thereof. The division of work between the CPU 432 and the other functional subsystems can also vary—the functional distinctions illustrated in FIG. 4 may not reflect the integration of functions in a real-world system or method according to the invention.

Figure 5:
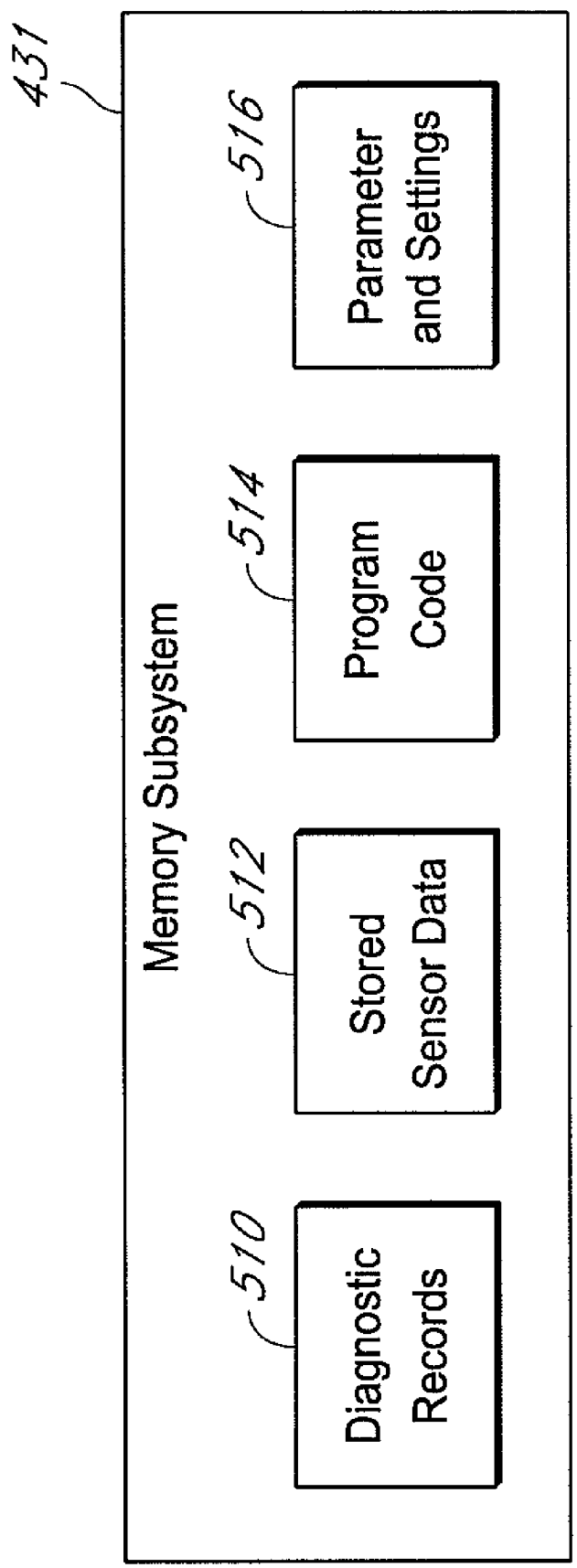
FIG. 5 is a block diagram illustrating data structures that can be stored in a memory subsystem of an implantable neurostimulator.

FIG. 5 illustrates the contents of the memory subsystem 431 and the data structures it can be configured to contain in some embodiments.

In particular, as described generally above and in detail below, the implantable device 110 can be configured to detect neurological events and conditions characteristic of epileptic episodes, movement disorders, pain and depression and is capable of storing such information and communicating it to external equipment such as the programmers 328, 330, 331.

A first storage facility within the memory subsystem 431 can be adapted to store diagnostic records received from the implantable device 110. For example, the diagnostic records 510 can generally include the time of and details regarding any neurological events detected by the implantable device 110 (such as instances of a seizure or a detected tremor) or actions performed by the implantable device 110. For tremors, the details stored among the diagnostic records 510 might include time of day, detected frequency, amplitude, and what therapeutic actions might have been taken. Possible therapeutic actions performed might include electrical stimulation applied, mode changes, interrogation attempts, programming attempts, and other operations. For applied electrical stimulation, the specific details recorded among the diagnostic records 510 might include time of day, stimulation waveform used, amplitude, and outcome (i.e., whether the tremor ceased).

In some embodiments, the first storage facility storing diagnostic records 510 can also store input received from the patient, such as a verbal recording of the patient's opinions about the applied therapy. As discussed above, the patient can be prompted by an audible or other sensory signal to provide a verbal input regarding the applied therapy which can then be recorded by the communication subsystem 434 and stored in the first storage facility along with the diagnostic records about the event detected and therapy applied. In some embodiments, the patient input can be correlated with the diagnostic records for the specific therapy on which the patient is providing input. When the patient is prompted to provide input at a time when no changes have been made to any of the therapy parameters (e.g., to establish a baseline or assess any placebo effect), the patient input can, for example, be correlated to a time the input was provided or to a record indicating that no changes in any parameter values were s applied. In some embodiments, an additional storage facility (not shown), separate from the first storage facility storing diagnostic records 510, can also be provided for the patient input.

A second storage facility 512 within the memory subsystem 431 can be adapted to store sensor data. The implantable device 110 can be capable of recording EEG data from the electrodes 412-418 and other sensor data from external and internal sensors 421, 422 when conditions dictate (e.g., immediately before and after a detected event, on a scheduled basis, or upon command). For additional information on EEG recording in the context of a neurostimulator used to treat epileptic seizures, see U.S. Pat. No. 6,128,538, filed on Nov. 29, 1999, and issued on Oct. 3, 2000, the entirely of which is hereby incorporated herein.

A third storage facility 514 within the memory subsystem 431 can be configured to store any program code required for the CPU 432 and any other subsystems of the implantable device 110 to operate. In some embodiments, the program code is updateable via data communications through the communication subsystem 434, thereby enabling the implantable device 110 to be reprogrammed or modified as necessary for optimum patient treatment.

A fourth storage facility 516 within the memory subsystem 431 can include any patient-specific and device-specific settings used in the operation of the implantable device 110. The programmer 312 can be configured to generate these settings based on patient-specific considerations, including the nature of the disorder being treated, for example but without limitation, epilepsy, the locations of the electrodes and the types of sensors being used, and any other relevant factors.

The programmer 312 can be configured to programmed to generate these settings based on an analysis of the patient's EEG and other sensor data, which might have been acquired by and received from the implantable device 110 or by other means. Examples of patient-specific parameters would include detection settings (e.g., the amplitude threshold used to identify tremor, as described below with reference to FIGS. 10A-10D and stimulation settings (e.g., the frequency and amplitude of electrical stimulation applied in response to detected tremors). Many other parameters and settings are of course possible and will not be described in detail here, as they would be apparent to an individual of ordinary skill.

In some embodiments, the stimulation settings can be supplied to the autovariation module 440 so that the auto-adjust module 440 can automatically vary the course of therapy being provided according to settings input by the clinician. In use, the stimulation settings stored within the storage facility storing the Parameters and Settings 516 can be modified by the clinician or programmer. For example, a clinician can input data into the storage facility storing the Parameters and Settings 516 representing a schedule of parameter changes to be performed by the auto-adjust module 440. In an exemplary but non-limiting embodiment, such a schedule can be expressed as follows:

1) Day 1, 12:00 am, increase amplitude of responsive stimulation by 2%;
2) Day 1, 9:00 am, prompt patient for feedback;
3) Day 1, 12:00 pm, prompt patient for feedback;
4) Day 1, 6:00 pm, prompt patient for feedback;
5) Day 2, 12:00 am, increase amplitude of responsive stimulation by 2%;
6) Day 2, 9:00 am, prompt patient for feedback;
7) Day 2, 12:00 pm, prompt patient for feedback;
8) Day 2, 6:00 pm, prompt patient for feedback;
9) Day 3, 12:00 pm, increase amplitude of responsive stimulation by 4%;
10) Day 3, 12:30 pm, prompt patient for feedback;
11) Day 3, 6:00 pm, prompt patient for feedback; and
12) Day 3, 9:00 pm, prompt patient for feedback.

After such a schedule is completed, the clinician can review the stored feedback and, optionally, provide further adjustments to the device 110. For example, if the clinician is satisfied that one of the settings used during the schedule is optimal, the clinician can set the device 110 to use that setting for future therapy provided to the patient.

On the other hand, if the clinician determines that other parameter settings should be explored, the clinician can input a further schedule to the storage facility for the Parameters and Settings 516 and review the patient feedback resulting from this new schedule.

The memory subsystem 431 might also include various other types of data. It should be observed that the various data types described above are intended as illustrative and not comprehensive.

Figure 6:
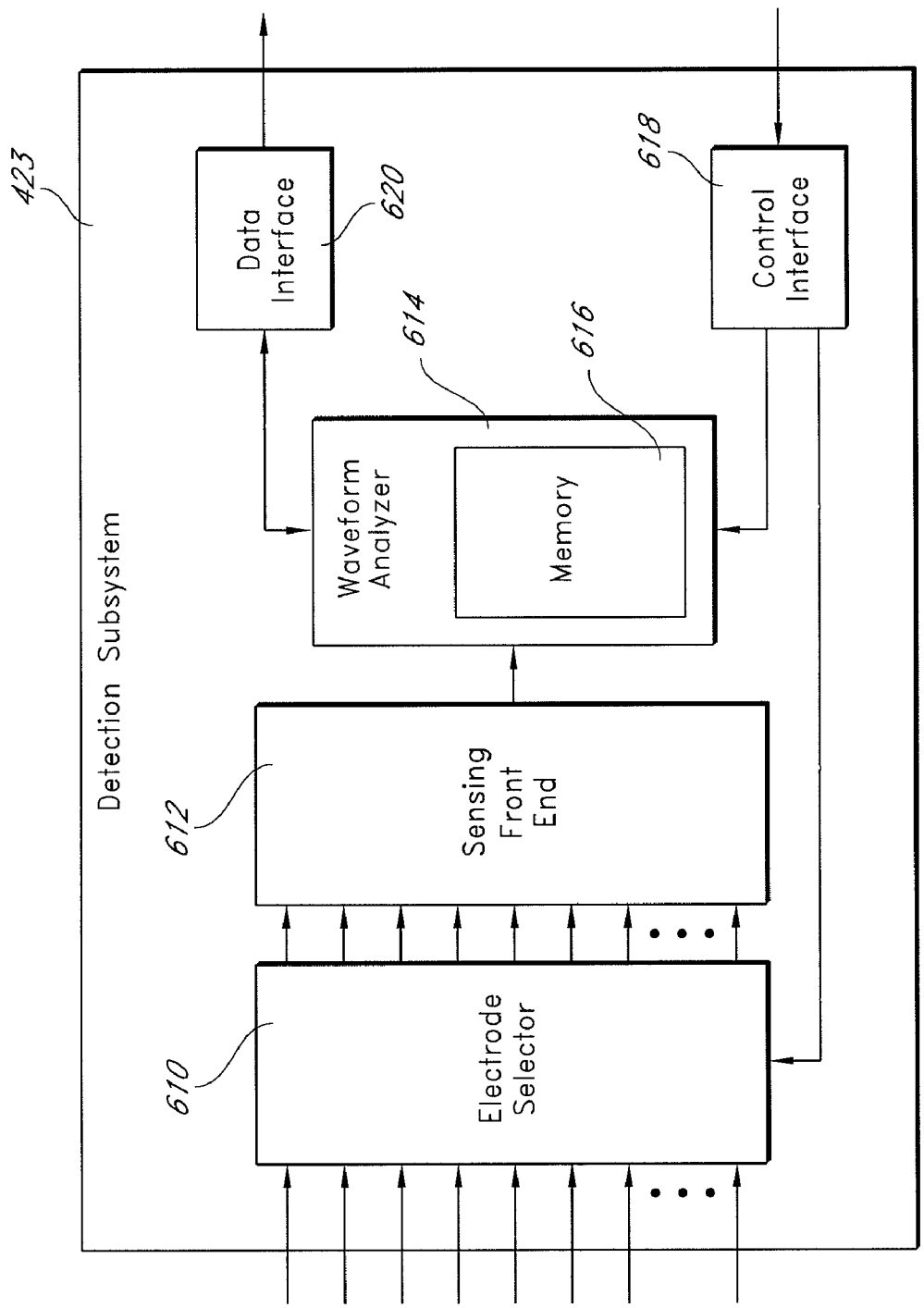
FIG. 6 is a block diagram illustrating the functional components of a detection subsystem of the implantable neurostimulator of FIG. 4.

FIG. 6 illustrates details of the detection subsystem 423 (FIG. 4). Inputs from the electrodes 412, 414, 416 and 418 are on the left, and connections to other subsystems are on the right.

With continued reference to FIGS. 4 and 6, signals received from the electrodes 412, 414, 416 and 418 (as routed through the electrode interface 420) are received in an electrode selector 610. The electrode selector 610 allows the device to select which electrodes should be routed to which individual sensing channels of the detection subsystem 423, based on commands received through a control interface 618 from the memory subsystem 431 or the CPU 432 (FIG. 4).

In some embodiments, each sensing channel of the detection subsystem 423 receives a bipolar signal representative of the difference in electrical potential between two selectable electrodes. Accordingly, the electrode selector 610 provides signals corresponding to each pair of selected electrodes to a sensing front end 612, which performs amplification, analog to digital conversion, and multiplexing functions on the signals in the sensing channels. The sensing front end is described further below in connection with FIG. 7. In some embodiments, where the device 110 only includes two electrodes (e.g., electrodes 412, 414), the electrode selector 610 can be eliminated, allowing the detection subsystem 423 to operate only on a single channel. This provides an advantage of further reducing the size of the overall device 110.

A multiplexed input signal representative of all active sensing channels can then be fed from the sensing front end 612 to a waveform analyzer 614. The waveform analyzer 614 is preferably a special-purpose digital signal processor (DSP) adapted for use with the embodiment, or in an alternative embodiment, can comprise a programmable general-purpose DSP.

In some embodiments, the waveform analyzer can have its own scratchpad memory area 616 used for local storage of data and program variables when signal processing is being performed. In either case, the signal processor performs suitable measurement and detection methods described generally above and in greater detail below. Any results from such methods, as well as any digitized signals intended for storage transmission to external equipment, are passed to various other subsystems of the control module 410, including the memory subsystem 431 and the CPU 432 (FIG. 4) through a data interface 620. Similarly, the control interface 618 allows the waveform analyzer 614 and the electrode selector 610 to be in communication with the CPU 432.

Figure 7:
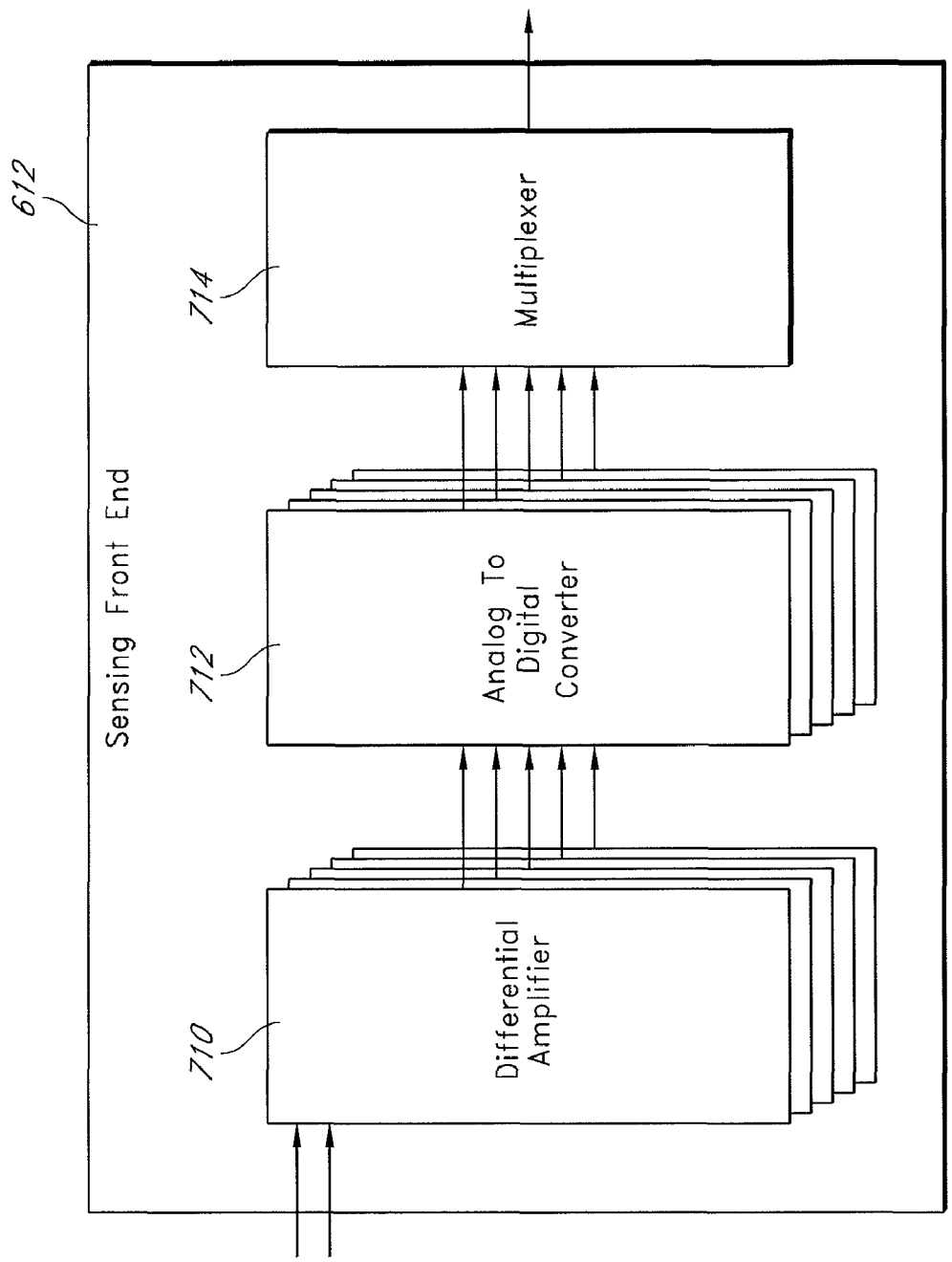
FIG. 7 is a block diagram illustrating the functional components of the sensing front end of the detection subsystem of FIG. 6.

With reference to FIG. 7, the sensing front end 612 (FIG. 6) is illustrated in further detail. As shown, the sensing front end includes a plurality of differential amplifier channels 710, each of which receives a selected pair of inputs from the electrode selector 610.

In some embodiments, each of the differential amplifier channels 710 is adapted to receive or to share inputs with one or more other differential amplifier channels 710 without adversely affecting the sensing and detection capabilities of the device 110 according to some embodiments. For clarity, only one channel is illustrated in FIG. 7, but it should be noted that any practical number of sensing channels can be employed in the device 110 according to some embodiments.

Each differential amplifier channel 710 feeds a corresponding analog to digital converter (ADC) 712. Preferably, the analog to digital converters 712 are separately programmable with respect to sample rates—in the disclosed embodiment, the ADCs 712 convert analog signals into 10-bit unsigned integer digital data streams at a sample rate selectable between 250 Hz and 500 Hz.

In several of the illustrations described below where waveforms are shown, sample rates of 250 Hz are typically used for simplicity. However, the embodiments disclosed herein shall not be deemed to be so limited, and numerous sample rate and resolution options are possible, with tradeoffs known to individuals of ordinary skill in the art of electronic signal processing. The resulting digital signals are received by a multiplexer 714 that creates a single interleaved digital data stream representative of the data from all active sensing channels. As described in further detail below, not all of the sensing channels need to be used at one time, and it can in fact be advantageous in certain circumstances to deactivate certain sensing channels to reduce the power consumed by the device 110 according to some embodiments.

It should be noted that as illustrated and described herein, a "sensing channel" is not necessarily a single physical or functional item that can be identified in any illustration. Rather, a sensing channel can be formed from the functional sequence of operations described herein, and particularly represents a single electrical signal received from any pair or combination of electrodes, as preprocessed by a device 110 according to some embodiments, in both analog and digital forms. See, e.g., U.S. Pat. No. 6,473,639, issued Oct. 29, 2002 to D. Fischell et al., filed on Mar. 2, 2000 and entitled "Neurological Event Detection Procedure Using Processed Display Channel Based Algorithms and Devices Incorporating These Procedures," which is hereby incorporated by reference as though set forth in full herein. At times (particularly after the multiplexer 714), multiple sensing channels are processed by the same physical and functional components of the system; notwithstanding that, it should be recognized that unless the description herein indicates to the contrary, a device 110 according to some embodiments processes, handles, and treats each sensing channel independently.

The interleaved digital data stream is passed from the multiplexer 714, out of the sensing front end 612, and into the waveform analyzer 614. The waveform analyzer 614 is illustrated in detail in FIG. 8.

An interleaved digital data stream representing information from all of the active sensing channels is first received by a channel controller 810. The channel controller applies information from the active sensing channels to a number of wave morphology analysis units 812 and window analysis units 814. It is preferred to have as many wave morphology analysis units 812 and window analysis units 814 as possible, consistent with the goals of efficiency, size, and low power consumption necessary for an implantable device. In some embodiments, there are sixteen wave morphology analysis units 812 and eight window analysis units 814, each of which can receive data from any of the sensing channels of the sensing front end 612, and each of which can be operated with different and independent parameters, including differing sample rates, as will be discussed in further detail below.

Further, in some embodiments, such as embodiments using only a single bipolar channel, the waveform analyzer 614 can operate with as little as one or two wave morphology analysis units 812 and one or two window analysis units 814, each of which can receive data from the single channel of the sensing front end 612, each of which can be operated with different and independent parameters, including different sampling rates. Reducing the number of wave morphology analysis units 812 and window analysis units 814 allows the recording device 110 to be further reduced in size.

Each of the wave morphology analysis units 812 can operate to extract certain feature information from an input waveform as described below in conjunction with FIGS. 10-12. Similarly, each of the window analysis units 814 can perform certain data reduction and signal analysis within time windows in the manner described in conjunction with FIGS. 13-18. Output data from the various wave morphology analysis units 812 and window analysis units 814 can be combined via event detector logic 816. The event detector logic 816 and the channel controller 810 can be controlled by control commands 818 received from the control interface 618 (FIG. 6).

A "detection channel," as the term is used herein, refers to a data stream including the active sensing front end 612 and the analysis units of the waveform analyzer 614 processing that data stream, in both analog and digital forms. It should be noted that each detection channel can receive data from a single sensing channel; each sensing channel preferably can be applied to the input of any combination of detection channels. The latter selection is accomplished by the channel controller 810. As with the sensing channels, not all detection channels need to be active; certain detection channels can be deactivated to save power or if additional detection processing is deemed unnecessary in certain applications.

In conjunction with the operation of the wave morphology analysis units 812 and the window analysis units 814, a scratchpad memory area 616 can be provided for temporary storage of processed data. The scratchpad memory area 616 can be physically part of the memory subsystem 431, or alternatively can be provided for the exclusive use of the waveform analyzer 614. Other subsystems and components of a system according to an embodiment can also be furnished with local scratchpad memory, if such a configuration is desired.

Figure 9:
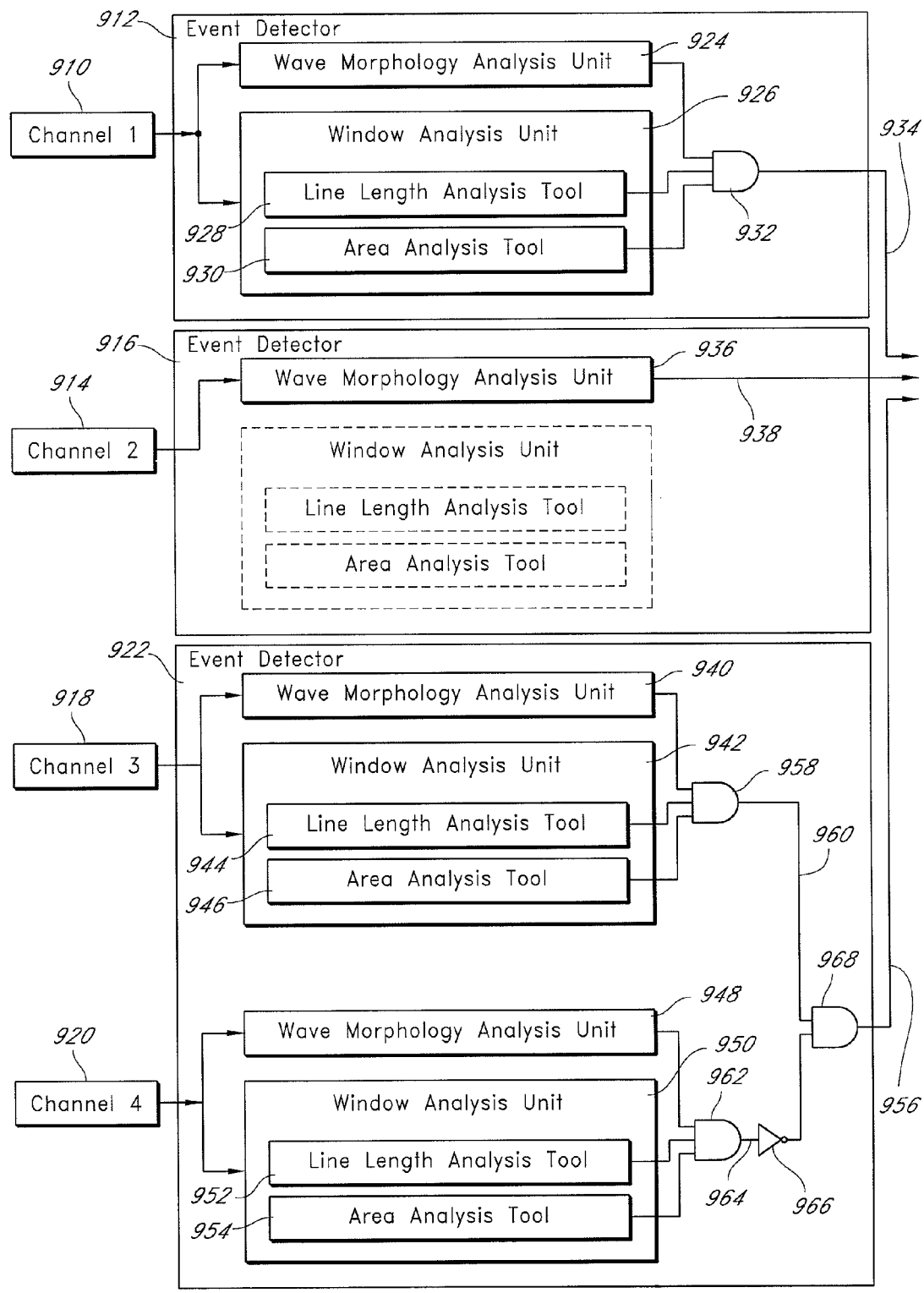
FIG. 9 is a block diagram illustrating the functional arrangement of components of the waveform analysis of the detection subsystem of FIG. 6 in one programmed embodiment.

An exemplary but non-limiting operation of the event detector logic 816 is illustrated in detail in the functional block diagram of FIG. 9, in which four exemplary sensing channels are analyzed by three illustrative event detectors.

A first sensing channel 910 provides input to a first event detector 912. While the first event detector 912 is illustrated as a functional block in the block diagram of FIG. 9, it should be recognized that it is a functional block only for purposes of illustration, and can not have any physical counterpart in a device according to some embodiments. Similarly, a second sensing channel 914 provides input to a second event detector 916, and a third input channel 918 and a fourth input channel 920 both provide input to a third event detector 922. Additionally, in embodiments using only a single channel, either one of the event detectors 912, 916, described below in greater detail, can be used. However, other configurations can also be used.

Figure 8:
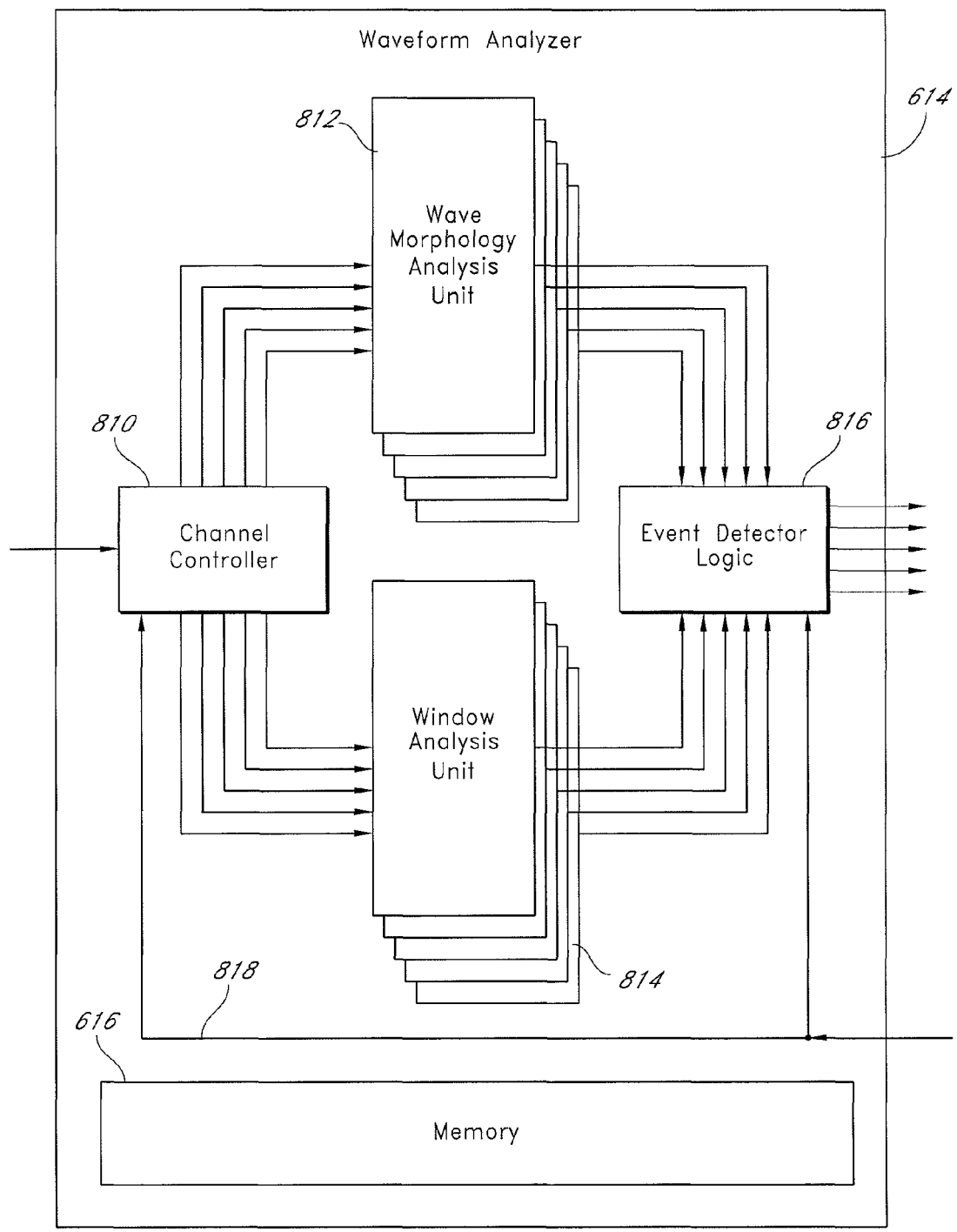
FIG. 8 is a block diagram illustrating the functional components of a waveform analyzer of the detection subsystem of FIG. 6.

Considering the processing performed by the event detectors 912, 916, and 922, the first input channel 910 feeds a signal to both a wave morphology analysis unit 924 (one of the wave morphology analysis units 812 of FIG. 8) and a window analysis unit 926 (one of the window analysis units 814 of FIG. 8). The window analysis unit 926, in turn, includes a line length analysis tool 928 and an area analysis tool 930. As discussed in detail below, the line length analysis tool 928 and the area analysis tool 930 can be configured to analyze different aspects of the signal from the first input channel 910.

Outputs from the wave morphology analysis unit 924, the line length analysis tool 928, and the area analysis tool 930 can be combined in a Boolean AND operation 932 and sent to an output 934 for further use by a system according to an embodiment. For example, if a combination of analysis tools in an event detector identifies several simultaneous (or near-simultaneous) types of activity in an input channel, a system according to an embodiment can be programmed to perform an action in response thereto. Exemplary details of the analysis tools and the combination processes that can be used in the event detectors are described in greater detail below.

In the second event detector 916, only a wave morphology analysis unit 936 is active. Accordingly, no Boolean operation needs to be performed, and the wave morphology analysis unit 936 directly feeds an event detector output 938.

The third event detector 922 can operate on two input channels 918 and 920, and can include two separate detection channels of analysis units: a first wave morphology analysis unit 940 and a first window analysis unit 942, the latter including a first line length analysis tool 944 and a first area analysis tool 946; and a second wave morphology analysis unit 948 and a second window analysis unit 950, the latter including a second line length analysis tool 952 and a second area analysis tool 954. The two detection channels of analysis units can be combined to provide a single event detector output 956.

In the first detection channel of analysis units 940 and 942, outputs from the first wave morphology analysis unit 940, the first line length analysis tool 944, and the first area analysis tool 946 can be combined via a Boolean AND operation 958 into a first detection channel output 960. Similarly, in the second detection channel of analysis units 948 and 950, outputs from the second wave morphology analysis unit 948, the second line length analysis tool 952, and the second area analysis tool 954 can be combined via a Boolean AND operation 962 into a second detection channel output 964. In the illustrated embodiment, the second detection channel output 964 is invertible with selectable Boolean logic inversion 966 before it is combined with the first detection channel output 960. Subsequently, the first detection channel output 960 and the second detection channel output 964 are combined with a Boolean AND operation 968 to provide a signal to the output 956. In an alternative embodiment, a Boolean OR operation is used to combine the first detection channel output 960 and the second detection channel output 964.

In some embodiments, the second detection channel (analysis units 948 and 950) of the third event detector 922 represents a "qualifying channel" with respect to the first detection channel (analysis units 940 and 942). In general, a qualifying channel allows a detection to be made only when both channels are in concurrence with regard to detection of an event. For example, a qualifying channel can be used to indicate when a seizure has "generalized," i.e. spread through a significant portion of a patient's brain. To do this, the third input channel 918 and the fourth input channel 920 can be configured to receive EEG waveforms from separate amplifier channels coupled to electrodes in separate parts of the patient's brain (e.g., in opposite hemispheres). Accordingly, then, the Boolean AND operation 968 will indicate a detection only when the first detection output 960 and the second detection output 964 both indicate the presence of an event (or, when Boolean logic inversion 966 is present, when the first detection output 960 indicates the presence of an event while the second detection output 964 does not). As described in further detail below, the detection outputs 960 and 964 can be provided with selectable persistence (i.e., the ability to remain triggered for some time after the event is detected), allowing the Boolean AND combination 968 to be satisfied even when there is not precise temporal synchronization between detections on the two channels.

It should be appreciated that the concept of a "qualifying channel" allows the flexible configuration of a device 110 to achieve a number of advantageous results. In addition to the detection of generalization, as described above, a qualifying channel can be configured, for example, to detect noise so a detection output is valid only when noise is not present, to assist in device configuration in determining which of two sets of detection parameters is preferable (by setting up the different parameters in the first detection channel and the second detection channel, then replacing the Boolean AND combination with a Boolean OR combination), or to require a specific temporal sequence of detections (which would be achieved in software by the CPU 432 after a Boolean OR combination of detections). There are numerous other possibilities.

The outputs 934, 938, and 956 of the event detectors are preferably represented by Boolean flags, and as described below, provide information for the operation of a system according to an embodiment.

While FIG. 9 illustrates four different sensing channels providing input to four separate detection channels, it should be noted that maximally flexible embodiments would allow each sensing channel to be connected to one or more detection channels. It can be advantageous to program the different detection channels with different settings (e.g., thresholds) to facilitate alternate "views" of the same sensing channel data stream.

Figure 10A:
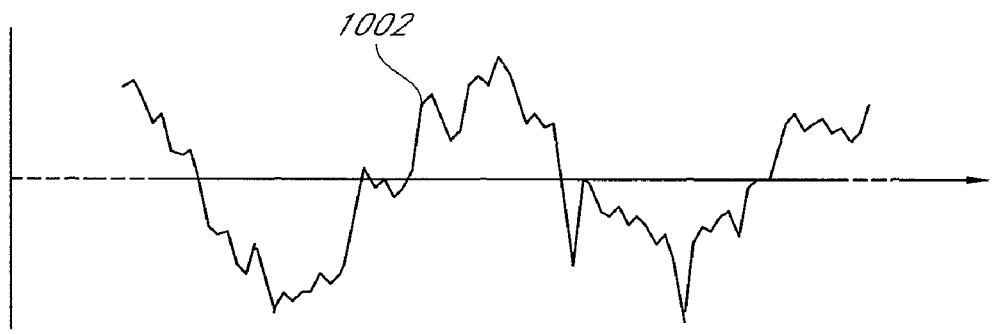
FIG. 10A is a graph of an exemplary unfiltered EEG signal.
Figure 10B:
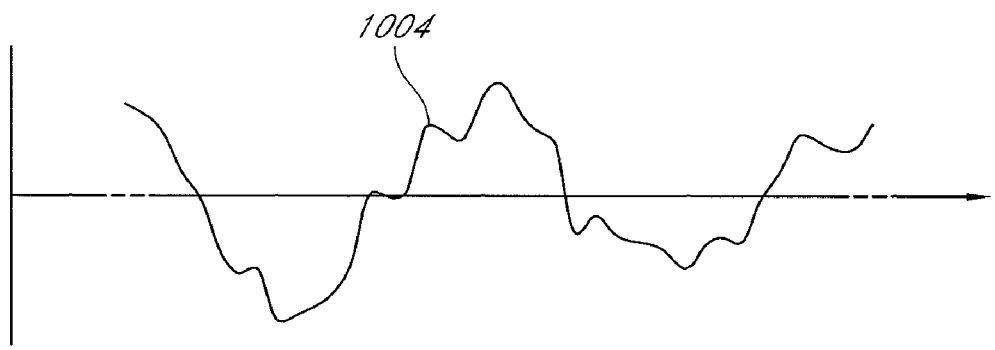
FIG. 10B is a graph of a filtered version of the unfiltered signal of FIG. 10A.
Figure 10C:
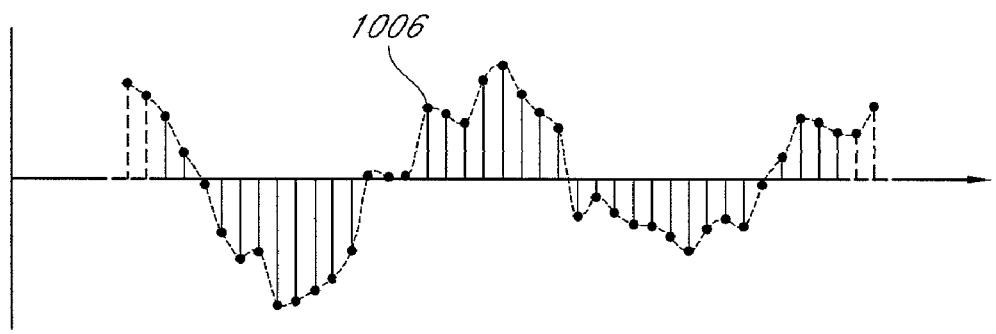
FIG. 10C is another graph of the filtered signal of FIG. 10B, with annotations showing how the signal might be subdivided by sampling windows.

FIGS. 10A, 10B, and 10C illustrate three representative waveforms of the type expected to be manipulated by a device 110 according to some embodiments. It should be noted, however, that the waveforms illustrated in FIGS. 10A, 10B, and 10C are illustrative only, and are not intended to represent any actual data.

With reference to FIG. 10A, the first waveform 1002 is representative of an unprocessed electroencephalogram (EEG) or electrocorticogram (ECoG) waveform having a substantial amount of variability; the illustrated segment has a duration of approximately 160 ms and a dominant frequency (visible as the large-scale crests and valleys) of approximately 12.5 Hz. It will be recognized that the first waveform 1002 is rather rough and peaky; there is a substantial amount of high frequency energy represented therein.

The second waveform 1004, as shown in FIG. 10B, represents a filtered version of the original EEG waveform 1002. As shown, most of the high frequency energy has been eliminated from the signal, and the second waveform 1004 is significantly smoother. In the disclosed embodiment, this filtering operation is performed in the sensing front end 612 before the analog to digital converters 712 (FIG. 7).

The filtered waveform 1004 can then be sampled by one of the analog to digital converters 712; this operation is represented graphically in FIG. 10C, as the third waveform 1006. As illustrated, a sample rate used in some embodiments is 250 Hz (4 ms sample duration), resulting in approximately 40 samples over the illustrated 160 ms segment. As is well known in the art of digital signal processing, the amplitude resolution of each sample is limited; in some embodiments, each sample is measured with a resolution of 10 bits (or 1024 possible values). As is apparent upon visual analysis of the third waveform 1004, the dominant frequency component has a wavelength of approximately 20 samples, which corresponds to the dominant frequency of 12.5 Hz.

Figure 10D:
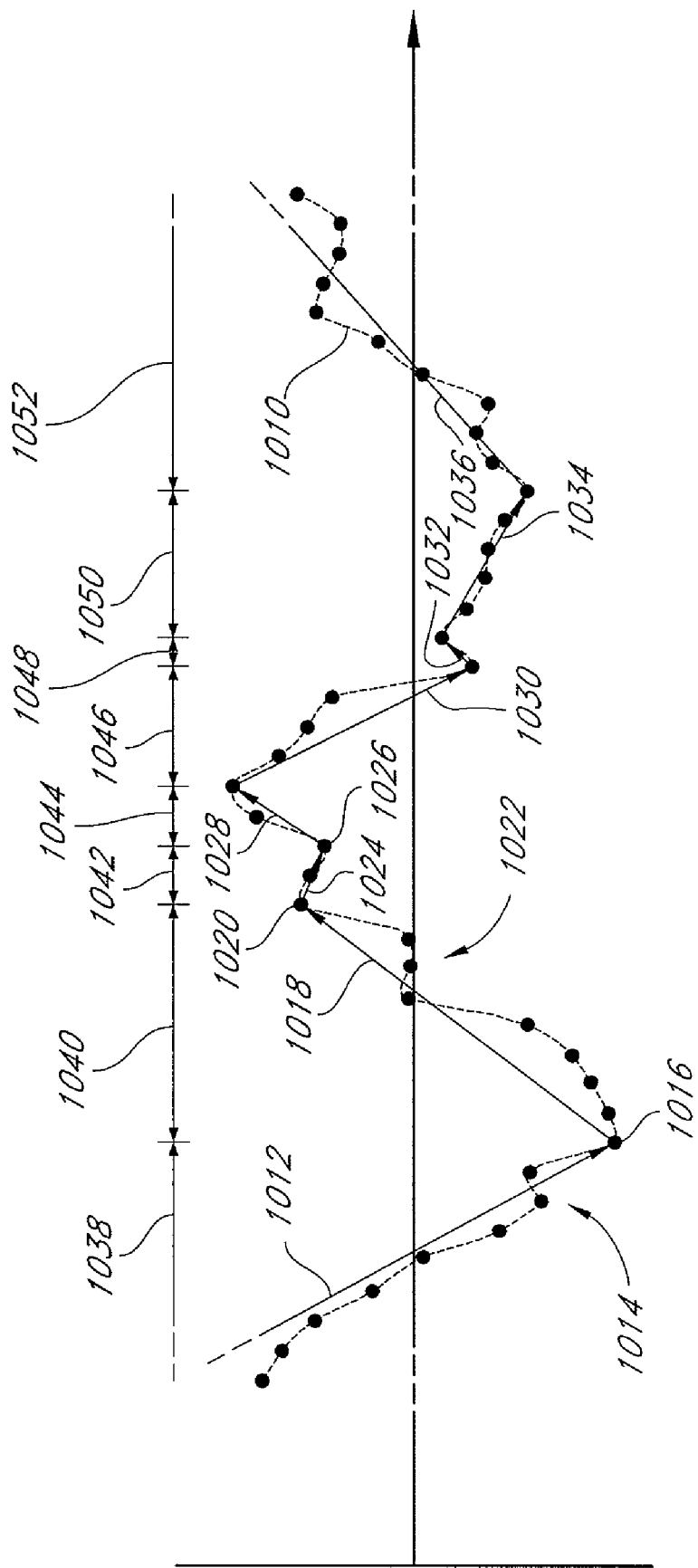
FIG. 10D is a graph of the subdivided signal of FIG. 10C with additional annotations illustrating how half waves might be defined in or extracted from the signal.

Referring now to FIG. 10D, the processing of the wave morphology analysis units 812 is described in conjunction with a filtered and sampled waveform 1010 of the type illustrated as the third waveform 1006 of FIG. 10C.

In a first half wave 1012, which is partially illustrated in FIG. 10D (the starting point occurs before the illustrated waveform segment 1010 begins), the waveform segment 1010 is essentially monotonically decreasing, except for a small first perturbation 1014. Accordingly, the first half wave 1012 is represented by a vector from the starting point (not shown) to a first local extremum 1016, where the waveform starts to move in the opposite direction. The first perturbation 1014 is of insufficient amplitude to be considered a local extremum, and is disregarded by a hysteresis mechanism (discussed in further detail below).

A second half wave 1018 extends between the first local extremum 1016 and a second local extremum 1020. Again, a second perturbation 1022 is of insufficient amplitude to be considered an extremum. Likewise, a third half wave 1024 extends between the second local extremum 1020 and a third local extremum 1026; this can appear to be a small perturbation, but is greater in amplitude than a selected hysteresis threshold. The remaining half waves 1028, 1030, 1032, 1034, and 1036 are identified analogously. As will be discussed in further detail below, each of the identified half waves 1012, 1018, 1024, 1028, 1030, 1032, 1034, and 1036 has a corresponding duration 1038, 1040, 1042, 1044, 1046, 1048, 1050, and 1052, respectively, and analogously, a corresponding amplitude determined from the relative positions of each half wave's starting point and ending point along the vertical axis, and a slope direction, increasing or decreasing.

In a method performed according to some embodiments, it is particularly advantageous to allow for a programmable hysteresis setting in identifying the ends of half waves. In other words, as explained above, the end of an increasing or decreasing half wave might be prematurely identified as a result of quantization (and other) noise, low-amplitude signal components, and other perturbing factors, unless a small hysteresis allowance is made before a reversal of waveform direction (and a corresponding half wave end) is identified. Hysteresis allows for insignificant variations in signal level inconsistent with the signal's overall movement to be ignored without the need for extensive further signal processing such as filtering. Without hysteresis, such small and insignificant variations might lead to substantial and gross changes in where half waves are identified, leading to unpredictable results.

Figure 11:
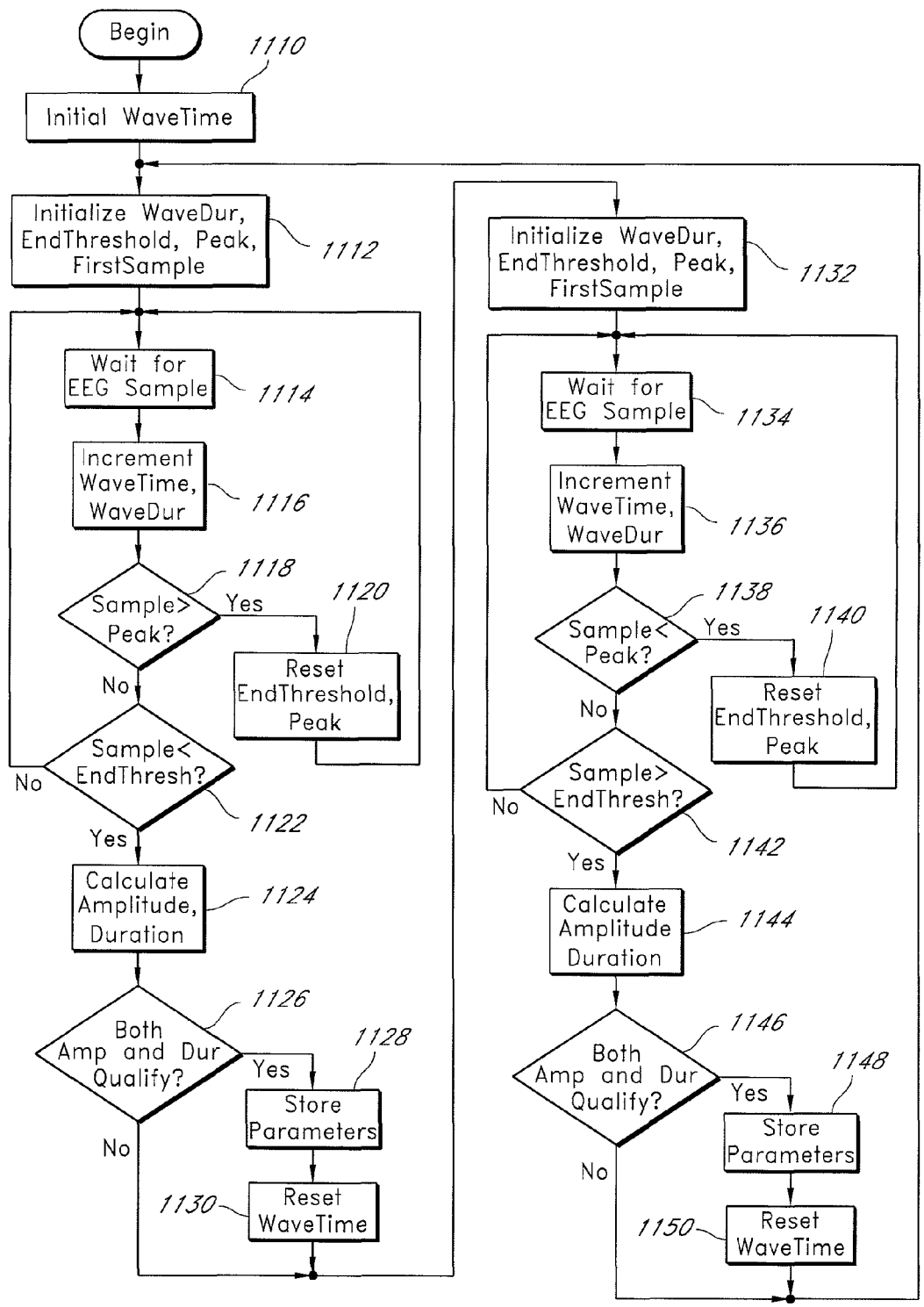
FIG. 11 is a flow chart illustrating the process performed by functional components of the waveform analyzer of FIG. 8 in extracting half waves as illustrated in FIG. 10D.

The processing steps performed with regard to the waveform 1010 and half waves of FIG. 10D are set forth in FIG. 11. The method begins by identifying an increasing half wave (with an ending amplitude higher than the starting amplitude, as in the second half wave 1018 of FIG. 10D). To do this, a variable corresponding to half wave time is first initialized to zero (step 1110); then half wave duration, ending threshold, peak amplitude, and first sample value are all initialized (step 1112). Specifically, the half wave duration value is set to zero; the peak amplitude and first sample values are set to the amplitude value of the last observed sample, which as described above is a value having 10-bit precision; and the ending threshold is set to the last observed sample minus a small preset hysteresis value. After waiting for a measurement of the current EEG sample (step 1114), the half wave time and half wave duration variables are incremented (step 1116). If the current EEG sample has an amplitude greater than the peak amplitude (step 1118), then the amplitude of the half wave is increasing (or continues to increase). Accordingly, the ending threshold is reset to be the current EEG sample's amplitude minus the hysteresis value, and the peak is reset to the current EEG sample's amplitude (step 1120), and the next sample is awaited (step 1114).

If the current EEG sample has an amplitude less than the ending threshold (step 1122), then the hysteresis value has been exceeded, and a local extremum has been identified. Accordingly, the end of the increasing half wave has been reached, and the amplitude and duration of the half wave are calculated (step 1124). The amplitude is equal to the peak amplitude minus the first sample value; the duration is equal to the current half wave duration. Otherwise, the next ample is awaited (step 1114).

If both the amplitude and the duration qualify by exceeding corresponding preset thresholds (step 1126), then the amplitude, duration, half wave time, half wave direction (increasing) are stored in a buffer (step 1128), and the half wave time is reset to zero (step 1130).

At the conclusion of the increasing half wave, the process continues by initializing wave duration, the ending threshold, the peak amplitude, and the first sample value (step 1132). Wave duration is set to zero, the ending threshold is set to the last sample value plus the hysteresis value, the peak amplitude and the first sample value are set to the most recent sample value.

After waiting for a measurement of the current EEG sample (step 1134), the half wave time and half wave duration variables are incremented (step 1136). If the current EEG sample has an amplitude lower than the peak amplitude (step 1138), then the amplitude of the half wave is decreasing (or continues to decrease). Accordingly, the ending threshold is reset to be the current EEG sample's amplitude plus the hysteresis value, the peak is reset to the current EEG sample's amplitude (step 1140), and the next sample is awaited (step 1134).

If the current EEG sample has an amplitude greater than the ending threshold (step 1142), then the hysteresis value has been exceeded, and a local extremum has been identified. Accordingly, the end of the decreasing half wave has been reached, and the amplitude and duration of the half wave are calculated (step 1144). The amplitude is equal to the first sample value minus the peak amplitude, and the duration is equal to the current half wave duration. Otherwise, the next EEG sample is awaited (step 1134).

If both the amplitude and the duration qualify by exceeding corresponding preset thresholds (step 1146), then the amplitude, duration, half wave time, half wave direction (decreasing) are stored in a buffer (step 1148), and the half wave time is reset to zero (step 1150). It should be noted that, in the context of this specification, the term "exceed" in regard to a threshold value means to meet a specified criterion. Generally, to exceed a threshold herein is to have a numeric value greater than or equal to the threshold, although other interpretations (such as greater than, or less than, or less than or equal to, depending on the context) can be applicable.

At the conclusion of the decreasing half wave, further half waves are then identified by repeating the process from step 1112. As half wave detection is an ongoing and continuous process, this procedure preferably does not exit, but can be suspended from time to time when conditions or device state call for it, e.g. when the device is inactive. Once suspended, the procedure should recommence with the first initialization step 1110.

Accordingly, the process depicted in FIG. 11 stores parameters corresponding to qualified half waves, including their directions, durations, amplitudes, and the elapsed time between adjacent qualified half waves (i.e. the half wave time variable). In some embodiments, to reduce power consumption, this procedure is performed in custom electronic hardware; it should be clear that the operations of FIG. 11 can be performed in parallel for each active instance of the wave morphology analysis units 812 (FIG. 8). It should also be noted, however, that certain software can also be used to advantageous effect in this context.

Figure 12:
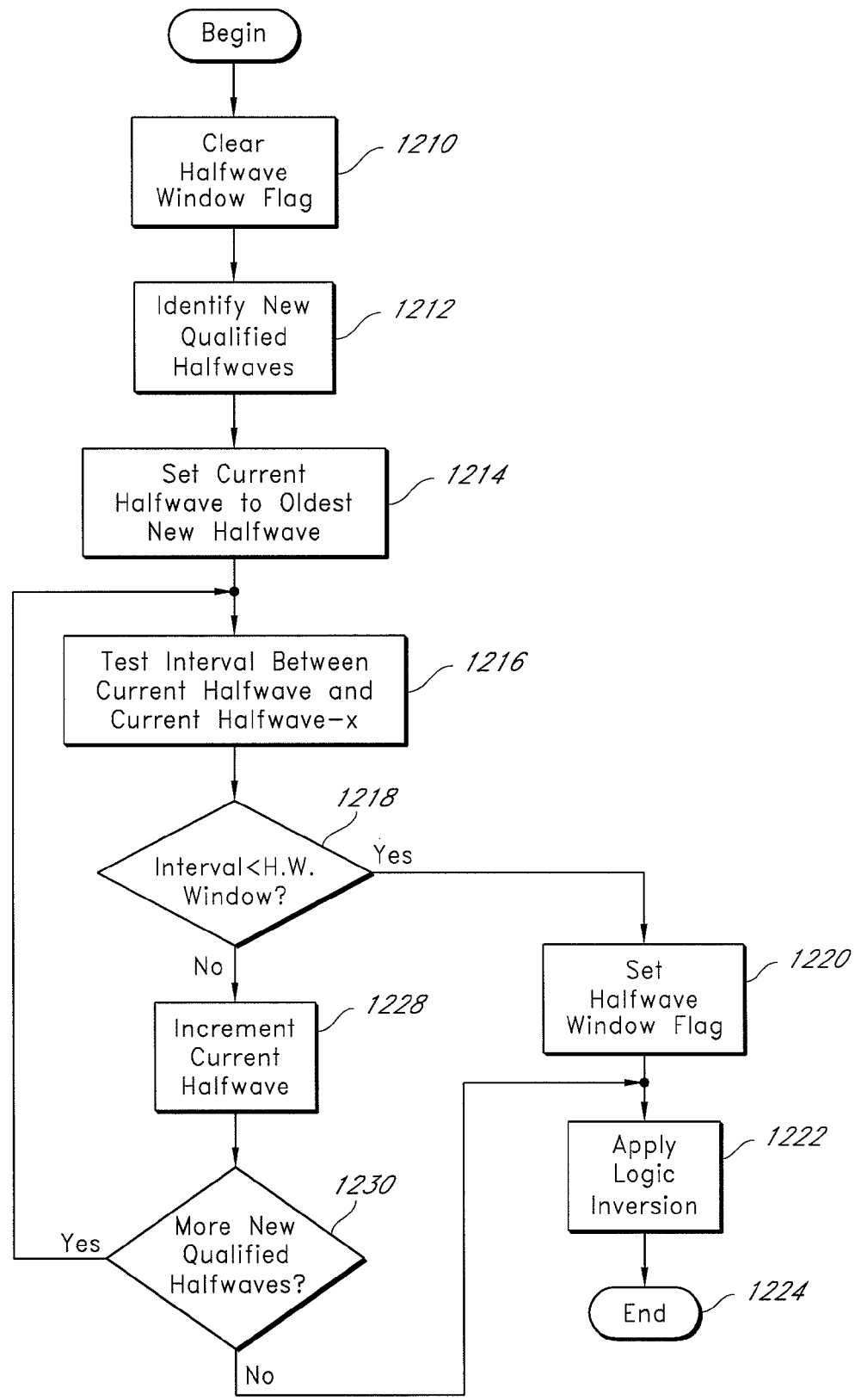
FIG. 12 is a flow chart illustrating the process performed by a central processing unit of the implantable neurostimulator of FIG. 4 in extracting and analyzing half waves from an EEG signal.

This stored information is used in the software process illustrated in FIG. 12, which is performed on a periodic basis, preferably once every processing window (a recurring time interval that is either fixed or programmable) by a system according to some embodiments. Consistent with the other analysis tools described herein, the duration of an exemplary processing window is in one embodiment, 128 ms, which corresponds to 32 samples at a 250 Hz sampling rate.

Each time the software process of FIG. 12 is invoked, the half wave window flag is first cleared (step 1210). Any qualified half waves identified by the process set forth in FIG. 11 that are newly identified since the last invocation of the procedure (i.e., all qualified half waves that ended within the preceding processing window) are identified (step 1212). A "current half wave" pointer is set to point to the oldest qualified half wave identified in the most recent processing window (step 1214). The time interval between the current half wave and the prior x half waves is then measured (step 1216), where x is a specified minimum number of half waves (preferably a programmable value) to be identified within a selected half wave time window (the duration of which is another programmable value) to result in the possible detection of a neurological event. If the time interval is less than the duration of the half wave time window (step 1218), then the half wave window flag is set (step 1220), logic inversion is selectively applied (step 1222), and the procedure ends (step 1224). Logic inversion, a mechanism for determining whether an analysis unit is triggered by the presence or absence of a condition, is explained in greater detail below. Otherwise, the current half wave pointer is incremented to point to the next new half wave (step 1228), and if there are no more new half waves (step 1230), logic inversion is applied if desired (step 1222), and the procedure ends (step 1224). Otherwise, the next time interval is tested (step 1216) and the process continues from there.

Logic inversion allows the output flag for the wave morphology analysis unit (or any other analyzer) to be selectively inverted. If logic inversion is configured to be applied to an output of a particular analysis unit, then the corresponding flag will be clear when the detection criterion (e.g., number of qualified half waves) is met, and set when the detection criterion is not met. This capability provides some additional flexibility in configuration, facilitating detection of the absence of certain signal characteristics when, for example, the presence of those characteristics is the norm.

Figure 13:
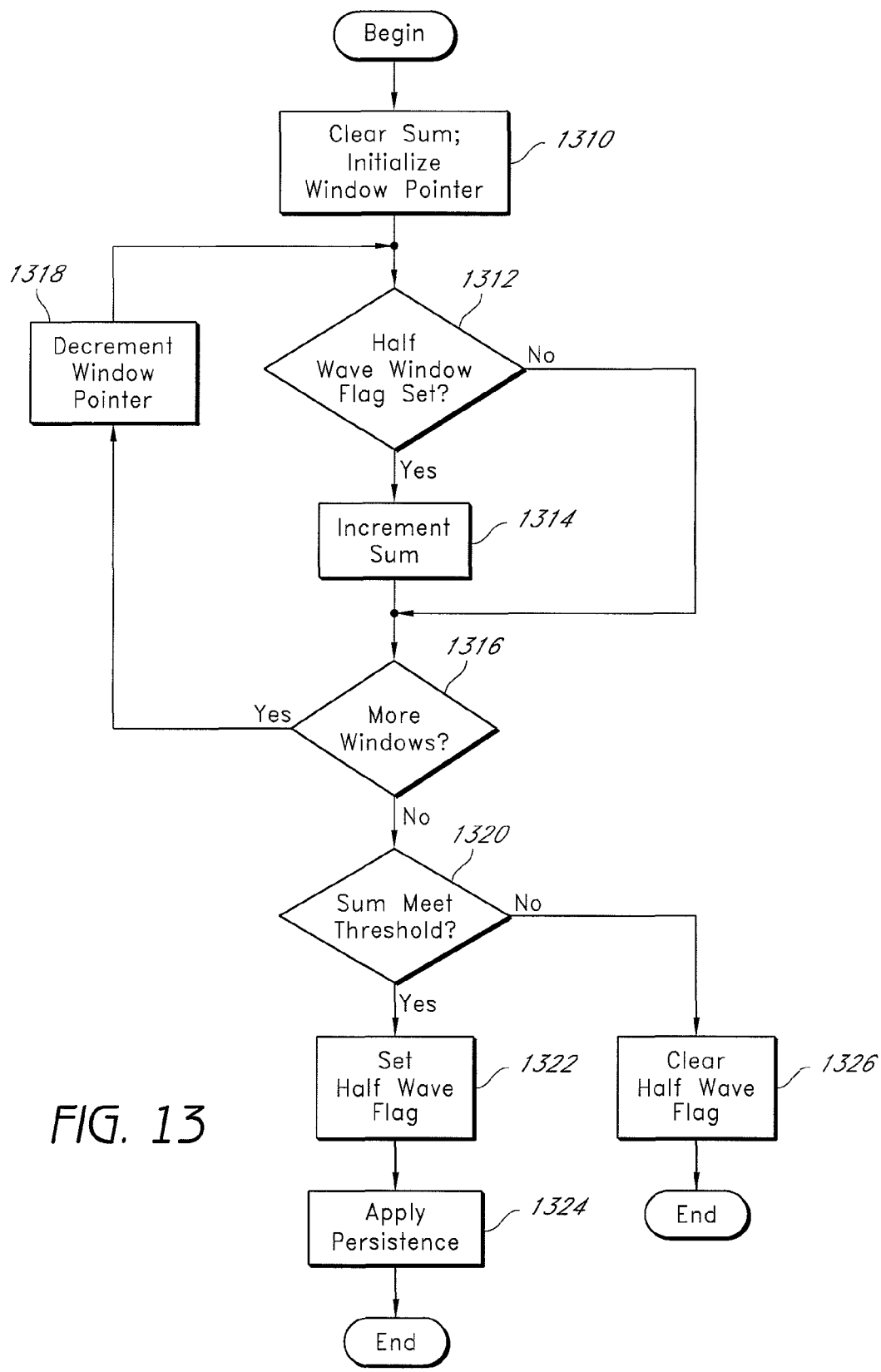
FIG. 13 is a flow chart illustrating the process performed by the central processing unit in the application of an X of Y criterion to half wave windows.

In some embodiments, the half wave window flag (set in step 1220) indicates whether a sufficient number of qualified half waves occur over an interval ending in the most recent processing window. To reduce the occurrence of spurious detections, an X-of-Y criterion is applied, causing the wave morphology analysis unit to trigger only if a sufficient number of qualified half waves occur in X of the Y most recent processing windows, where X and Y are parameters individually adjustable for each analysis tool. This process is illustrated in FIG. 13.

Initially, a sum (representing recent processing windows having the half wave window flag set) is cleared to zero and a current window pointer is initialized to point to the most recent processing window (step 1310). If the half wave window flag corresponding to the current window pointer is set (step 1312), then the sum is incremented (step 1314). If there are more processing windows to examine (for an X-of-Y criterion, a total of Y processing windows, including the most recent, should be considered) (step 1316), then the window pointer is decremented (step 1318) and the flag testing and sum incrementing steps (steps 1312-1314) are repeated.

After Y windows have been considered, if the sum of windows having set half wave window flags meets the threshold X (step 1320), then the half wave analysis flag is set (step 1322), persistence (described below) is applied (step 1324), and the procedure is complete. Otherwise, the half wave analysis flag is cleared (step 1326).

Persistence, another per-analysis-tool setting, allows the effect of an event detection (a flag set) to persist beyond the end of the detection window in which the event occurs. In some embodiments, persistence can be set anywhere from one second to fifteen seconds (though other settings are possible), so if detections with multiple analysis tools do not all occur simultaneously (though they should still occur within a fairly short time period), a Boolean combination of flags will still yield positive results. Persistence can also be used with a single analysis tool to smooth the results.

When the process of FIG. 13 is completed, the half wave analysis flag (set or cleared in steps 1322 and 1326, respectively) indicates whether an event has been detected in the corresponding channel of the wave morphology analysis units 712, or stated another way, whether a sufficient number of qualified half waves have appeared in X of the Y most recent processing windows. Although in the disclosed embodiment, the steps of FIGS. 12 and 13 are performed in software, it should be recognized that some or all of those steps can be performed using custom electronics, if it proves advantageous in the desired application to use such a configuration.

Figure 14:
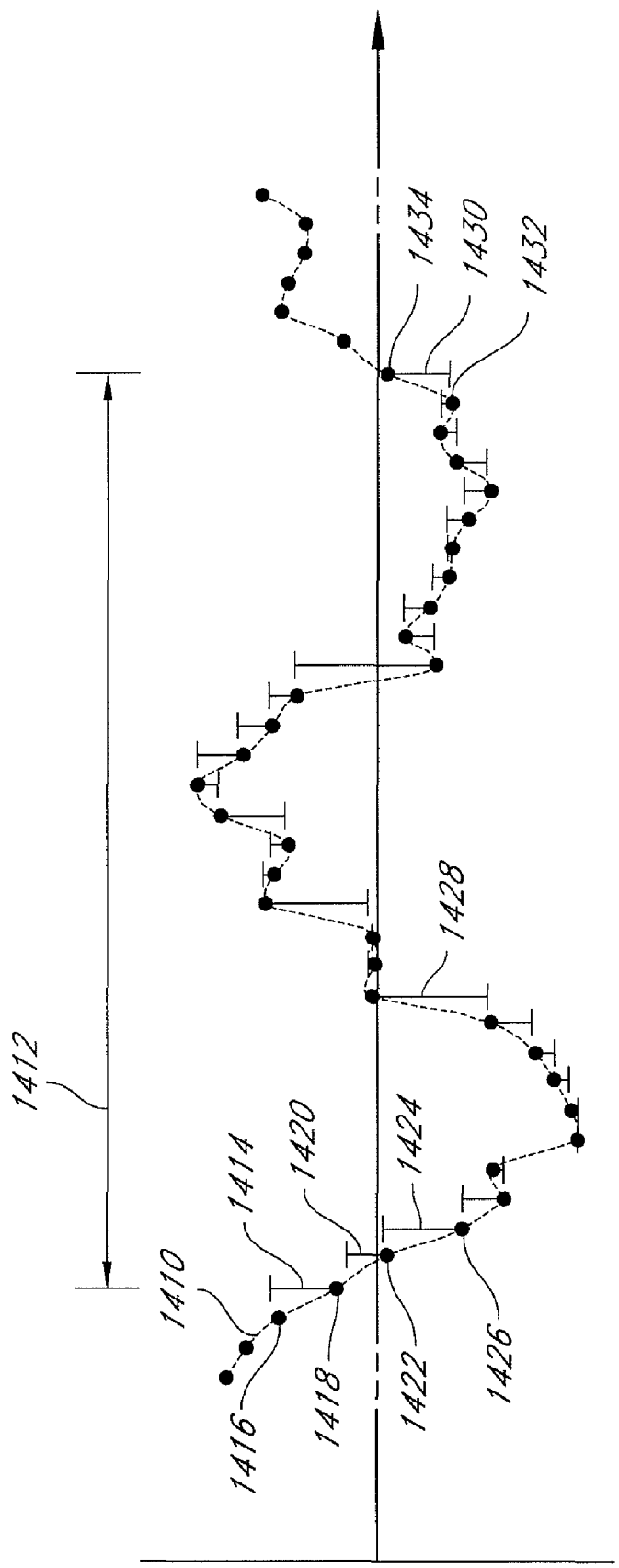
FIG. 14 is a graph of the exemplary EEG signal of FIG. 10A, after some filtering has been applied to it, and illustrating how a line length function can be calculated.

FIG. 14 illustrates the waveform of FIG. 10D, further depicting line lengths identified within a time window. The time window used with respect to FIGS. 14-16 can be different from the half wave processing window described above in connection with FIGS. 12-13, but in some embodiments, refers to the same time intervals. From an implementation standpoint, a single device interrupt upon the conclusion of each processing window allows all of the analysis tools to perform the necessary corresponding software processes; the line length analysis process of FIG. 16 (described below) is one such example. A waveform 1410 is a filtered and otherwise preprocessed EEG signal as received in one of the window analysis units 814 from the sensing front end 612. As discussed above, line lengths are considered within time windows. As illustrated in FIG. 14, the duration of an exemplary window 1412 is 32 samples, which is equivalent to 128 ms at a 250 Hz sampling rate.

The total line length for the window 1412 is the sum of the sample-to-sample amplitude differences within that window 1412. For example, the first contribution to the line length within the window 1412 is a first amplitude difference 1414 between a previous sample 1416 occurring immediately before the window 1412 and a first sample 1418 occurring within the window 1412. The next contribution comes from a second amplitude difference 1420 between the first sample 1418 and a second sample 1422; a further contribution 1424 comes from a third amplitude difference between the second sample 1422 and a third sample 1426; and so on. At the end of the window 1412, the final contribution to the line length comes from a last amplitude difference 1430 between a second-last sample 1432 in the window 1412 and a last sample 1434 in the window 1412. Note that all line lengths, whether increasing or decreasing in direction, are accumulated as positive values; accordingly, a decreasing amplitude difference 1414 and an increasing amplitude difference 1428 both contribute to a greater line length.

As illustrated herein, and as discussed in detail above, there are thirty-two samples within the window 1412. The illustrated window 1412 has a duration of 128 ms, and accordingly, the illustrated sample rate is 250 Hz. It should be noted, however, that alternate window durations and sample rates are possible and considered to be appropriate for some embodiments.

Figure 15:
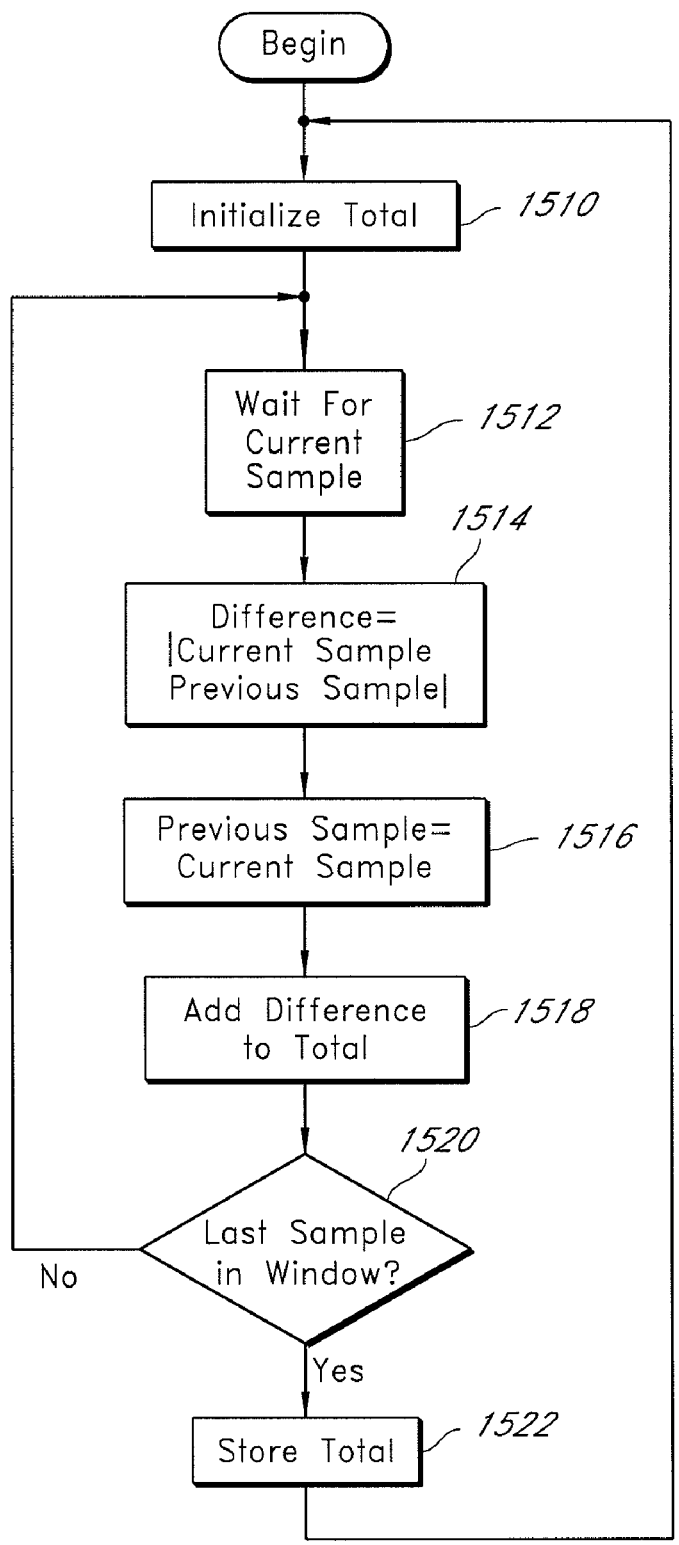
FIG. 15 is a flow chart illustrating a process performed by functional components of the waveform analyzer of FIG. 8 in calculating the line length function as illustrated in FIG. 14.

The line lengths illustrated in FIG. 14 can be calculated as shown by the flow chart of FIG. 15, which is invoked at the beginning of a time window. Initially, a line length total variable is initialized to zero (step 1510). The current sample is awaited (step 1512), and the absolute value of the amplitude difference between the current sample and the previous sample (which, when considering the first sample in a window, can come from the last sample in a previous window) is measured (step 1514).

In various alternative embodiments, either the measured difference (as calculated in step 1514, described above), or the sample values used to calculate the difference can be mathematically transformed in useful nonlinear ways. For example, it can be advantageous in certain circumstances to calculate the difference between adjacent samples using the squares of the sample values, or to calculate the square of the difference between sample values, or both. It is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 110.

For use in the next iteration, the previous sample is replaced with the value of the current sample (step 1516), and the calculated absolute value is added to the total (step 1518). If there are more samples remaining in the window 1412 (step 1520), another current sample is awaited (step 1512) and the process continues. Otherwise, the line length calculation for the window 1412 is complete, and the total is stored (step 1522), the total is re-initialized to zero (step 1510), and the process continues.

As with the half wave analysis method set forth above, the line length calculation does not need to terminate; it can be free-running yet interruptible. If the line length calculation is restarted after having been suspended, it should be re-initialized and restarted at the beginning of a window. This synchronization can be accomplished through hardware interrupts.

Figure 16:
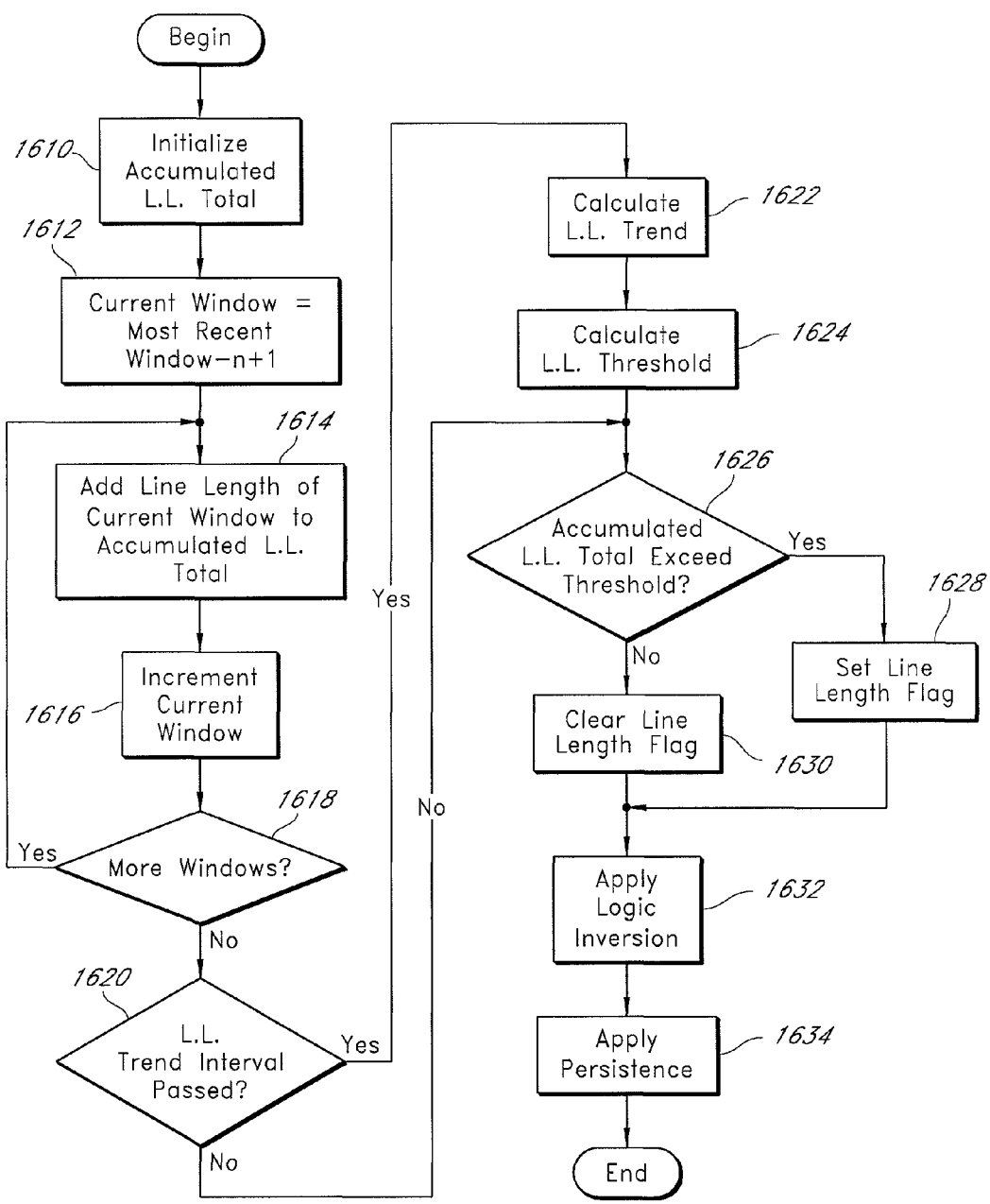
FIG. 16 is a flow chart illustrating a process performed by the central processing unit in calculating and analyzing a line length function of an EEG signal.

The line lengths calculated as shown in FIG. 15 are then processed as indicated in the flow chart of FIG. 16, which is performed after each window 1412 is calculated and stored (step 1522).

The process begins by calculating a running accumulated line length total over a period of n time windows. Where n>1, the effect is that of a sliding window; in an alternative embodiment an actual sliding window processing methodology can be used. First, the accumulated total is initialized to zero (step 1610). A current window pointer is set to indicate the $n^{th}$-last window, i.e., the window (n−1) windows before the most recent window (step 1612). The line length of the current window is added to the total (step 1614), the current window pointer is incremented (step 1616), and if there are more windows between the current window pointer and the most recent (last) window (step 1618), the adding and incrementing steps (1614-1616) are repeated. Accordingly, by this process, the resulting total includes the line lengths for each of the n most recent windows.

In some embodiments, the accumulated total line length is compared to a dynamic threshold, which is based on a trend of recently observed line lengths. The trend is recalculated regularly and periodically, after each recurring line length trend interval (which is preferably a fixed or programmed time interval). Each time the line length trend interval passes (step 1620), the line length trend is calculated or updated (step 1622). In some embodiments, this is accomplished by calculating a normalized moving average of several trend samples, each of which represents several consecutive windows of line lengths. A new trend sample is taken and the moving average is recalculated upon every line length trend interval. The number of trend samples used in the normalized moving average and the number of consecutive windows of line length measurements per trend sample are preferably both fixed or programmable values.

After the line length trend has been calculated, the line length threshold is calculated (step 1624) based on the new line length trend. In some embodiments, the threshold can be set as either a percentage of the line length trend (either below 100% for a threshold that is lower than the trend, or above 100% for a threshold that is higher than the trend) or alternatively a fixed numeric offset from the line length trend (either negative for a threshold that is lower than the trend, or positive for a threshold that is higher than the trend). Other methods for deriving a numeric threshold from a numeric trend can also be used in accordance with some embodiments.

The first time the process of FIG. 16 is performed, there is generally no line length trend against which to set a threshold. Accordingly, for the first several passes through the process (until a sufficient amount of EEG data has been processed to establish a trend), the threshold is essentially undefined and the line length detector should not return a positive detection. Some "settling time" thus can be used to establish trends and thresholds before detections are made.

If the accumulated line length total exceeds the calculated threshold (step 1626), then a flag is set (step 1628) indicating a line-length-based event detection on the current channel analysis unit channel 714. As described above, in some embodiments, the threshold is dynamically calculated from a line length trend, but alternatively, the threshold can be static, either fixed or programmed into the device 110. If the accumulated line length total does not exceed the threshold, the flag is cleared (step 1630). Once the line length flag has been either set or cleared, logic inversion is applied (step 1632), persistence is applied (step 1634), and the procedure terminates.

The resulting persistent line length flag indicates whether the threshold has been exceeded within one or more windows over a time period corresponding to the line length flag persistence. As discussed in further detail below, line length event detections can be combined with the half wave event detections, as well as any other applicable detection criteria according to some embodiments.

Figure 17:
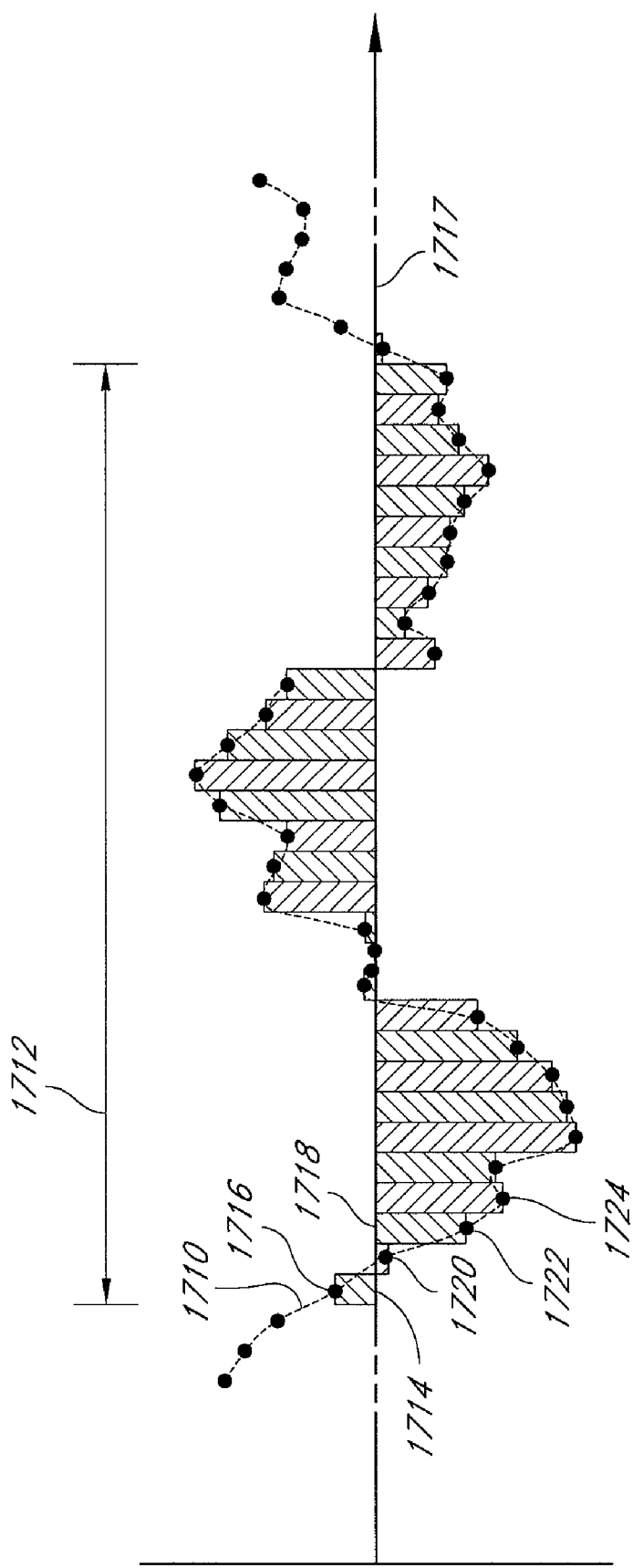
FIG. 17 is a graph of the exemplary EEG signal of FIG. 10A, after some filtering has been applied to it, and illustrating how an area function can be calculated.

FIG. 17 illustrates the waveform of FIG. 10D with area under the curve identified within a window. Area under the curve, which in some circumstances is somewhat representative of a signal's energy (though energy of a waveform is more accurately represented by the area under the square of a waveform), is another detection criterion that can be used in accordance with some embodiments.

The total area under the curve represented by a waveform 1710 within the window 1712 is equal to the sum of the absolute values of the areas of each rectangular region of unit width vertically bounded by the horizontal axis and the sample. For example, the first contribution to the area under the curve within the window 1712 comes from a first region 1714 between a first sample 1716 and a baseline 1717. A second contribution to the area under the curve within the window 1712 comes from a second region 1718, including areas between a second sample 1720 and the baseline 1717. There are similar regions and contributions for a third sample 1722 and the baseline 1717, a fourth sample 1724 and the baseline 1717, and so on. It should be observed that the region widths are not important—the area under each sample can be considered the product of the sample's amplitude and a unit width, which can be disregarded. In a similar manner, each region is accumulated and added to the total area under the curve within the window 1712. Although the concept of separate rectangular regions is a useful construct for visualizing the idea of area under a curve, it should be noted that a process for calculating area need not partition areas into regions as shown in FIG. 17—it is only necessary to accumulate the absolute value of the waveform's amplitude at each sample, as the unit width of each region can be disregarded. The process for doing this will be set forth in detail below in connection with FIG. 18.

Figure 18:
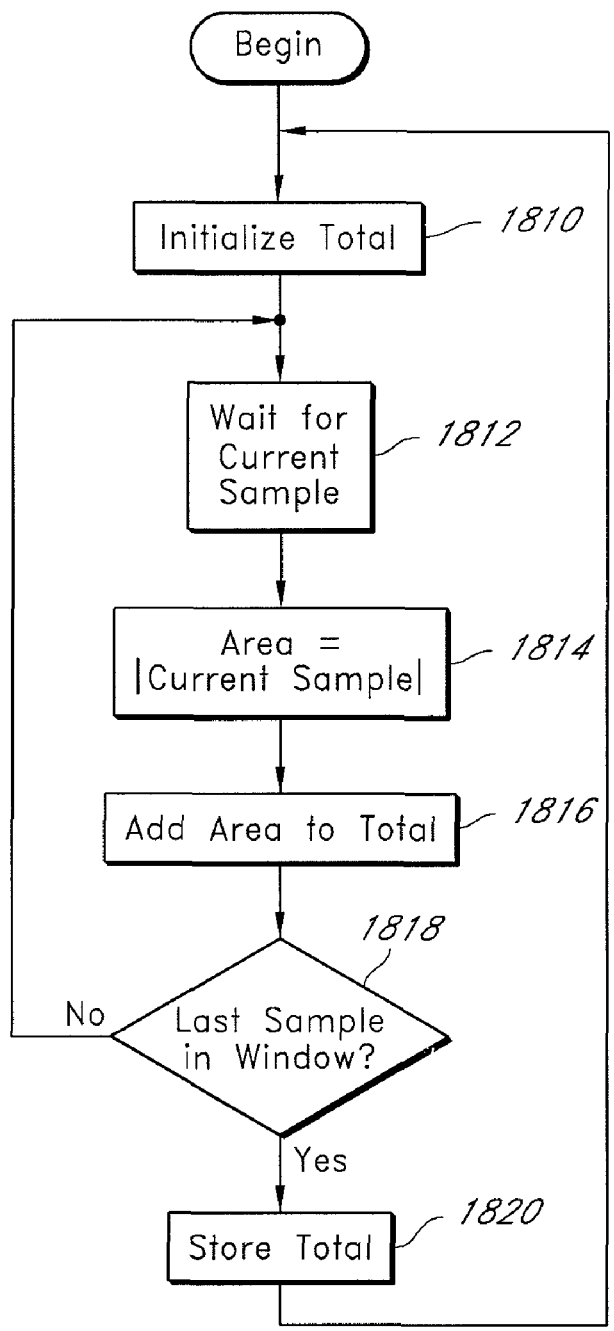
FIG. 18 is a flow chart illustrating a process performed by functional components of the waveform analyzer of FIG. 8 in calculating the area function.

The areas under the curve illustrated in FIG. 17 are calculated as shown by the flow chart of FIG. 18, which is invoked at the beginning of a time window. Initially, an area total variable is initialized to zero (step 1810). The current sample is awaited (step 1812), and the absolute value of the current sample is measured (step 1814).

As with the line length calculation method described above (with reference to FIG. 15), in various alternative embodiments, the current sample (as measured in step 1814, described above) can be mathematically transformed in useful nonlinear ways. For example, it can be advantageous in certain circumstances to calculate the square of the current sample rather than its absolute value. The result of such a transformation by squaring each sample will generally be more representative of signal energy, though it is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 110.

The calculated absolute value is added to the total (step 1816). If there are more samples remaining in the window 1712 (step 1818), another current sample is awaited (step 1812) and the process continues. Otherwise, the area calculation for the window 1712 is complete, and the total is stored (step 1820), the total is reinitialized to zero (step 1810), and the process continues.

As with the half wave and line length analysis methods set forth above, the area calculation does not need to terminate; it can be free-running yet interruptible. If the area calculation is restarted after having been suspended, it should be re-initialized and restarted at the beginning of a window. This synchronization can be accomplished through hardware interrupts.

Figure 19:
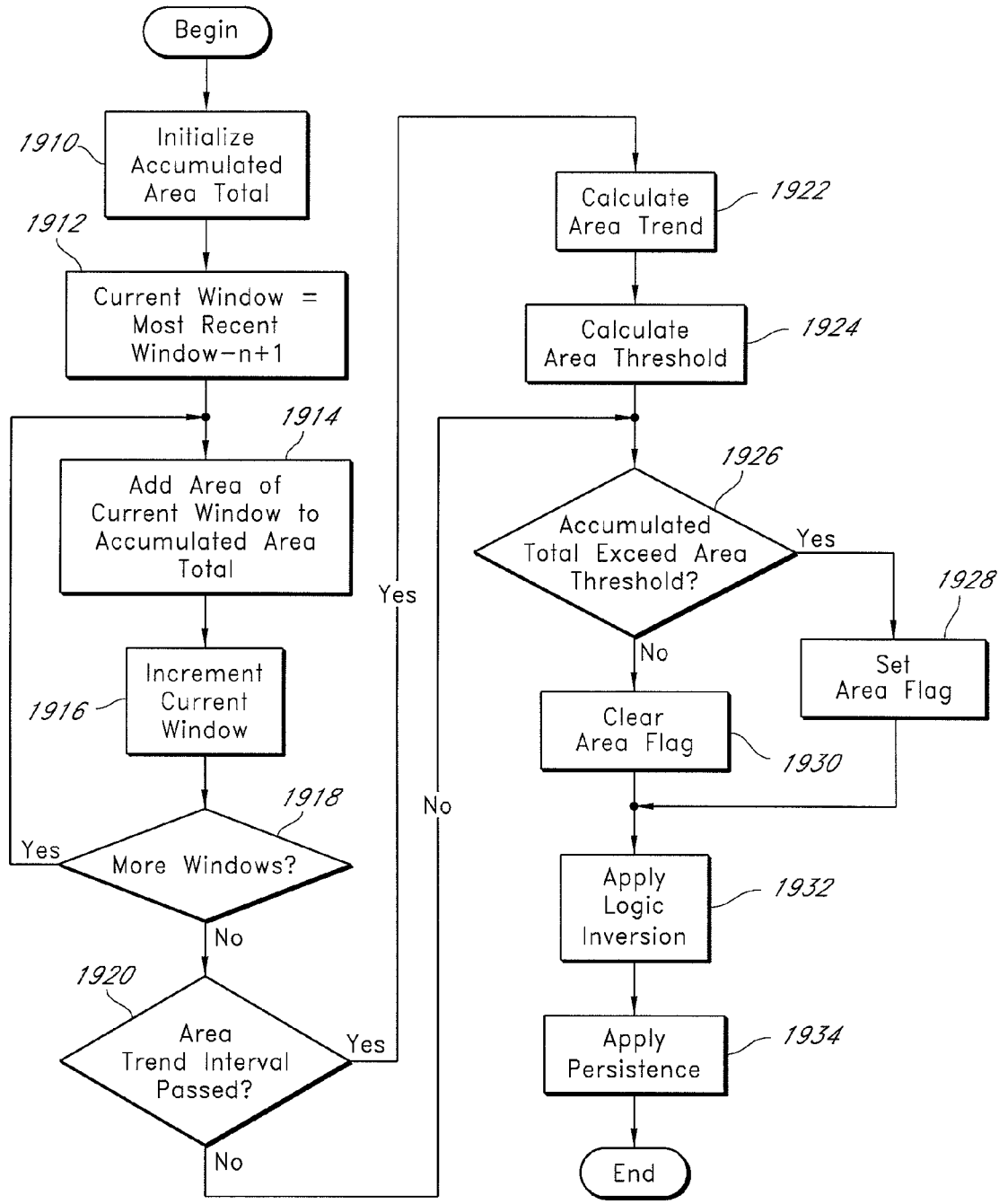
FIG. 19 is a flow chart illustrating a process performed by the central processing unit in calculating and analyzing the area function of an EEG signal.

The line lengths calculated as shown in FIG. 18 are then processed as indicated in the flow chart of FIG. 19, which is performed after each window 1712 is calculated and stored (step 1820).

The process begins by calculating a running accumulated area total over a period of n time windows. Where n>1, the effect is that of a sliding window; in an alternative embodiment an actual sliding window processing methodology can be used. First, the accumulated total is initialized to zero (step 1910). A current window pointer is set to indicate the $n^{th}$-last window, i.e., the window (n−1) windows before the most recent window (step 1912). The area for the current window is added to the total (step 1914), the current window pointer is incremented (step 1916), and if there are more windows between the current window and the most recent (last) window (step 1918), the adding and incrementing steps (1914-1916) are repeated. Accordingly, by this process, the resulting total includes the areas under the curve for each of the n most recent windows.

In some embodiments, the accumulated total area can be compared to a dynamic threshold, which can be based on a trend of recently observed areas. The trend can be recalculated regularly and periodically, after each recurring area trend interval (which is preferably a fixed or programmed time interval). Each time the area trend interval passes (step 1920), the area trend can be calculated or updated (step 1922).

In some embodiments, this can be accomplished by calculating a normalized moving average of several trend samples, each of which represents several consecutive windows of areas. A new trend sample can be taken and the moving average is recalculated upon every area trend interval. The number of trend samples used in the normalized moving average and the number of consecutive windows of area measurements per trend sample are preferably both fixed or programmable values.

After the area trend has been calculated, the area threshold can be calculated (step 1924) based on the new area trend. As with line length, discussed above, the threshold can be set as either a percentage of the area trend (either below 100% for a threshold that is lower than the trend, or above 100% for a threshold that is higher than the trend) or alternatively a fixed numeric offset from the area trend (either negative for a threshold that is lower than the trend, or positive for a threshold that is higher than the trend).

The first time the process of FIG. 19 is performed, there is generally no area trend against which to set a threshold. Accordingly, for the first several passes through the process (until a sufficient amount of EEG data has been processed to establish a trend), the threshold is essentially undefined and the area detector should not return a positive detection. Some "settling time" thus can be used to establish trends and thresholds before a detection can be made.

If the accumulated total exceeds the calculated threshold (step 1926), then a flag is set (step 1928) indicating an area-based event detection on the current window analysis unit channel 714. Otherwise, the flag is cleared (step 1930). Once the area flag has been either set or cleared, logic inversion is applied (step 1932), persistence is applied (step 1934), and the procedure terminates.

The resulting persistent area flag indicates whether the threshold has been exceeded within one or more windows over a time period corresponding to the area flag persistence. As discussed in further detail below, area event detections can be combined with the half wave event detections, line length event detections, as well as any other applicable detection criteria according to some embodiments.

In some embodiments, each threshold for each channel and each analysis tool can be programmed separately; accordingly, a large number of individual thresholds can be used. It should be noted thresholds can vary widely; they can be updated by a clinician via the external programmer 312 (FIG. 3), and some analysis tool thresholds (e.g., line length and area) can also be automatically varied depending on observed trends in the data. This is preferably accomplished based on a moving average of a specified number of window observations of line length or area, adjusted as desired via a fixed offset or percentage offset, and can compensate to some extent for diurnal and other normal variations in brain electrophysiological parameters.

With regard to the flow charts of FIGS. 11-13, 15, 16, and 18-19, it should be noted that there can be a variety of ways these processes are implemented. For example, state machines, software, hardware (including ASICs, FPGAs, and other custom electronics), and various combinations of software and hardware, are all solutions that would be possible to practitioners of ordinary skill in the art of electronics and systems design. It should further be noted that the steps performed in software need not be, as some of them can be implemented in hardware, if desired, to further reduce computational load on the processor. In the context of the present embodiments, it is not believed to be advantageous to have the software perform additional steps, as that would likely increase power consumption.

In some embodiments, one of the detection schemes set forth above (e.g., half wave detection) can be adapted to use an X-of-Y criterion to weed out spurious detections. This can be implemented via a shift register, as usual, or by more efficient computational methods. As described above, half waves are analyzed on a window-by-window basis, and as described above (in connection with FIG. 13), the window results are updated on a separate analysis window interval. If the detection criterion (i.e., a certain number of half waves in less than a specified time period) is met for any of the half waves occurring in the most recent window, then detection is satisfied within that window. If that occurs for at least X of the Y most recent windows, then the half wave analysis tool triggers a detection. If desired, other detection algorithms (such as line length and area) can operate in much the same way: if thresholds are exceeded in at least X of the Y most recent windows, then the corresponding analysis tool triggers a detection.

Also, in the disclosed embodiment, each detection flag, after being set, remains set for a selected amount of time, allowing them to be combined by Boolean logic (as described below) without necessarily being simultaneous.

As indicated above, each of the software processes set forth above (FIGS. 12, 13, 16, and 19) correspond to functions performed by the wave morphology analysis units 812 and window analysis units 814. Each one is initiated periodically, typically once per detection window (1212, 1512). The outputs from the half wave and window analysis units 812 and 814, namely the flags generated in response to counted qualified half waves, accumulated line lengths, and accumulated areas are combined to identify event detections as functionally illustrated in FIG. 9 and as described via flow chart in FIG. 20.

The process begins with the receipt of a timer interrupt (step 2010), which is typically generated on a regular periodic basis to indicate the edges of successive time windows. Accordingly, in a system or method in some embodiments, such a timer interrupt is received every 128 ms, or as otherwise programmed or designed. Then the half wave (step 2012, FIGS. 12, 13), line length (step 2014, FIG. 16), and area (step 2016, FIG. 19) analysis tools are evaluated with respect to the latest data generated thereby, via the half wave analysis flag, the line length flag, and the area flag for each active channel. The steps of checking the analysis tools (steps 2012, 2014, and 2016) can be performed in any desired order or in parallel, as they are generally not interdependent. It should be noted that the foregoing analysis tools should be checked for every active channel, and can be skipped for inactive detection channels.

Flags, indicating whether particular signal characteristics have been identified in each active channel, for each active analysis tools, can then be combined into detection channels (step 2018) as illustrated in FIG. 9. In some embodiments, this operation is performed as described in detail below with reference to FIG. 21. Each detection channel is a Boolean AND combination of analysis tool flags for a single channel, and as disclosed above, there can be one or more channels in a system according to some embodiments.

The flags for multiple detection channels are then combined into event detector flags (step 2020), which are indicative of identified neurological events calling for action by the device. This process is described below, see FIG. 20, and is in general a Boolean combination of detection channels, if there is more than one channel per event detector.

If an event detector flag is set (step 2022), then a corresponding action is initiated (step 2024) by the device. Actions according to some embodiments can include the presentation of a warning to the patient, an initiation of a device mode change, or a recording of certain EEG signals or other data; it will be appreciated that there are numerous other possibilities. It is preferred, but not necessary, for actions initiated by a device according to some embodiments to be performed in parallel with the sensing and detection operations described in detail herein.

Multiple event detector flags are possible, each one representing a different combination of detection channel flags. If there are further event detector flags to consider (step 2026), those event detector flags can also be evaluated (step 2022) and can cause further actions by the device (step 2024). It should be noted that, in general, actions performed by the device (as in step 2024) can be in part dependent on a device state—even if certain combinations of events do occur, no action can be taken if the device is in an inactive state, for example.

Figure 20:
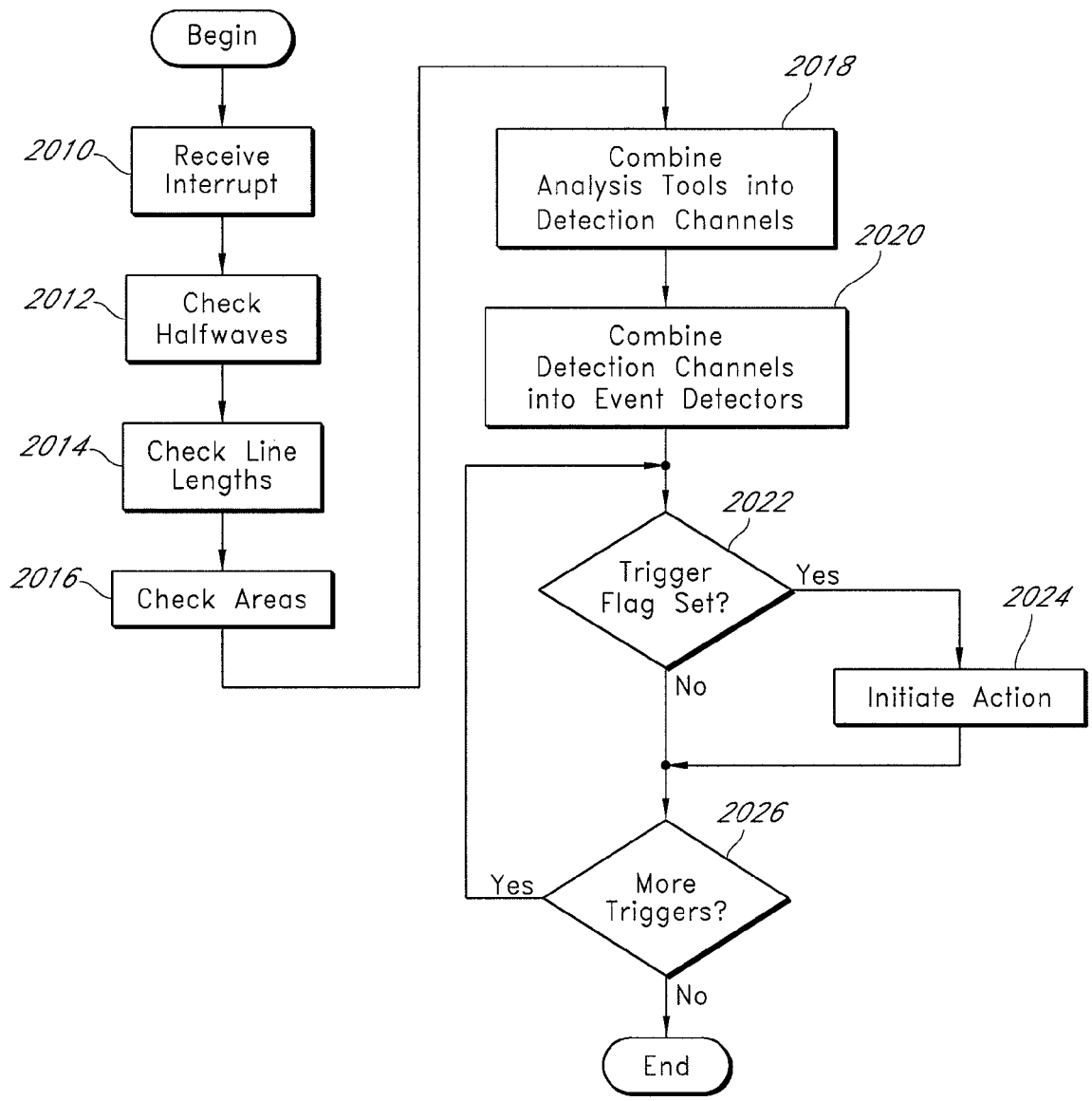
FIG. 20 is a flow chart illustrating a process that can be performed by the central processing unit to analyze half wave, line length, and area information for detection.
Figure 21:
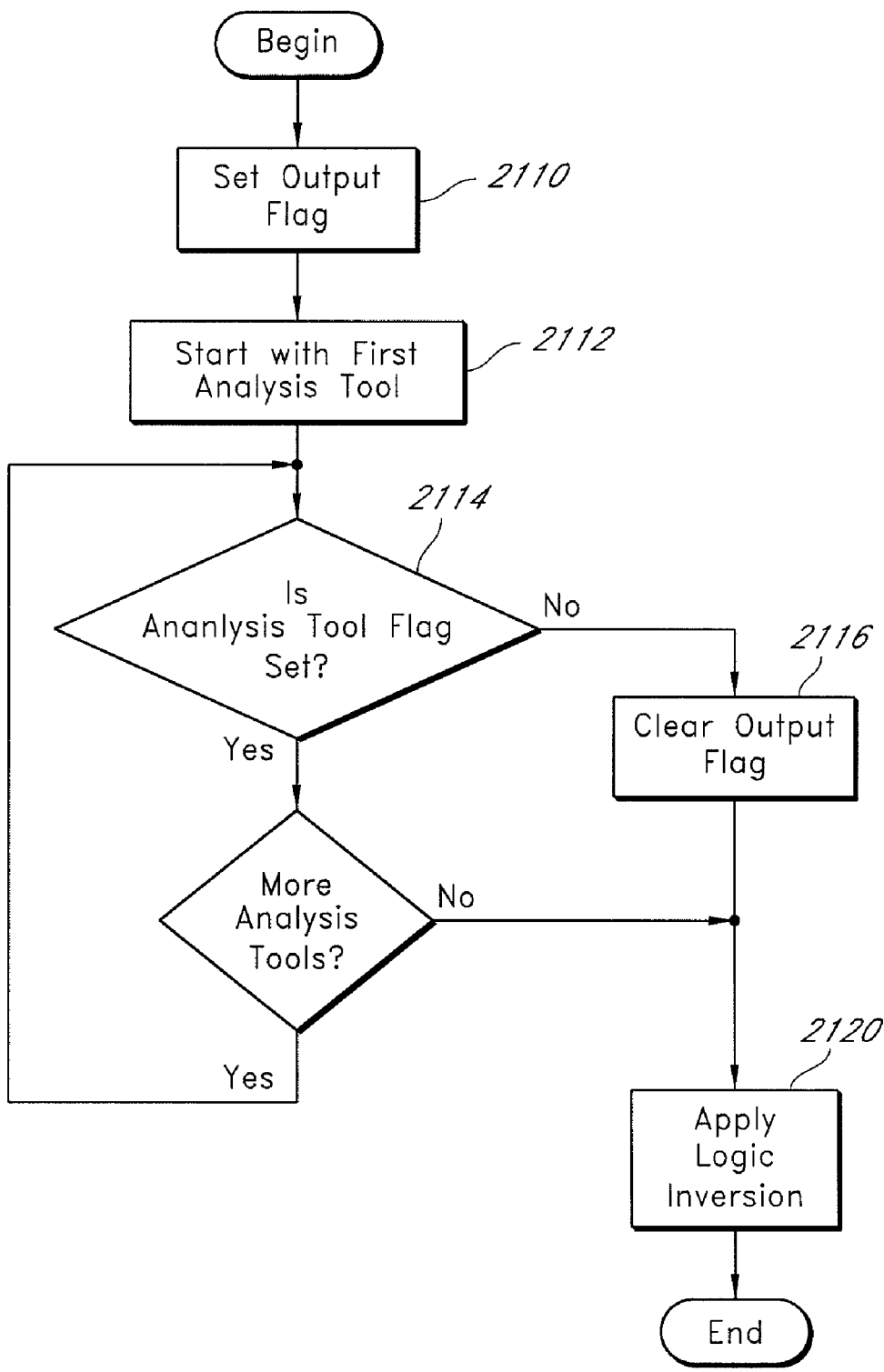
FIG. 21 is a flow chart illustrating one manner in which the half wave, line length and area function analysis tools can be combined to detect neurological events in an embodiment.

As described above, and as illustrated in FIG. 20 as step 2018, a corresponding set of analysis tool flags is combined into a detection channel flag as shown in FIG. 21 (see also FIG. 9). Initially, the output detection channel flag is set (step 2110). Beginning with the first analysis tool for a particular detection channel (step 2112), if the corresponding analysis tool flag is not set (step 2114), then the output detection channel flag is cleared (step 2116).

If the corresponding analysis tool flag is set (step 2114), the output detection channel flag remains set, and further analysis tools for the same channel, if any (step 2118), are evaluated. Accordingly, this combination procedure operates as a Boolean AND operation—if any of the enabled and active analysis tools for a particular detection channel does not have a set output flag, then no detection channel flag is output by the procedure.

A clear analysis tool flag indicates that no detection has been made within the flag persistence period, and for those analysis tools that employ an X-of-Y criterion, that such criterion has not been met. In certain circumstances, it can be advantageous to also provide detection channel flags with logic inversion. Where a desired criterion (i.e., combination of analysis tools) is not met, the output flag is set (rather than cleared, which is the default action). This can be accomplished by providing selectable Boolean logic inversion (step 2120) corresponding to each event detector.

Figure 22:
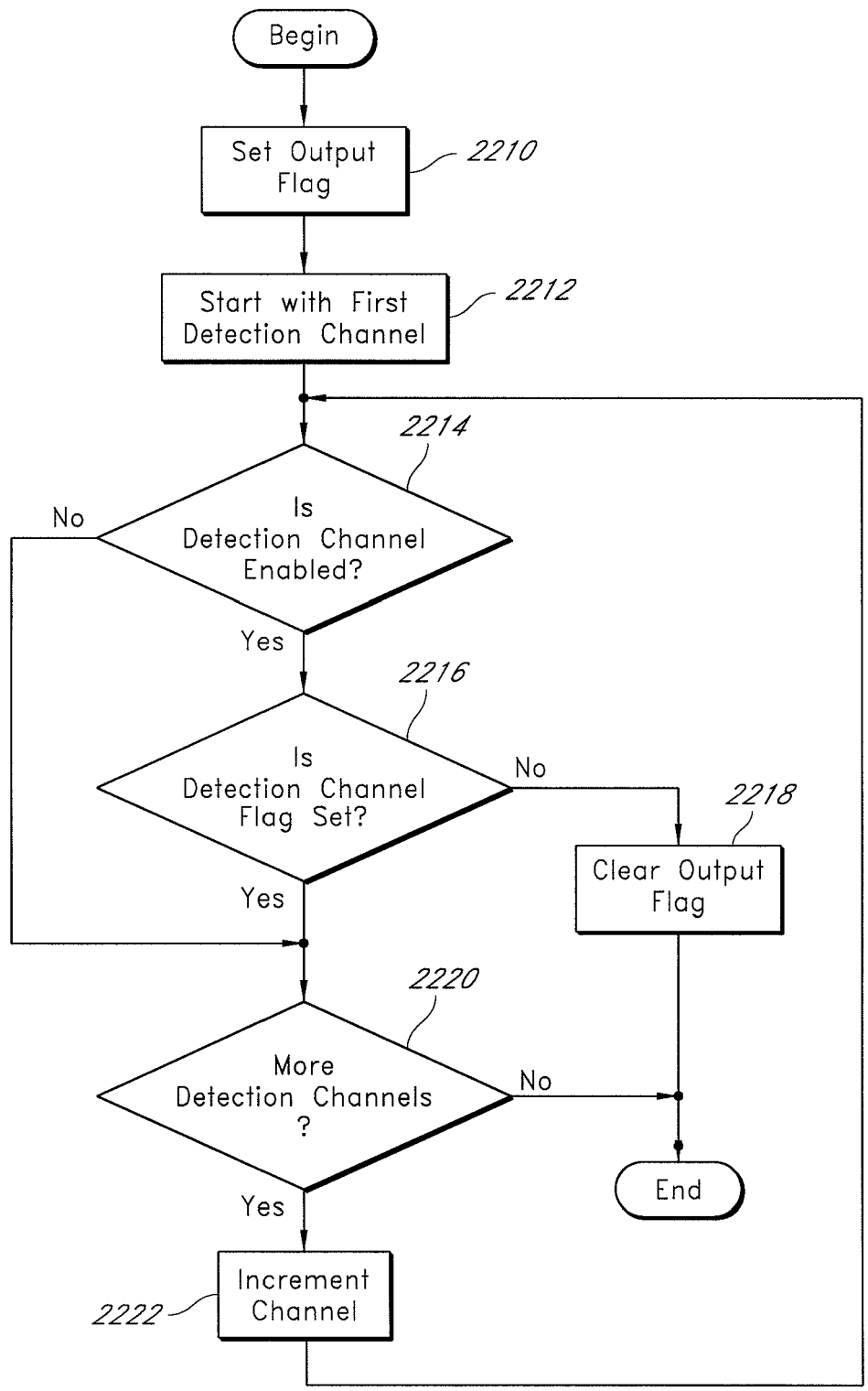
FIG. 22 is a flow chart illustrating one manner in which detection channels can be combined to detect neurological events in an embodiment.

Also as described above, and as illustrated in FIG. 20 as step 2020, multiple detection channel flags are combined into a single event detector flag as shown in FIG. 22 (see also FIG. 9). Initially, the output event detector flag is set (step 2210). Beginning with the first detection channel for a particular event detector (step 2212), if the channel is not enabled (step 2214), then no check is made. If the channel is enabled and the corresponding detection channel flag is not set (step 2216), then the output event detector flag is cleared (step 2218) and the combination procedure exits. If the corresponding detection channel flag is set (step 2216), the output event detector flag remains set, and further detection channels, if any (step 2220), are evaluated after incrementing the channel being considered (step 2222). Accordingly, this combination procedure also operates as a Boolean AND operation—if any of the enabled and active detection channels does not have a set output flag, then no event detector flag is output by the procedure. It should also be observed that a Boolean OR combination of detection channels can provide useful information in certain circumstances; a software or hardware flow chart accomplishing such a combination is not illustrated, but could easily be created by an individual of ordinary skill in digital electronic design or computer programming.

With reference again to FIG. 20, in some embodiments, the actions taken in the step 2024 can include logging the event flags, logging a summary of the event flags, logging a single event as a result of one or more flags being set, saving the EEG signals detected by the channel, saving portions of EEG signals detected before, during, or after any of the above-noted flags are set, and recording or saving any data generated during the analysis of waveforms noted above, and the like.

Figure 23:
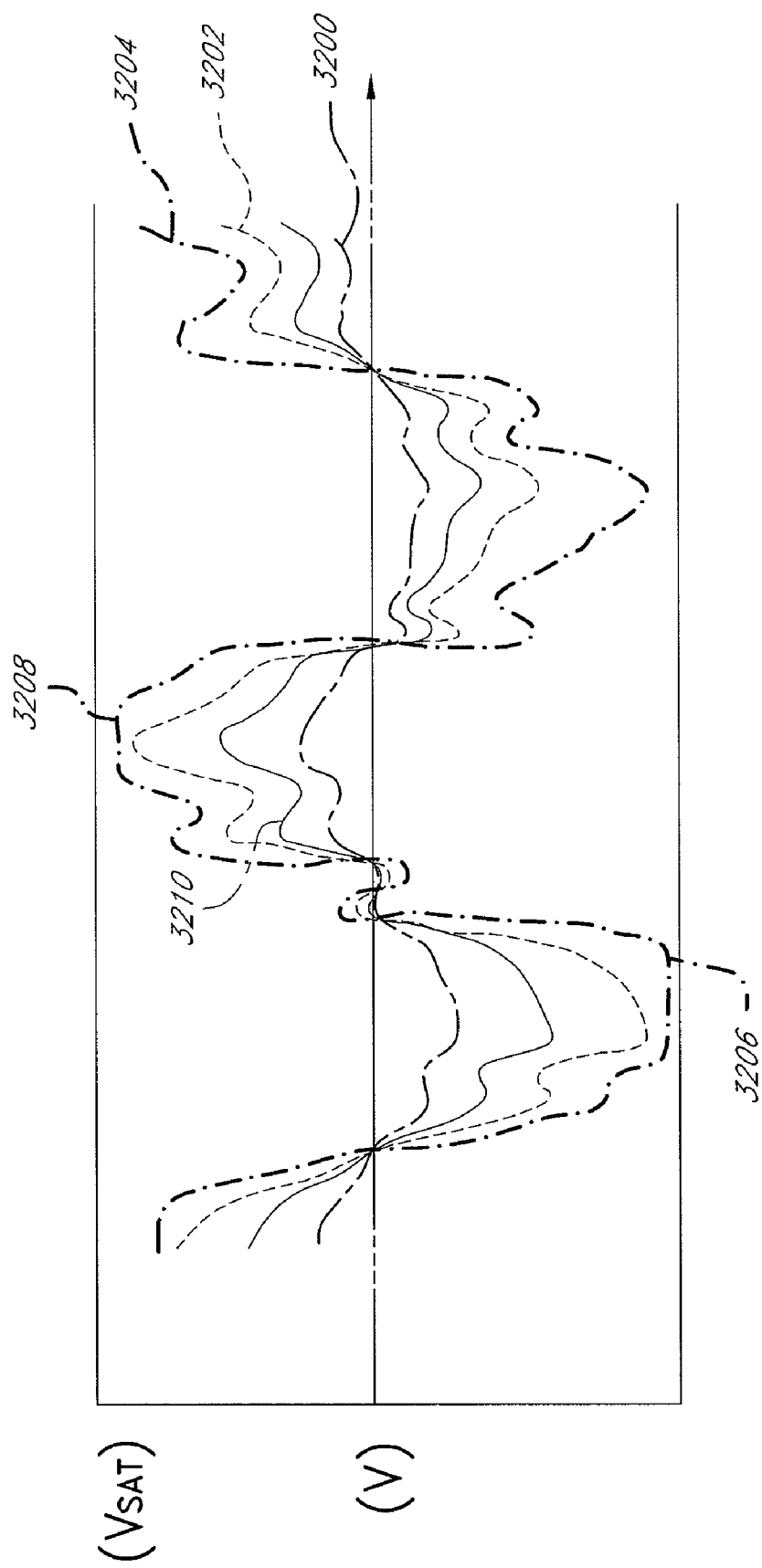
FIG. 23 is a schematic representation of a patient's brainwaves and illustrates various stages of adjustment of an amplifier within the implantable neurostimulator.

With reference to FIG. 23, in an alternative embodiment, a filtered voltage 1004 (FIG. 10B), can be recorded and used to provide a simplified method for diagnosing and/or detecting epileptic seizures or other neurologic events.

Here, when a device such as one of the embodiments of the devices 110 described above, is first installed, the maximum amplitudes of voltages detected by the electrodes 412, 414, 416 and 418 cannot be predicted. After the initial installation of such a device, amplifier adjustments can be made so that the voltages output from the amplifier 710 are within a normal operation range for the amplifier 710, and such that the voltage output from the amplifier 710 does not reach the maximum output voltage of the amplifier 710 an excessive number of times.

For example, FIG. 23 illustrates voltage traces of several other exemplary outputs from the amplifier 710. The voltage traces 3200, 3202, and 3204 are examples of the output of the amplifier 710 at different gain settings, resulting from an input to the amplifier 710 represented by voltage trace 3210. The amplifier 710 can be any type of amplifier. In some embodiments, the amplifier 710 has an adjustable gain. The adjustable gain feature is provided through the use of a variable resistor. However, any type of adjustable gain amplifier can be used.

In FIG. 23, the voltage trace 3204 is an example of the filtered output of the amplifier 710 having been adjusted to its maximum gain. As reflected in the voltage trace 3204, the amplifier 710 reaches its saturation point and thus, the voltage trace 3204 reaches and remains constant at maximum and minimum voltage portions 3206 and 3208, respectively. Assuming that the brainwaves generating this voltage signal are normal, i.e., not indicative of epileptic seizures, it is undesirable for the amplifier 710 to reach its saturation point frequently. For example, in some embodiments, it is acceptable if the voltage output from the amplifier 710 reaches its saturation point no more than about once per second.

However, if the amplifier 710 reaches its saturation point and thus outputs maximum or minimum voltages more than about once per second during normal brainwave activity, then the gain of the amplifier 710 may be too high. Thus, the gain of the amplifier 710 can be reduced until the signal output from the amplifier 710 reaches its maximum or minimum values no more than about once per second. After the gain of the amplifier 710 has been adjusted as such, the device 110 can be used for the diagnostic and therapeutic uses noted above.

Figure 25:
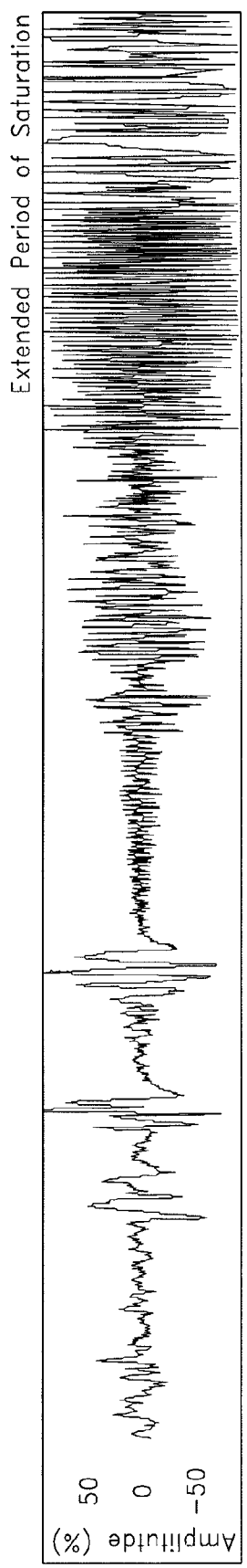
FIG. 25 is an exemplary depiction of a patient's brainwaves detected by the neurostimulator and including an extended period during which an amplifier in the neurostimulator is saturated.

For example, when a seizure occurs, the EEG waveform typically appears as a reciprocating waveform that reaches saturation voltage for an extended period of time, for example, as shown in FIG. 25. The time at which the EEG reaches saturation voltage will depend on the gain setting, with higher gain settings producing earlier but more frequent saturation events.

Figure 26:
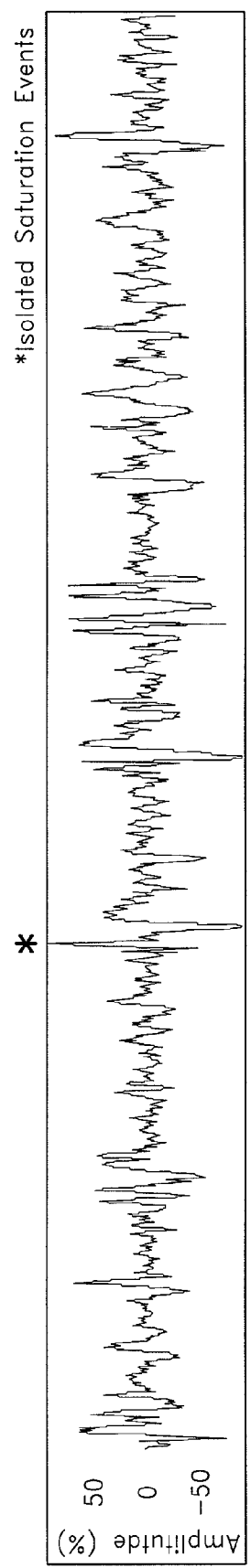
FIG. 26 is another exemplary depiction of a patient's brainwaves detected by the neurostimulator and including only isolated events during which an amplifier in the neurostimulator is saturated.

Interictal (non-seizure) baseline EEG can also have brief periods of saturation that can be abnormal as shown in FIG. 26 (marked by asterisks). The clinician may not want these brief saturation events to be reported because they do not represent seizures or other significant neurological events and they can occur quite frequently. Therefore, the device 110 should be able to distinguish between sustained periods of saturation that can be neurological events of clinical significance and brief periods of saturation that can be frequent and not of clinical significance.

Figure 24:
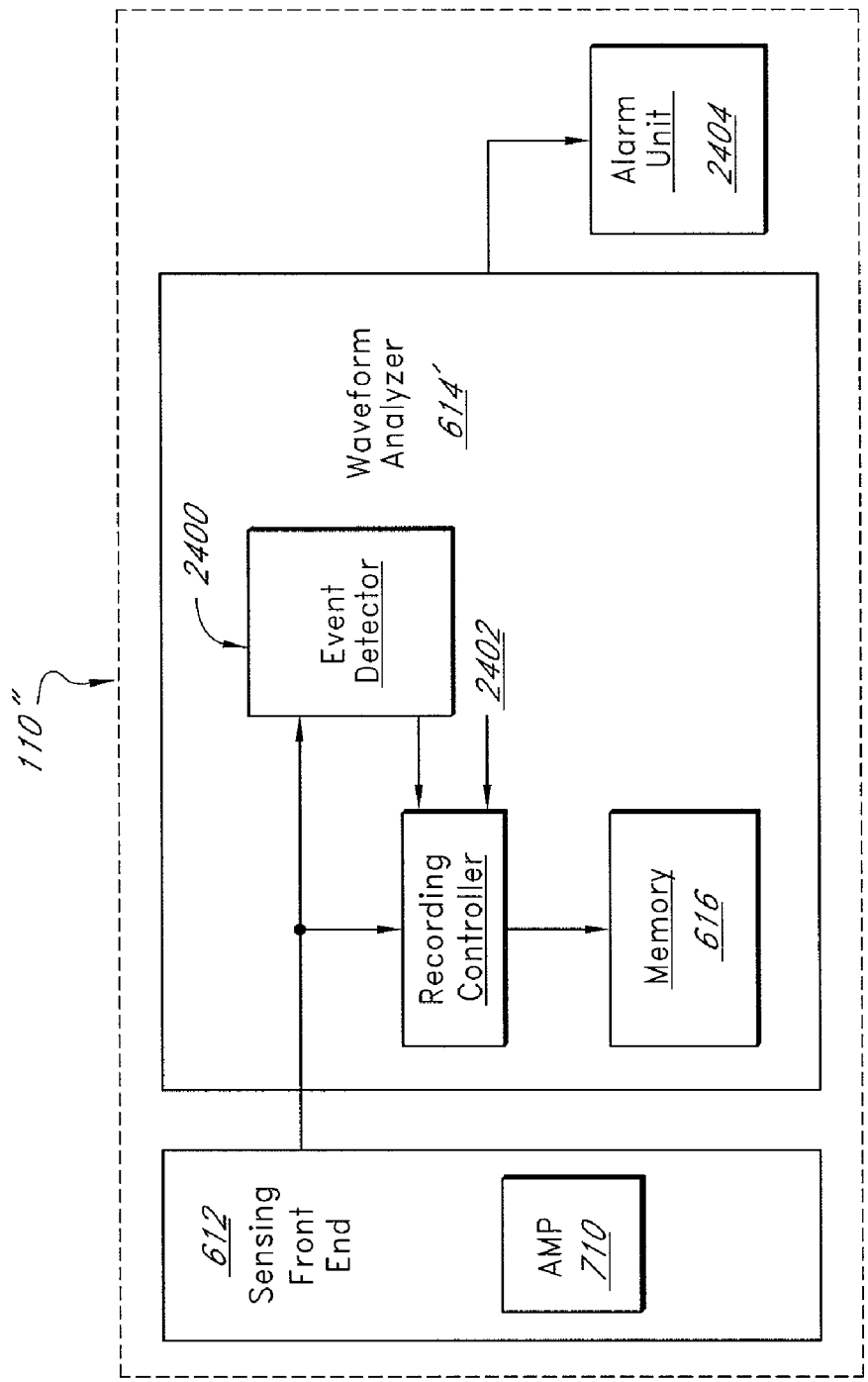
FIG. 24 is a schematic illustration of a modification of a waveform analyzer that can be included in any of the implantable neurostimulators illustrated in the above figures.

For example, with reference to FIG. 24, a modification of the waveform analyzer 614 (FIG. 6) is illustrated therein and identified generally by the reference to numeral 614'. The waveform analyzer 614' includes some components that can be constructed in accordance with the description noted above with respect to the analyzer 614. Other components of the analyzer 614' also correspond to components of the analyzer 614 but include modifications. As such, those components are identified with the same reference number used in the description of the analyzer 614 except that a "'" has been added thereto.

As shown in FIG. 24, the waveform analyzer 614' can include an event detector 2400, a recording controller 2402 and a memory device 616. However, the waveform analyzer 614' can also include other devices.

Figure 27:
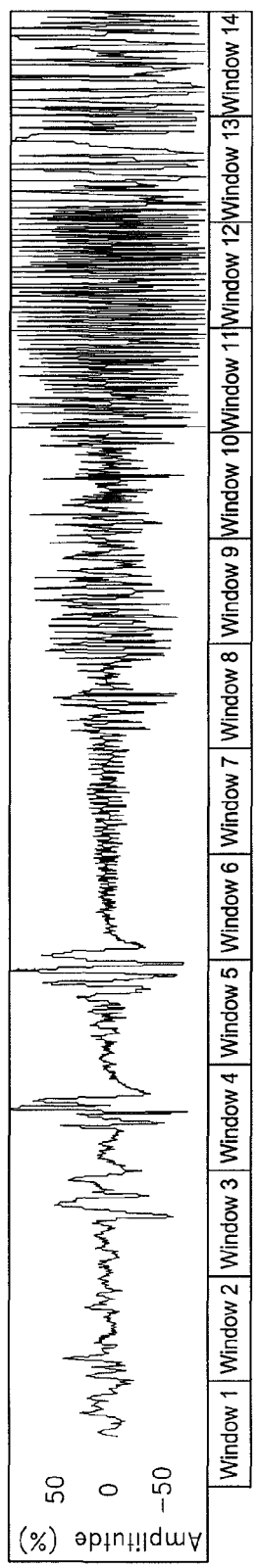
FIG. 27 includes, in an upper portion, the depiction of a patient's brainwaves from FIG. 25, broken down into windows, and a table, in a lower portion, tabulating saturation count criteria for each window.

In some embodiments, the event detector 2400 can be programmed to determine whether saturation is occurring at a predetermined rate and/or for a predetermined sustained period of time. An exemplary waveform of significant neurological event is shown in FIG. 27. The waveform data in FIG. 27 has been subdivided into a series of windows (labeled "Windows 1-14" in FIG. 27), which can be of any programmable length, but, in some embodiments can be 25-1000 msec. These windows can overlap, but are shown as non-overlapping in FIG. 27.

The waveform analyzer 614' can be configured to determine if any data point within any window is saturated. In the representative waveform in FIG. 27, an asterisk below the respective windows indicates which windows have a saturated data point.

In some embodiments, the clinician can program the event detector 2400 with regard to how many windows within a continuous subset would need to have a saturated data point in order for the event detector to determine that a seizure has occurred. For example, the practitioner could specify that X out of Y contiguous windows would be required to have a saturated event (where Y is always greater or equal to X) for the event detector 2400 to determine a seizure or significant neurological event has occurred.

The table in FIG. 27 shows various outcomes for different saturation count criteria X and Y values for the representative waveform (a "+" in a table block indicates that detection has occurred). These types of detections are referred to as X/Y saturation detections.

In some embodiments, the event detector 2400 can be configured to determine whether a seizure or other neurological event has occurred based upon analyses of X/Y saturation detections. In such embodiments, the event detector 2400 can be programmed to determine how frequently X/Y saturation detections are occurring and then only report neurological events to the practitioner if the X/Y saturation rate exceeds a certain rate of occurrence. For example, the detector 2400 can be configured to monitor the number of times that the X/Y saturation criteria were met in a programmable time window, but then only report an event to the practitioner if a minimum number of programmable X/Y saturation events were detected in a programmable time period.

For example, the detector 2400 can be programmed with a time window of five minutes and an X/Y saturation count criterion of five. The detector would then only report or record a neurological event if five or more X/Y saturation events were to have occurred in the past five minutes.

The recording controller 2402 can be configured to record and store recordings of the patient's brainwaves under certain circumstances. In some embodiments, the recording controller 2402 can be configured to utilize the memory device 616 to serve as a linear cache and a file storage unit.

For example, in various other areas in the signal processing arts, a linear cache is a known device for storing a single stream of digital information in a proper sequence. As such, the linear cache maintains this stream as a list of the digital blocks that make up the stream. In some embodiments, the digital blocks can each have a unique size and unique attributes, or the blocks can have a predetermined size, for example corresponding to a predetermined period of time such as 1 second, 5 five seconds, 10 seconds, 30 seconds, etc. However, the blocks can have any size. Each block within the stream can be marked with a "presentation timestamp" which indicates when that block should be presented to a decoding process.

The presentation timestamp can be a monotonically increasing value initialized at zero when the linear cache first begins operation on a stream of data. In some embodiments, the presentation timestamp generates its own time stamp signature without any relation to any other underlying clocking or streaming technique. The technique used for generating the presentation timestamp is also utilized by any decoding process used to read the digital blocks in the order recorded.

In some embodiments, the recording controller 2402 time stamps each encoded digital block of data from the sensing front end device 612 as it arrives at the recording controller 2402. In other words, the recording controller 2402 marks that block of data with the current presentation timestamp for the stream of data being recorded.

The recording controller 2402 can be configured to maintain a window of blocks in a window cache, for example. The recording controller 2402 can form a window cache of digital blocks, in the order according to the presentation timestamp values. As such, the window can contain the newest block that arrived in the window cache of digital blocks and the oldest block that this window cache is configured to hold. The window cache can be configured to hold any number of digital blocks.

For example, the window cache can be configured to hold the number of digital blocks corresponding to the amount of time to equal to 10 seconds, 30 seconds, 1 minute, 10 minutes, 30 minutes, 60 minutes, or any amount of time. In some embodiments, the recording controller 2402 can have an adjustable window size allowing a clinician to adjust the duration of the window size which the window cache will hold. This allows the clinician to adjust the length of the recorded brainwaves before a seizure is detected and after a seizure is detected.

In other words, the window cache of digital blocks represents a time span into the past history of the stream of brainwaves coming from the sensing front end 612. The recording controller 2402 can be configured to discard digital blocks that fall outside the window cache. In other words, the recording controller 2402 can be configured to erase digital blocks that fall outside of the window cache. As such, the window is sized such that one can only look back a limited distance into the past history of the data stream output from the sensing front end 612. This allows for trade-offs between the available storage space and the availability of past information for storing.

Additionally, in some embodiments, the recording controller 2402 can be configured to store all or a portion of the digital blocks stored within the cache window into a file when the event detector 2400 indicates that a seizure or other event has occurred. In some embodiments, the recording controller 2402 can be configured to store all of the digital blocks held in the window cache in a file when the event detector 2400 indicates the seizure has begun or occurred and to continue to add digital blocks to the file for an amount of time after the event detector 2400 indicates the seizure has been detected. In some embodiments, the recording controller 2402 can be configured to continue recording the output from the sensing front end 612 until the event detector 2400 indicates that the seizure has ended. Further, in some embodiments, the recording controller 2400 can be configured to continue to add digital blocks to the file for a predetermined time after the event detector 2400 indicates that the seizure has ended.

Optionally, the recording controller 2402 can be configured to save only a number of digital blocks within the window, at the time detector 2400 indicates the seizure has begun, corresponding to a predetermined time before the event detector 2400 indicates the seizure has begun. This predetermined time can be any predetermined time. For example, but without limitation, this predetermined time can be equal to 10 seconds, 30 seconds, 60 seconds, or any predetermined amount of time. Additionally, in some embodiments, the recording controller 2402 can be configured to allow this predetermined time to be adjusted by a practitioner.

After the recording controller 2402 has collected all the digital blocks surrounding the detection of a seizure by the event detector 2400 and to include the digital blocks corresponding to the predetermined time periods before and after the event detector 2400 indicates a seizure has occurred, the recording controller 2402 can save the file including these blocks into the memory device 616. Additionally, the recording controller 2402 can stamp the file with the date and time for further analysis by a practitioner. As such, the waveform analyzer 614' provides additional advantages in the ability to more simply distinguish between normal brain activity and brain activity associated with the seizure and to save the relevant portions of the brain wave signals received from the sensing front end 612 in a more efficient manner thereby saving memory and reducing power consumption.

The above-described method for generating files of selected portions of detected brainwave activity can be incorporated into any of the embodiments of the device 110 described above or below.

Such a method for storing selected portions of detected brain wave activity can also aid in the process of calibrating the amplifier 710. For example, after the initial installation of a device 110, and preferably after the patient has suffered one or more seizures, the files containing the selected portions of detective brain wave activity can be reviewed by a practitioner. An clinician can readily identify whether or not these files of selected brain wave activity include brain wave activity resulting from a seizure.

If the clinician determines that the files do not contain brainwaves resulting from seizure activity, the clinician can use the recordings to determine what adjustments to make to the device 110. For example, the practitioner can determine that it is necessary to adjust the gain of the amplifier 710, or to make other adjustments.

Figure 28A:
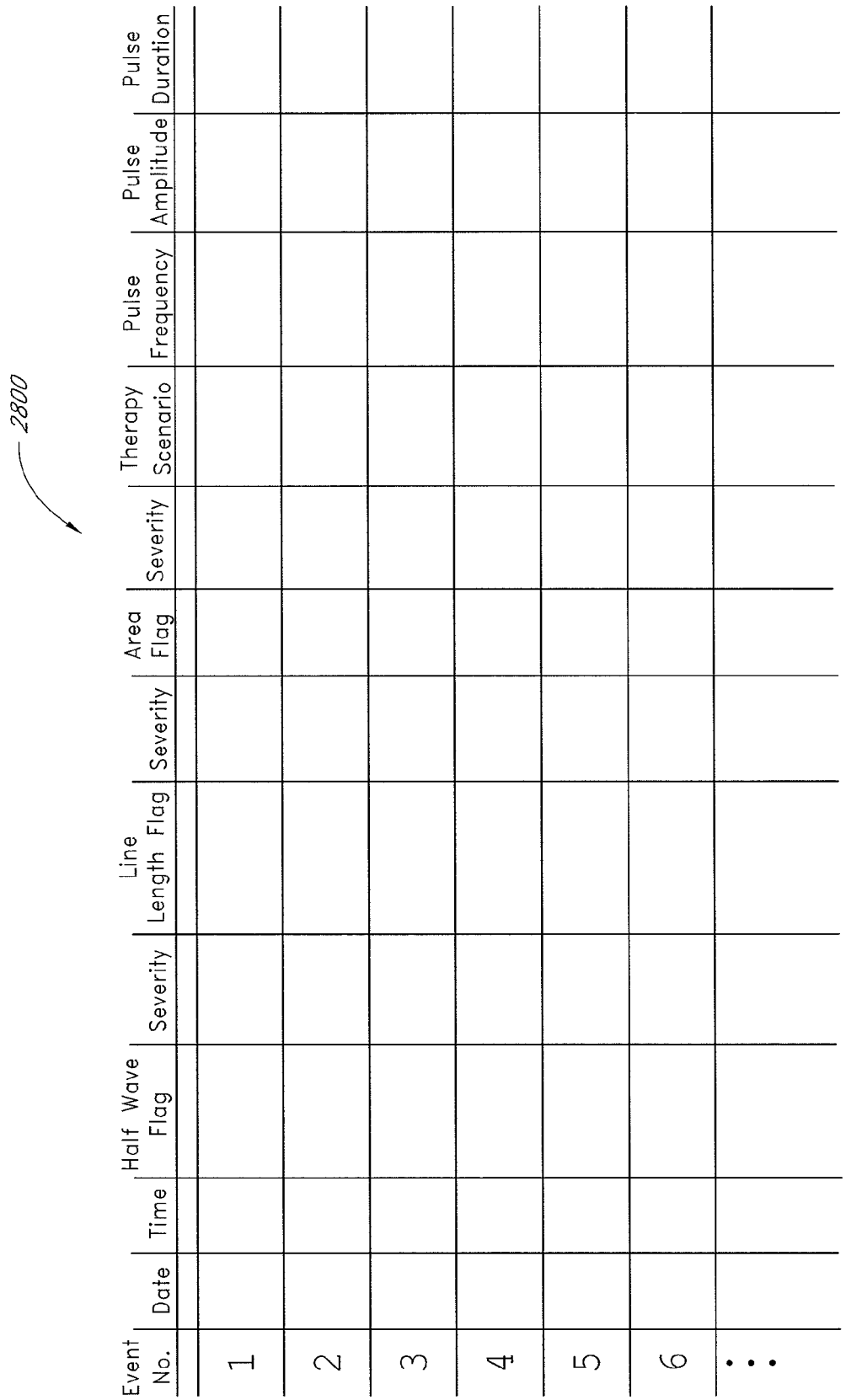
FIG. 28A is an exemplary log of data indicative of the occurrence of neurological events that can be used in conjunction with the implantable neurostimulators disclosed herein.

In some embodiments, additional data about the detection of a neurological event can be saved in the memory 616, memory subsystem 431, or any other memory device included in the implantable neurostimulator device 110, in the form of tabulated data, or in any other form. For example, in some embodiments, the tabulated data can be saved in the diagnostic records storage facility 510 of the memory subsystem 431 (FIG. 5). An exemplary data table 2800 is illustrated in FIG. 28A. In some embodiments, the tabulated data can include a date stamp indicating the date upon which a neurological event, such as those associated with the above-noted detection flags, is detected. Further, the data can include a time stamp indicating the time at which one of the above-noted flags is set. In some embodiments, the data table 2800 can further include data about the therapy applied in response to the detection of a neurological event, such as, the stimulation scenario used, the frequency of electrical stimulation, the stimulation pulse amplitude, the stimulation pulse width, the pulse-to-pulse interval, the electrodes used, the amount of time the simulation signal, or any combination thereof.

Figure 28B:
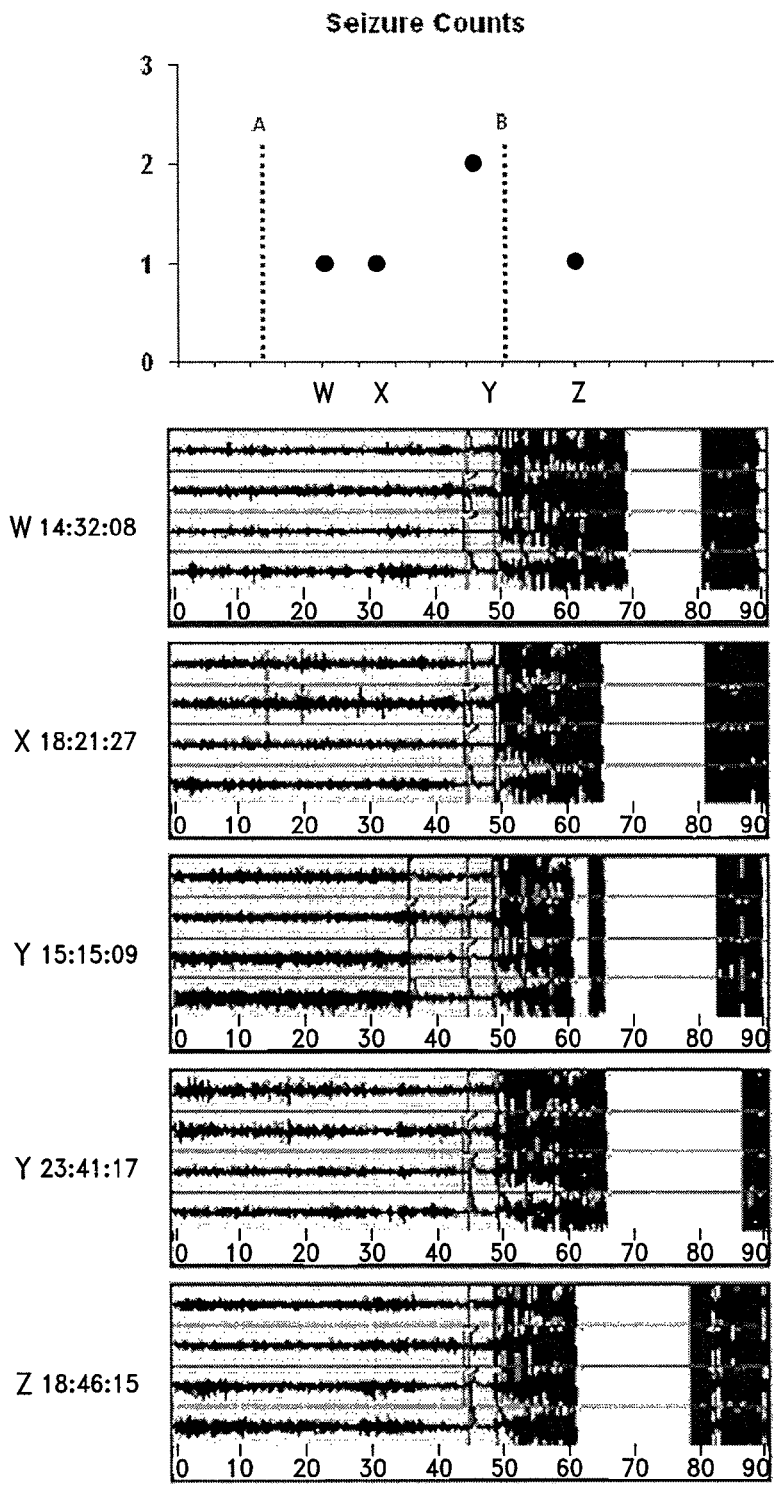
FIG. 28B is an exemplary seizure report that can be generated based on information gathered by any of the implantable neurostimulators illustrated in these figures.

FIG. 28B illustrates an exemplary but nonlimiting example of a report that can be generated with data collected by the device 110. At the top of the exemplary report of FIG. 28B are a number of data fields that can include, for example, but without limitation, the patient's name, the date of the report, the name of the clinician, the date range during which recordings were taken, and a key identifying when medications have changed or when other clinically significant events occur.

Below these data fields is a chart indicating the number of seizures identified by the device 110. This chart is labeled "seizure counts". The vertical axis of this graph indicates the number of seizures counted. The horizontal axis can serve as a timeline. In this case, the days on which seizures were counted are identified as Day W, Day X, Day Y, and Day Z. On the days identified as W, X, and Z, one seizure was counted on each day. On the day labeled Day Y, two seizures were counted.

Below the seizure count chart are samples of brainwave recordings that can be captured by the device 110. Each of these recordings are identified corresponding to the day and time at which they were recorded.

As noted above, the seizure report of FIG. 28B is merely an exemplary report that can be generated from the data captured by the implantable recording device 110. Other reports can also be generated. Further, such reports can be organized in different ways and can include other or different information.

Such tabulated data can include an indication of the type of flag that has been set, such as, for example, but without limitation, the set area flag of step 1928, the set line length flag of step 1628, and the set half wave flag of step 1322, and/or other flags.

As shown in FIG. 28A, the tabulated data can optionally include an indication of the severity of the neurological event. For example, the routine illustrated in FIG. 19 can be modified to include an additional operation to save to memory the area trend calculated in step 1922. This saved area calculation can then be stored in the table 2800 if the area flag is set in step 1928. Alternatively, other calculations can also be used to create an indication of the severity of the event causing the area flag to be set in step 1928.

Similarly, the routine of FIG. 16 can be modified to include an additional operation of saving the value of the calculation of the line length trend in step 1622. In such embodiments, this routine can also be modified to save the line length trend value calculated from step 1622 of FIG. 16 to the table 2800 when the line length flag is set in steps 1628. However, other calculations can also be used to create an indication of the severity of the neurological event causing the line length flag to be set in step 1628.

Additionally, the routine of FIG. 13 can be further modified to save the value generated from the sum of step 1314 when the half-wave flag is set in step 1322. Additionally, the routine can be modified to save the value of the sum from step 1314 to the table 2800 so as to provide an indication of the severity of the neurological event causing the half-wave flag to be set in step 1322. However, other calculations can also be made to provide an indication of the severity of the event causing the half-wave flag to be set in step 1322.

In some embodiments, the routine of FIG. 20 can be modified to save data associated with half-wave, line length, or area analyses performed in steps 2012, 2014, 2016, or other analyses. For example, the routine of FIG. 20 can be modified to include an additional operation associated with the operation block 2024 in which an event is logged on the table 2800 when any flags are indicated as being set in any of the operation blocks 2012, 2014, 2016. Such a tabulated dataset can include a date stamp and/or time stamp. Further, such a dataset can also include an indication of the severity of the neurological event triggering any of the flags associated with the operation blocks 2012, 2014, 2016, as illustrated in FIG. 20.

In some embodiments, the routine of FIG. 20 can be configured to log a neurological event only if all of a half-wave flag, a line length flag, and an area flag are set as a result of operation blocks 2012, 2014, 2016. This can provide the benefit of saving memory in the memory device 616 by reducing the number of events that are logged. However, other restrictions can also be used. For example, the routine of FIG. 20 can be modified to log an event only if at least two flags are determined as being set through the operation blocks 2012, 2014, 2016. However, other analyses can also be used to determine when to log a neurological event.

In some embodiments, once an event has been detected, the implantable device 110 can be configured to provide a first course of therapy to the patient, such as an electrostimulation. For example, in some embodiments, responsive stimulation 428 can be provided in response to conditions detected by the detection subsystem 423 (FIG. 4). In other embodiments, the programmed stimulation function 426 can be configured to provide a course of therapy to the patient without requiring the detection of a neurological event. For example, in some embodiments, the implantable device 110 can be configured to provide a course of therapy continuously or according to a preprogrammed delivery schedule. The various forms of stimulation described above can be programmed or commanded by a clinician using the programmer 312 (FIG. 3). In alternative embodiments, a range of stimulation parameters can be provided by the clinician via programmer 312 and these parameters can then be used by the auto-adjust module 440 to select, provide and alter the course of therapy provided according to a predetermined routine, according the event detection, or alternatively, in a random or pseudorandom manner.

Figure 29:
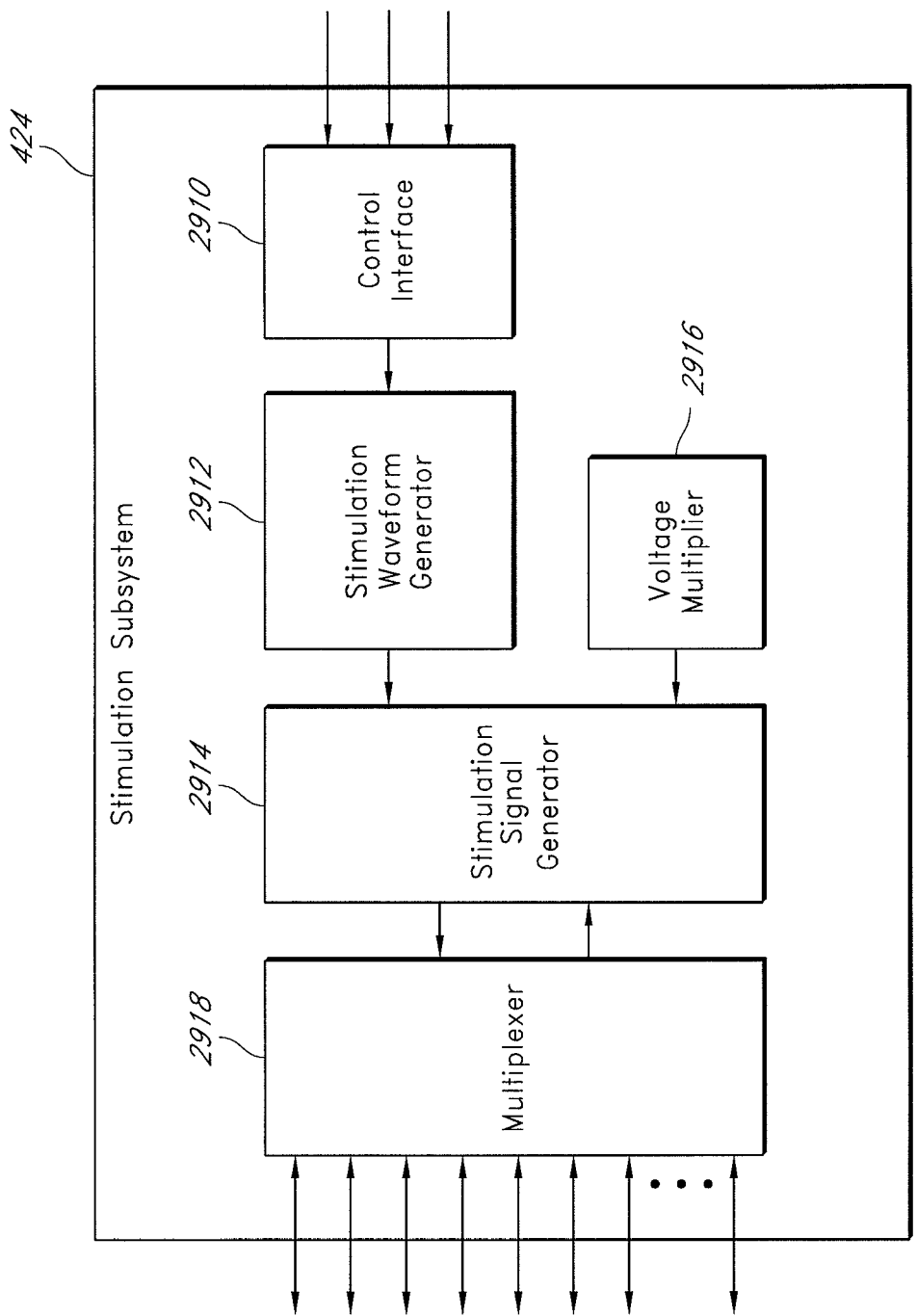
FIG. 29 is a block diagram illustrating the functional components of a therapy subsystem of the implantable neurostimulator of FIG. 4.

Referring to FIG. 29, to provide a course of therapy, a stimulation waveform generator 2912 can be activated in response to conditions detected by the detection subsystem 423, or alternatively according to a predetermined time schedule. The stimulation waveform generator 2912 can be coupled to a stimulation signal generator 2914. The stimulation signal generator 2914 receives commands and data from the stimulation waveform generator 2912, and generates electrical stimulation signals having the desired characteristics that are time-scheduled and synchronized. The stimulation signal generator 2914 receives power from a controllable voltage multiplier 2916 to facilitate the application of a proper current (or voltage) to the desired neurological tissue. Preferably, in conjunction with the voltage multiplier 2916, the stimulation signal generator 2914 acts as a current source and sink that is capable of delivering a precisely controlled current across at least a pair of the electrodes 412-418 (FIG. 4). The voltage multiplier 2916 can be configured to create relatively high voltages from a battery power source, which typically has a relatively low voltage. Circuits to accomplish this function are well known in the art of electronics design.

The stimulation signal generator 2914 can be configured to apply the electrical current to the electrodes 412-418 (FIG. 4) through a multiplexer 2918, which in some embodiments is capable of selecting a set of electrodes through which the electrical current is to be applied. The multiplexer 2918 couples at least one delivery electrode to the current source of the stimulation signal generator 2914 and at least one return electrode to the current sink of the stimulation signal generator 2914. Accordingly, the multiplexer 2918 has a plurality of outputs, which can be coupled to the electrode interface 420 (FIG. 4).

The stimulation waveform generator 2912 is invoked by the CPU 432 via the control interface 2910 when it is time to perform the required stimulation. In general, when an event is detected by the device 110, or when a selected and preprogrammed time has been reached, the CPU 432 is activated and caused to schedule an interrupt to occur when the scheduled stimulation is programmed to start. The CPU 432 can control the interrupt to occur a short time before scheduled stimulation to allow for any prestimulation "warm up" or preprocessing to be accomplished by the stimulation subsystem 424; a stimulation waveform generated according to the some embodiments (as described below) can be given a built-in delay to accommodate for such a warm up period.

Figure 30:
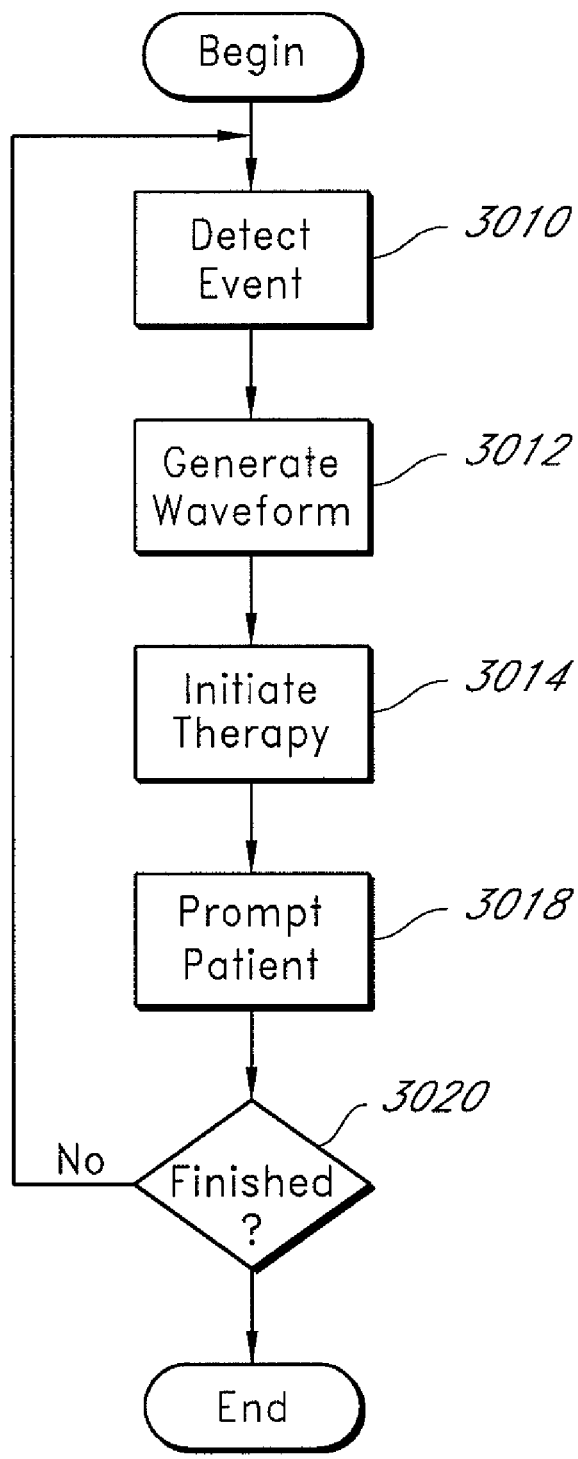
FIG. 30 is a flow chart illustrating a process performed in applying electrical stimulation therapy.

FIG. 30 depicts a flow chart illustrating an embodiment of a method by which a neurostimulation system (such as the implantable neurostimulator device 110, FIG. 1) provides a course of therapy. Initially, the system receives EEG data or other electrographic signals (step 3010)—this can be performed on a continuous basis, alongside and in parallel with any other detection and other operations performed by the device 110. The EEG data is then analyzed, processed and stored.

A neurological event can then be detected (step 3010), or alternatively some other time-related event may then occur (such as receipt of a time scheduling interrupt from the CPU 432). For example, in some embodiments, the event can be triggered according to a preprogrammed schedule. Following the event, a treatment waveform for a first course of therapy, including stimulation time and signal details, is generated (step 3012). The treatment waveform generation process can involve extracting information from a measured electrographic signal via the detection subsystem 423 and generating a waveform representative of an adaptive stimulation signal based on the extracted information. Alternatively, the treatment waveform can be generated by the CPU 432 based on a range of stimulation settings preprogrammed into the CPU 432 via programmer 312 by the physician or clinician. Otherwise, any desired waveform can be employed, for example predetermined waveforms stored in memory subsystem 431, and need not be created in real time.

Application of the stimulation therapy is then initiated (step 3014) at the appropriate time. Delivery of stimulation is scheduled by the CPU 432 (FIG. 4) and tied to a timer interrupt. When the timer interrupt is received, synchronization to the therapy schedule has been accomplished, and the CPU 432 commands the stimulation subsystem 424 (and in particular the stimulation waveform generator 2912 and the stimulation signal generator 2914, FIG. 29) to deliver the appropriate stimulation signal, thereby applying stimulation therapy to the patient. The nature of the desired stimulation waveform, if it is simple, can be expressed in the command from the CPU 432, or alternatively, a representation of the desired stimulation waveform, if stored in the memory subsystem 431, can be caused by the CPU 432 to be streamed to the stimulation subsystem 424. Once the therapy has been delivered, the communication subsystem 434 provides a prompt to the patient to provide input on the therapy received (step 3018). As discussed above, the patient can provide input to regarding the therapy to a recording device contained within the device 110 or alternatively, to an external patient-reporting device 332 which can be periodically or continuously connected to the device 110 via a wireless link. If there are additional scheduled pulses or waveforms to be applied, the therapy plan is optionally revised, and the synchronization and application steps are repeated as necessary.

In some embodiments, after a patient has used the device 110 and recorded feedback in response to a plurality of prompts, as described above, the recorded feedback can be used to provide a more optimized therapy to the patient.

Figure 31:
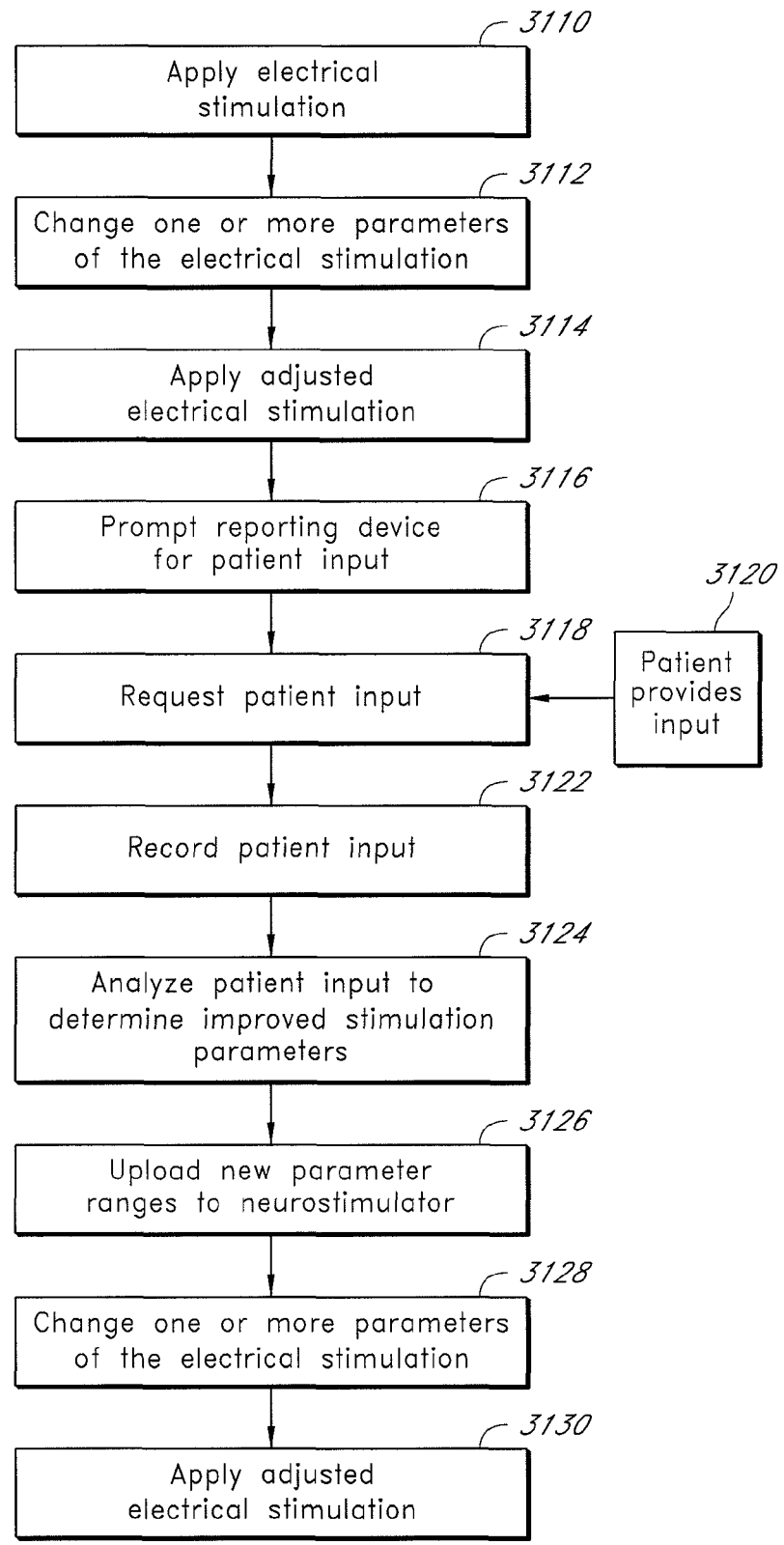
FIG. 31 is a flow chart illustrating a process for delivering and monitoring and adjusting the therapy applied to a patient according to patient feedback.

For example, FIG. 31 depicts a flow chart illustrating an embodiment of a method which can incorporate the device 110 to automatically vary the value of one or more of the therapy parameters and request the patient's feedback concerning the adjustment and records the patient's input. In some embodiments, the method can include adjustment of value of one or more therapy parameters to a more optimized value based on the feedback from the patient.

Initially, the device 110 provides a first treatment, such as an electrical stimulation, to a patient in response to a detected event or alternatively, according to a programmed schedule, as discussed above (step 3110). Following application of the first treatment, the auto-adjust module 440 (FIG. 4) can be configured to signal the CPU to adjust one or more parameters of the treatment to provide a second, different treatment to the patient (step 3112).

For example, the auto-adjust module 440 can alter one or more parameters of the treatment in response to an event detected by the detection subsystem 423, or alternatively, the auto-adjust module 440 can be programmed to change the parameters of the therapy at fixed times throughout the day for a short period of time to explore optimal parameters for the therapy. As discussed above, the auto-adjust module 440 can also be configured to randomly change the parameters of the therapy signal, select values from a range of values preprogrammed by a clinician, follow a predetermined schedule of value changes, such as that described above with reference to FIG. 4, or in any other manner.

The second treatment, comprising for example a recently changed electrical stimulation signal, can then be delivered to the patient by the device 110 (step 3114). In conjunction with the second treatment, or at one or a plurality of times time after the change to the second treatment, the patient is provided with a prompt to provide feedback regarding the therapy being applied (step 3116). The prompt can comprise an audible signal, a visual signal, a tactile signal a different electrical stimulation, a wireless signal sent to an external device or any other suitable signal for prompting the patient. The prompt itself can include an indication to provide an input expressing his or her opinions about the therapy and the state of his or her conditions. For example, the prompt can comprise a human or simulated voice instructing "Please describe your opinion about your treatment," or any other statement. Alternatively, the prompt can be any generic prompt (e.g., a tone, light, vibration, etc) and the patient can be instructed as to the intended meaning of such a prompt.

In some embodiments, the prompt can comprise a wireless signal sent to an external patient-reporting device 332 such as a PDA, smart cell phone or other communication device that will then prompt the patient with an audible signal, such as a beep, ring, light, vibration, voice, etc. In addition, the wireless signal to the external reporting device 332 can trigger the external reporting device 332 to open a program, such as an email, in which the patient can record his or her feedback. In some embodiments, such an email can include preformatted fields for the patient to fill in his or her feedback regarding one or a plurality of categories of feedback. Additionally, the email can be pre-addressed to the patient's physician or any other address to which the feedback should be sent.

In response to the prompt, the patient can provide feedback, in any manner, regarding his or her opinions about the therapy (step 3120). The prompts can be issued once or a plurality of times after the treatment has been changed by the auto-adjust module 440. The feedback can be a freeform commentary expressing his thoughts and opinions regarding the therapy and his condition. In some embodiments, the patient can be asked to provide feedback in the form of graded responses (for example from one to five) to standardized questions to elicit specific information regarding the adjusted therapy. In some embodiments, the patient can also provide information on additional concomitant therapies, such as medication, to identify and assess any possible interactions between the therapy being applied and the concomitant therapy.

The input provided by the patient is then recorded by the patient-reporting device (step 3122). The patient-reporting device 332 can store the input in a database for future access by the treating physician. In some embodiments, the patient-reporting device can have a communications capability and can upload the patient input to the device 110, to the clinician or other treating physician, or to an external database for analysis.

Steps 3112-3122 can be performed once or a or plurality of times, during which either the treatment is changed (step 3112) and/or the is prompt is issued (step 3114) once or a plurality of times. A clinician using the device 110 can program the device 110 can decide how many treatment changes and how many prompts to use.

This portion of the method can be repeated as many times as desired to determine the optimal values of the associated parameters for the patient's condition. Since the variation of the values (step 3112) and prompting (step 3118) is automated, these steps can be performed over a short period of time and can be repeated for long periods of time without clinician involvement. In addition, by repeating the process for short intervals over long periods of time, spurious responses from the patient and responses due to external factors, such as time of day, can be identified and analyzed.

After step 3122, the patient feedback can be analyzed, for example, to determine the optimal parameters for the patient's therapy (step 3124). In some embodiments, the device 110 can be configured to automatically analyze the patient feedback and suggest a new range of parameters for the subsequent therapy.

In step 3124, the patient feedback can be provided to the clinician so that the clinician review the feedback from the patient and determine how to optimize the values of the associated parameters. For example, the clinician can review the patient feedback and determine if any of the values provided optimum results. If the clinician determined that none of the values used by the auto-adjust module 440 (FIG. 4) were optimum, the clinician may decide that additional values should be investigated. Thus, in such a situation, the clinician may decide to re-program the auto-adjust module to investigate such additional values.

On the other hand, the clinician may decide that that particular value is the optimum value because it provided the most positive feedback. Alternatively, the clinician may decide that a new value, between two of the values used by the auto-adjust module 440, is the optimum value, based on pro and con feedback from the patient regarding the two values used by the auto-adjust module 440.

In some embodiments, as discussed above, the patient feedback can automatically be sent to the clinician. Alternatively, the patient can physically bring the patient-reporting device (e.g., BLACKBERRY PDA, "smart" cell phone, Internet-enabled PC or other standard communications device) to the clinician for analysis of the patient feedback. The patient feedback can be analyzed after each change in therapy, as depicted herein, or alternatively, the data can be analyzed after data has been gathered for several changes in treatment.

In the step 3130, the new adjusted or optimized values if the parameters for the therapy can then be uploaded to the device 110 for subsequent treatments. After the values have been uploaded, the device 110 can use the new values to apply adjusted electrical stimulation to the patient (step 3130). In some embodiments, the adjusted or optimized values correspond to parameters of the stimulation signal (e.g., frequency, duration, waveform) provided by the therapy subsystem 424. Thus, optionally, the step 3128 can include a step of disabling the auto-adjust module 440 and uploading the adjusted or optimized value to the memory facility for parameters and settings 561 of the memory 431 (FIG. 4) so that the therapy subsystem 424 then uses the adjusted or optimized value indefinitely, without the variations provided by the auto-adjust module 440.

Although the invention(s) presented herein have been disclosed in the context of certain preferred embodiments and examples, it will be understood by those skilled in the art that the invention(s) extend beyond the specifically disclosed embodiments to other alternative embodiments and/or uses of the invention(s) and obvious modifications and equivalents thereof. Thus, it is intended that the scope of the invention(s) herein disclosed should not be limited by the particular embodiments described above, but should be determined only by a fair reading of the claims that follow.

What is claimed is:

1. A device for delivering therapy to a patient and soliciting information about the therapy from the patient comprising:
    a therapy module configured to provide a therapy characterized by at least one parameter to the patient;
    a detection module configured to automatically detect a physiological event in the patient;
    a controller configured to automatically determine the at least one parameter of the therapy based on the detected physiological event;
    a prompting module configured to prompt the patient to express the patient's opinion about the therapy; and
    an input module configured to receive an input corresponding to the patient's expressed opinion;
    wherein the controller is further configured to automatically determine whether to change the at least one parameter of the therapy based on the detected physiological event and the expression of the patient's opinion about the therapy.

2. The device of claim 1, wherein the controller further comprises settings for changing the therapy.

3. The device of claim 2, wherein the therapy comprises electrical stimulus, the settings for changing the therapy comprising an allowable range of values for the at least one parameter of the electrical stimulus.

4. The device of claim 1, wherein the controller further comprises a memory configured to store information about the changes made to the therapy.

5. The device of claim 4, wherein the controller further comprises a communication module configured to download information about the changes made to the therapy.

6. The device of claim 1, further comprising a communication module configured to communicate with an external reporting device configured to receive and record patient opinions about the adjusted therapy.

7. The device of claim 6, wherein the prompting module is configured to trigger the external reporting device to issue a prompt to the patient.

8. The device of claim 1, wherein the prompting module is configured to prompt the patient a plurality of times each time a change to the therapy is made by the controller.

9. The device of claim 1, wherein the controller is configured to change the at least one parameter a plurality of times, the prompting module being configured to prompt the patient at least once between each change performed by the controller.

10. The device of claim 9, wherein the prompting module is configured to prompt the patient more than once between two of the changes performed by the controller.

11. The device of claim 1, wherein the prompting module comprises a bone conduction microphone configured to provide an audible signal to the patient.

12. The device of claim 1, wherein the therapy module, the detection module, the controller, and the prompting module are configured to be implanted in a human body.

13. A method of delivering electrical stimulation therapy provided to a patient with an implantable neurostimulator and soliciting information about the therapy from the patient comprising:
    delivering a first course of electrical stimulation therapy with the implantable neurostimulator with a first value of at least one parameter of the electrical stimulation;
    automatically detecting with the implantable neurostimulator a physiological event in the patient;
    automatically changing the first value to a second value of the least one parameter based on the detected physiological event;
    delivering a second course of electrical stimulation therapy with the implantable neurostimulator to the patient with the second value;
    prompting the patient to provide input reflecting the patient's opinion about the therapy;
    receiving an input corresponding to the patient's expressed opinion about the therapy;
    automatically determining whether to change the at least one parameter of the therapy prior to delivering a third course of electrical stimulation therapy based on the detected physiological event and the input reflecting the patient's opinion about the changed therapy; and
    if, it is determined to change the at least one parameter of the therapy prior to delivering a third course of electrical stimulation therapy, changing the at least one parameter of the therapy based on the detected physiological event and the input reflecting the patient's opinion about the therapy.

14. The method of claim 13, further comprising recording the input from the patient.

15. The method of claim 14, wherein the input is stored in the implantable neurostimulator.

16. The method of claim 14, wherein the input is stored in an external patient-reporting device.

17. The method of claim 16, wherein the external patient-reporting device comprises a website linked to a handheld communication device.

18. The method of claim 16, wherein the external patient-reporting device comprises an Internet-enabled PC.

19. The method of claim 13, wherein prompting the patient to provide input further comprises providing a stimulus to the patient that is different from the electrical stimulation therapy characterizable by the at least one parameter.

20. The method of claim 13, wherein prompting the patient to provide input further comprises providing a signal from a bone conduction speaker to the patient.

21. The method of claim 13, wherein the at least one parameter comprises one of a duration, a frequency, an inter-pulse interval, and an amplitude of the electrical.

22. A device for delivering therapy to a patient comprising:
   means for stimulating the patient according to a first treatment of stimulation, the stimulating means being implantable in the patient;
   means for automatically detecting a physiological event in the patient;
   means for automatically varying at least one parameter of the first treatment of stimulation based on the detected physiological event; and
   means for prompting the patient to provide input about the therapy;
   means for receiving an input corresponding to the patient's expressed opinion;
   wherein the varying means further automatically determines whether to vary the at least one parameter of the first treatment of stimulation based on the detected physiological event and the input about the therapy provided by the patient.

23. The device of claim 22, wherein the varying means includes means for varying at least one of pulse amplitude, pulse width, pulse-to-pulse interval, number of electrodes used, and duration of a stimulation signal of the first treatment.

24. The device of claim 23, wherein the varying means comprises means for changing the at least one of pulse amplitude, pulse width, pulse-to-pulse interval, number of electrodes used, and duration of a stimulation signal of the first treatment at a plurality of values in a range of parameters for automatically varying the first treatment.

25. The device of claim 22, wherein the prompting means includes means for requesting patient input a plurality of times without the varying means automatically varying the at least one parameter of the first treatment of stimulation.

26. The device of claim 22 further comprising means for recording the patient input.

27. The device of claim 26, wherein the recording means is collocated with the implantable stimulation means.

28. The device of claim 26, wherein the recording means comprises an external reporting means for receiving and recording the patient feedback.

29. A neurostimulator for delivering therapy to a patient and soliciting information about the therapy from the patient comprising:
   a therapy module configured to provide electrical neurostimulation characterized by at least one parameter to the patient;
   a detection module configured to automatically detect a neurological event in the patient;
   a prompting module configured to prompt the patient to express the patient's opinion about the electrical neurostimulation;
   an input module configured to receive an input corresponding to the patient's expressed opinion; and
   a controller configured to automatically increase the at least one parameter of the electrical neurostimulation at a plurality of times, and configured to instruct the prompting module to prompt the patient after each increase, and configured to determine the at least one parameter for treatments of electrical neurostimulation subsequent to the plurality of times based on the detected neurological event and the expression of the patient's opinion about the electrical neurostimulation.

30. A neurostimulator for delivering neurostimulation to a patient comprising:
   a therapy module configured to provide electrical neurostimulation characterized by at least one parameter to the patient;
   a detection module configured to automatically detect neurological seizures in the patient;
   a prompting module configured to prompt the patient to express the patient's opinion about the electrical neurostimulation;
   an input module configured to receive an input corresponding to the patient's expressed opinion; and
   a controller configured to automatically change, according to a schedule of parameter changes, the at least one parameter of the electrical stimulation based on the detected neurological seizures, the expression of the patient's opinion about the electrical stimulation, and the schedule of parameter changes, and further configured to automatically select the at least one parameter of the electrical neurostimulation for a regiment of therapy based on the parameter changes, the detected neurological seizures, and the expression of the patient's opinion about the electrical stimulation.

* * * * *